US006974695B2

(12) United States Patent
Vogels et al.

(10) Patent No.: US 6,974,695 B2
(45) Date of Patent: *Dec. 13, 2005

(54) COMPLEMENTING CELL LINES

(75) Inventors: Ronald Vogels, Linschoten (NL); Menzo J. E. Havenga, Alphen a/d Rijn (NL); Majid Mehtali, Coueron (FR)

(73) Assignee: Crucell Holland B.V., Leiden (NL)

( * ) Notice: Subject to any disclaimer, the term of this patent is extended or adjusted under 35 U.S.C. 154(b) by 134 days.

This patent is subject to a terminal disclaimer.

(21) Appl. No.: 10/002,750

(22) Filed: Nov. 15, 2001

(65) Prior Publication Data

US 2003/0185801 A1 Oct. 2, 2003

Related U.S. Application Data

(63) Continuation-in-part of application No. 09/713,678, filed on Nov. 15, 2000, now Pat. No. 6,492,169.

(51) Int. Cl.[7] .................. C12N 5/02; C12N 5/08; C12N 15/63; C12N 7/00
(52) U.S. Cl. ............. 435/325; 435/366; 435/69.1; 435/320.1; 435/455; 435/235.1
(58) Field of Search ................. 435/325, 366, 435/69.1, 320.1, 455, 235.1; 536/23.1

(56) References Cited

U.S. PATENT DOCUMENTS

| | | |
|---|---|---|
| 4,487,829 A | 12/1984 | Sharp et al. |
| 4,517,686 A | 5/1985 | Ruoslahti et al. |
| 4,578,079 A | 3/1986 | Ruoslahti et al. |
| 4,589,881 A | 5/1986 | Pierschbacher et al. |
| 4,593,002 A | 6/1986 | Dulbecco |
| 4,792,525 A | 12/1988 | Ruoslahti et al. |
| 4,797,368 A | 1/1989 | Carter et al. |
| 4,956,281 A | 9/1990 | Wallner et al. |
| 5,024,939 A | 6/1991 | Gorman |
| 5,096,815 A | 3/1992 | Ladner et al. |
| 5,166,320 A | 11/1992 | Wu et al. |
| 5,198,346 A | 3/1993 | Ladner et al. |
| 5,204,445 A | 4/1993 | Plow et al. |
| 5,223,394 A | 6/1993 | Wallner |
| 5,223,409 A | 6/1993 | Ladner et al. |
| 5,240,846 A | 8/1993 | Collins et al. |
| 5,246,921 A | 9/1993 | Reddy et al. |
| 5,332,567 A | 7/1994 | Goldenberg |
| 5,349,053 A | 9/1994 | Landolfi |
| 5,403,484 A | 4/1995 | Ladner et al. |
| 5,436,146 A | 7/1995 | Shenk et al. |
| 5,443,953 A | 8/1995 | Hansen et al. |
| 5,474,935 A | 12/1995 | Chatterjee et al. |
| 5,521,291 A | 5/1996 | Curiel et al. |
| 5,534,423 A | 7/1996 | Palsson et al. |
| 5,543,328 A | 8/1996 | McClelland et al. |
| 5,547,932 A | 8/1996 | Curiel et al. |
| 5,552,311 A | 9/1996 | Sorscher et al. |
| 5,559,099 A | 9/1996 | Wickham et al. |
| 5,571,698 A | 11/1996 | Ladner et al. |
| 5,622,699 A | 4/1997 | Ruoslahti et al. |
| 5,712,136 A | 1/1998 | Wickham et al. |
| 5,731,190 A | 3/1998 | Wickham et al. |
| 5,770,442 A | 6/1998 | Wickham et al. |
| 5,837,511 A | 11/1998 | Falck-Pedersen et al. |
| 5,846,782 A | 12/1998 | Wickham et al. |
| 5,849,561 A | * 12/1998 | Falck-Pedersen ........ 435/235.1 |
| 5,856,152 A | 1/1999 | Wilson et al. |
| 5,871,727 A | 2/1999 | Curiel |
| 5,871,982 A | 2/1999 | Wilson et al. |
| 5,877,011 A | 3/1999 | Armentano et al. |
| 5,880,102 A | 3/1999 | George et al. |

(Continued)

FOREIGN PATENT DOCUMENTS

| | | |
|---|---|---|
| DE | 197 54 103 A 1 | 6/1999 |
| DE | 199 18 023 A 1 | 9/2000 |

(Continued)

OTHER PUBLICATIONS

Al. van Olphen and S. Mittal. "Development and Characterization of Bovine X Human Hybrid Cell Lines that Efficientlyy Support the Replication of both Wild–Type Bovine and Human Adenoviruses and Those with E1 Deleted." J. of Virol., 2002, p. 5882–5892.*

(Continued)

Primary Examiner—David Guzo
Assistant Examiner—Michael Burkhart
(74) Attorney, Agent, or Firm—TraskBritt

(57) ABSTRACT

A packaging cell line capable of complementing recombinant adenoviruses based on serotypes from subgroup B, preferably adenovirus type 35. The cell line is preferably derived from primary, diploid human cells (e.g., primary human retinoblasts, primary human embryonic kidney cells and primary human amniocytes) which are transformed by adenovirus E1 sequences either operatively linked on one DNA molecule or located on two separate DNA molecules, the sequences being operatively linked to regulatory sequences enabling transcription and translation of encoded proteins. Also disclosed is a cell line derived from PER.C6 (ECACC deposit number 96022940), which cell expresses functional Ad35 E1B sequences. The Ad35-E1B sequences are driven by the E1B promoter or a heterologous promoter and terminated by a heterologous poly-adenylation signal. The new cell lines are useful for producing recombinant adenoviruses designed for gene therapy and vaccination. The cell line can also be used for producing human recombinant therapeutic proteins such as human growth factors and human antibodies. In addition, the cell lines are useful for producing human viruses other than adenovirus such as influenza virus, herpes simplex virus, rotavirus, measles virus.

22 Claims, 38 Drawing Sheets

U.S. PATENT DOCUMENTS

Figure 1:
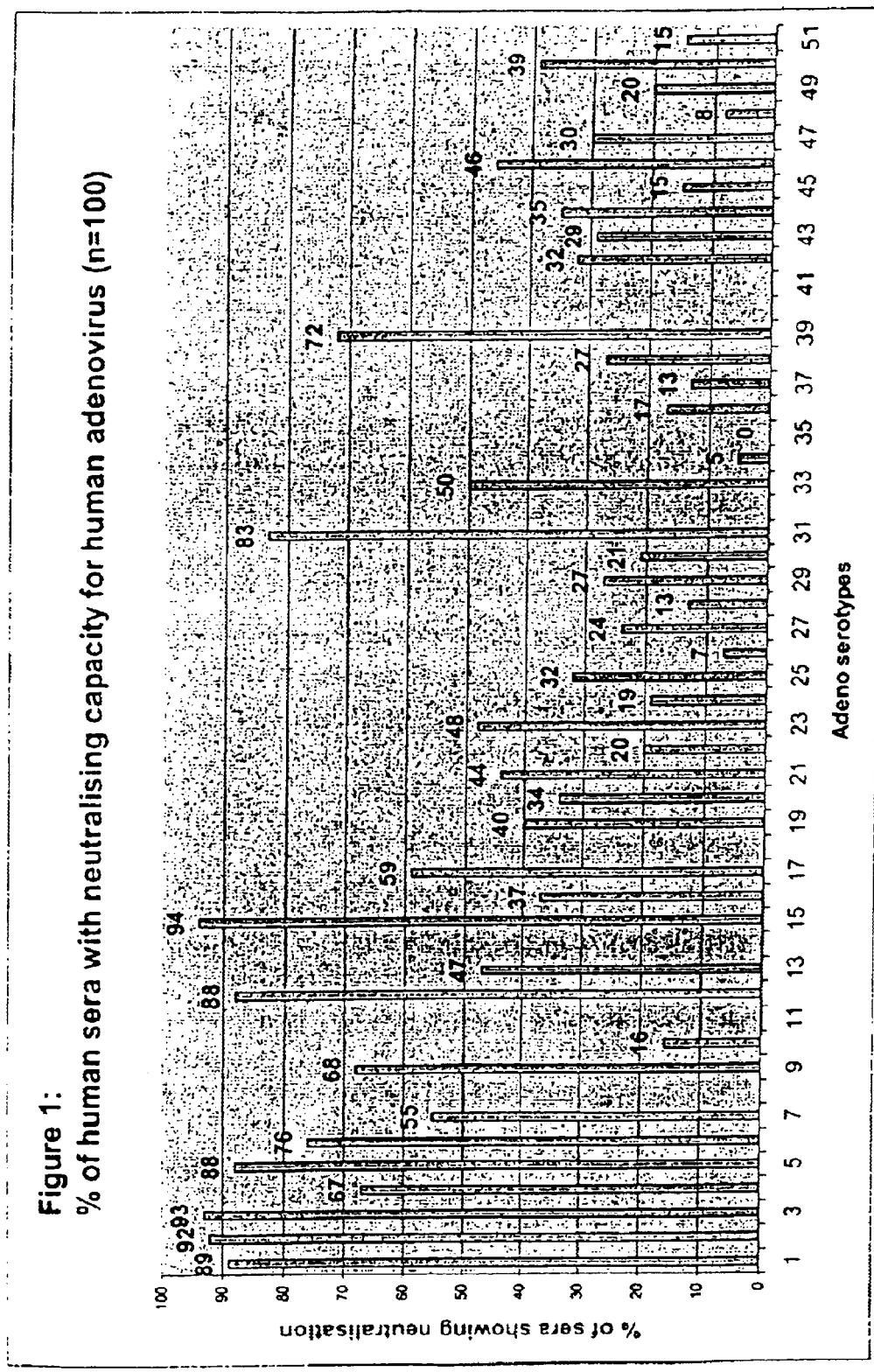

| | | | |
|---|---|---|---|
| 5,922,315 | A | 7/1999 | Roy |
| 5,994,128 | A | 11/1999 | Fallaux et al. |
| 5,994,132 | A | 11/1999 | Chamberlain et al. |
| 6,033,908 | A | 3/2000 | Bout et al. |
| 6,057,155 | A | 5/2000 | Wickham et al. |
| 6,057,158 | A | 5/2000 | Chamberlain et al. |
| 6,063,622 | A | 5/2000 | Chamberlain et al. |
| 6,083,750 | A | 7/2000 | Chamberlain et al. |
| 6,100,086 | A | 8/2000 | Kaplan et al. |
| 6,127,525 | A | 10/2000 | Crystal et al. |
| 6,238,893 | B1 | 5/2001 | Hoeben et al. |
| 6,265,212 | B1 | 7/2001 | Fallaux et al. |
| 6,287,857 | B1 | 9/2001 | O'riordan et al. |
| 6,306,652 | B1 | 10/2001 | Fallaux et al. |
| 6,395,519 | B1 | 5/2002 | Fallaux et al. |
| 6,486,133 | B1 | 11/2002 | Herlyn et al. |
| 6,492,169 | B1 * | 12/2002 | Vogels et al. ............... 435/325 |
| 6,669,942 | B2 | 12/2003 | Perricaudet et al. |
| 2002/0177544 | A1 | 11/2002 | Haack et al. |

FOREIGN PATENT DOCUMENTS

| | | |
|---|---|---|
| EP | 259212 | 8/1987 |
| EP | 1016726 | 12/1998 |
| EP | 0 950 713 | 10/1999 |
| WO | WO 91/00360 | 1/1991 |
| WO | WO 91/05805 | 5/1991 |
| WO | WO 91/05871 | 5/1991 |
| WO | WO 92/02553 | 2/1992 |
| WO | WO 92/13081 | 8/1992 |
| WO | WO 93/03769 | 3/1993 |
| WO | WO 93/06223 | 4/1993 |
| WO | WO 93/07282 | 4/1993 |
| WO | WO 93/07283 | 4/1993 |
| WO | WO 94/08026 | 4/1994 |
| WO | WO 94/10323 | 5/1994 |
| WO | WO 94/11506 | 5/1994 |
| WO | WO 94/15644 | 7/1994 |
| WO | WO 94/17832 | 8/1994 |
| WO | WO 94/24299 | 10/1994 |
| WO | WO 94/26915 | 11/1994 |
| WO | WO 95/05201 | 2/1995 |
| WO | WO 95/06745 | 3/1995 |
| WO | WO 95/14785 | 6/1995 |
| WO | WO 95/21259 | 8/1995 |
| WO | WO 95/26412 | 10/1995 |
| WO | WO 95/27071 | 10/1995 |
| WO | WO 95/31187 | 11/1995 |
| WO | WO 95/31566 | 11/1995 |
| WO | WO 96/00326 | 1/1996 |
| WO | WO 96/00790 | 1/1996 |
| WO | WO 96/07739 | 3/1996 |
| WO | WO 96/10087 | 4/1996 |
| WO | WO 96/12030 | 4/1996 |
| WO | WO 96/13597 | 5/1996 |
| WO | WO 96/13598 | 5/1996 |
| WO | WO 96/14837 | 5/1996 |
| WO | WO 96/17073 | 6/1996 |
| WO | WO 96/18740 | 6/1996 |
| WO | WO 96/24453 | 8/1996 |
| WO | WO 96/26281 | 8/1996 |
| WO | WO 96/35798 | 11/1996 |
| WO | WO 97/00326 | 1/1997 |
| WO | WO 97/12986 | 4/1997 |
| WO | WO 97/20575 | 6/1997 |
| WO | WO 97/38723 | 10/1997 |
| WO | WO 98/07865 | 2/1998 |
| WO | WO 98/11221 | 3/1998 |
| WO | WO 98/13499 | 4/1998 |
| WO | WO 98/17783 | 4/1998 |
| WO | WO 98/22609 | 5/1998 |
| WO | WO 98/32842 | 7/1998 |
| WO | WO 98/40509 | 9/1998 |
| WO | WO 98/49300 | 11/1998 |
| WO | WO 98/50053 A1 | 11/1998 |
| WO | 1067188 | 7/1999 |
| WO | WO 99/32647 | 7/1999 |
| WO | WO 99/47180 A1 | 9/1999 |
| WO | 102529 | 11/1999 |
| WO | WO 99/55132 | 11/1999 |
| WO | WO 99/58646 | 11/1999 |
| WO | WO 00/03029 | 1/2000 |
| WO | WO 00/24730 A2 | 5/2000 |
| WO | WO 00/31285 | 6/2000 |
| WO | WO 00/52186 | 9/2000 |
| WO | WO 00/70071 A1 | 11/2000 |
| WO | WO 01/04334 | 1/2001 |
| WO | WO 01/90158 A1 | 11/2001 |
| WO | WO 02/24730 | 3/2002 |
| WO | WO 02/27006 | 4/2002 |
| WO | WO 02/40665 | 5/2002 |
| WO | WO 02/40665 A2 | 5/2002 |

OTHER PUBLICATIONS van Olphen, Albert, et al. "Characterization of Bovine Adenovirus Type 3 E1 Proteins and Isolation of E1–Expresing Cell Lines." Virology, 295, p. 5882–5892, 2002.*

Abrahamsen et al. "Construction of an Adenovirus Type 7a E1A– Vector." J. of Virol., 1997, p. 8946–8951.*

PCT International Search Report, PCT/NL01/00824, dated Jul. 19, 2002.

Schiedner et al., Abstract, Efficient transformation of primary human amniocytes by E1 functions of Ad5; generation of new cell lines for adenoviral vector production, Human Gene Therapy, Oct. 10, 2000, pp. 2105–2116, vol 11, No. 15.

Abrahamsen et al., "Construction of an Adenovirus Type 7a E1A Vector," Journal of Virology, Nov. 1997, p. 8946–8951 vol. 71, No. 11.

Albiges–Rizo et al., "Human Adenovirus Serotype 3 Fiber Protein," Journal of Biological Chemistry, 266(6), 3961–3967 (1991).

Anderson, Nature, "Human gene therapy," Apr. 1998, vol. 392, pp. 25–30.

Athappilly et al., "The Refined Crystal Structure of Hexon, the Major Coat Protein of Adenovirus Type 2, at 2·9 A Resolution," J. Mol. Biol. (1994) 242, 430–455.

Bai et al., "Mutations That Alter an Arg–Gly–Asp (RGD) Sequence in the Adenovirus Type 2 Penton Base Protein Abolish Its Cell–Rounding Activity and Delay Virus Reproduction in Flat Cells," Journal of Virology, 67(9), 5198–5205 (1993).

Bailey et al., "Phylogenetic Relationships among Adenovirus Serotypes," Virology, 205, 439–452 (1994).

Ball–Goodrich et al., "Parvoviral Target Cell Specificity: Acquisition of Fibrotropism by a Mutant of the Lymphotropic Strain of Minute Virus of Mice Involves Multiple Amino Acid Substitutions within the Capsid," Virology, 184, 175–186 (1991).

Basler et al., Sequence of the immunoregulatory early region 3 and flanking sequences of adenovirus type 35, 1996, Gene 170:249–254.

Basler et al., "Subgroup B Adenovirus Type 35 Early Region 3 mRNAs Differ from Those of the Subgroup C Adenoviruses," VIROLOGY 215, 165–177 (1996).

Batra et al., "Receptor–mediated gene delivery employing lectin–binding specificity," Gene Therapy, 1, 255–260 (1994).

Berendsen, Herman J.C., A Glimpse of the Holy Grail, Science, 1998, vol. 282, pp. 642–643.

Boursnell et al., "In vitro construction of a recombinant adenovirus Ad2:Ad5," Gene, 13, 311–317 (1981).

Bridge et al., "Adenovirus Early Region 4 and Viral DNA Synthesis," Virology 193, 794–801 (1993).

Brody et al., "Adenovirus–Mediated in Vivo Gene Transfer," Annals New York Academy of Sciences pp. 90–100.

Caillet–Boudin et al., "Functional and Structural Effects of an Ala to Val Mutation in the Adenovirus Serotype 2 Fibre," J. Mol. Biol., 217, 477–486 (1991).

Chiu et al., Folding & Design, "Optimizing energy potential for success in protein tertiary structure prediction," May 1998, 3:223–228.

Chroboczek et al., "The Sequence of the Genome of Adenovirus Type 5 and Its Comparison with the Genome of Adenovirus Type 2," Virology, 186, 280–285 (1992).

Chu et al., "Cell targeting with reroviral vector particles containing antibody–envelope fusion proteins," Gene Therapy, 1, 292–299 (1994).

Cotten et al., "Transferrin–polycation–mediated introduction of DNA into human leukemia cels: Stimulations by agents that affect the survival of transfered DNA or modulate transferrin receptors levels," Proc. Natl. Acad. Sci. USA, 87, 4033–4037 (1990).

Cotten, "High–efficiency receptor–mediated delivery of small and large (48 kilobase gene contructs using the endosome–disruption activity of defective or chemically inactivated adenovirus particles," Proc. Natl. Acad. Sci. USA 89, 6094–6098 (1992).

Crawford–Miksza et al., "Adenovirus Serotype Evolution Is Driven by Illegitimate Recombination in the Hypervariable Regions of the Hexon Protein," Virology, 224, 357–367 (1996).

Crawford–Miksza et al., "Analysis of 15 Adenovirus Hexon Proteins Reveals the Location and Structure of Seven Hypervariable Regions Containing Serotype–Specific Residues," Journal of Virology, Mar. 1996, p. 1836–1844.

Crompton et al., "Expression of a foreign epitope on the surface of the adenovirus hexon," J. Gen. Virol., 75(1), 133–139 (1994).

Crystal, Ronald G., "Transfer of Genes to Humans: Early Lessons and Obstacles to Success," Science, 270, 404–410 (1995).

Curiel et al., "High–Efficiency Gene Transfer Mediated by Adenovirus Coupled to DNA–Polylysine Complexes," Human Gene Therapy, 3, 147–154 (1992).

Curiel et al., "Adenovirus enhancement of transferring–polylysine–mediated gene delivery," Proc. Natl. Acad. Sci. USA, 88, 8850–8854 (1991).

De Jong et al., "Adenovirus Isolates From Urine of Patients with Acquired Immunodeficiency Syndrome," The Lancet, Jun. 11, 1993 pp. 1293–1296.

De Jong et al., Adenovirus from Human Immunodeficiency Virus–Infected Individuals, Including Two Strains That Represent New Candidate Serotypes Ad50 and Ad51 of Species B1 and D, Respectively, Journal of Clinical Microbiology, Dec. 1999, p. 3940–45, vol. 37, No. 12, American Society for Microbiology.

Defer et al., "Human Adenovirus–Host Cell Interactions: Comparative Study with Members of Subgroups B and C," Journal of Virology, 64(8), 3661–3673 (1990).

Deonarain, "Ligand–targeted receptor–mediated vectors for gene delivery," (1998) Expert Opin. Ther. Pat. 8: 53–69.

Dukema et al., "Transformation of Primary Rat Kidney Cell by DNA Fragments of Weekly Oncogenic Adenoviruses," Journal of Virology, Dec. 1979, p. 943–950.

Douglas J T et al.: "Strategies to accomplish targeted gene delivery to muscle cells employing tropism–modified adenoviral vectors" Neuromusclar Disorders, Pergamon Press, GB, vol. 7, Jul. 1997, pp. 284–298, XP002079944 ISSN: 0960–8966.

Dupuit et al., "Regenerating Cells in Human Airway Surface Epithelium Represent Preferential Targets for Recombinant Adenovirus," Human Gene Therapy, 6, 1185–1193 (1995).

Eck et al., "Gene–Based Therapy," Goodman & Gillman's The Pharmacological Basis of Therapeutics, Mc–Graw–Hill, New York, N.Y., pp. 77–101.

Etienne–Julan et al., "The efficiency of cell targeting by recombinant retroviruses depends on the nature of the receptor and the composition of the artificial cell–virus linker," Journal of General Virology, 73, 3251–3255 (1992).

Falgout et al., "Characterization of Adenovirus Particles Made by Deletion Mutants Lacking the Fiber Gene," Journal of Virology, 62(2), 622–625 (1998).

Flomenberg et al., "Molecular Epidemiology of Adenovirus Type 35 Infections in Immunocompromised Hosts," The Journal of Infectious Diseases vol. 155, No. 6, Jun. 1987.

Francki et al., "Classification and Nomenclature of Viruses," Fifth Report of the International Committee on Taxonomy of Viruses; Virology Division of the International Union of Microbiology Societies pp. 140–143.

Gall et al., "Construction and characterization fo Hexon–Chimeric Adenovirus: Specification of adenovirus serotype," 72(12) Journal of Virology 10260–64 (1998).

Gall et al., "Adenovirus Type 5 and 7 Capsid Chimera: Fiber Replacement Alters Receptor Tropism without Affecting Primary Immune Neutralization Epitopes," Journal of Virology, Apr. 1996, p. 2116–2123.

George et al., "Gene therapy progress and prospects: adenoviral vectors," Gene Therapy (2003) 10, 1135–1141.

Gorecki, "Prospects and problems fo gene therapy: an update," (2001) Expert Opin. Emerging Drugs 6(2): 187–98.

Greber et al., "Stepwise Dismantling of Adenovirus 2 during Entry into Cells," Cell, 75, 477–486 (1993).

Green et al., "Evidence for a repeating cross, sheet structure in the adenovirus fibre," EMBO Journal, 2(8), 1357–1365 (1983).

Grubb et al., Inefficient gene transfer by adenovirus vector to cystic fibrosis airway epithelia of mice and humans, Nature, 371, 802–806 (1994).

Gurunathan et al., American Association of Immunologists, "CD40 Ligand/Trimer DNA Enhances Both Humoral and Cellular Immune Responses and Indicates Protective Immunity to Infectious and Tumor Challenge," 1998, 161:4563–4571.

Han et al., "Ligand–directed retroviral targeting of human breast cancer cells," Proc. Natl. Acad. Sci. USA, 92, 9747–9751 (1995).

He et al., "A simplified for generating recombinant adenovirus," Proc. Natl. Acad. Sci. USA vol. 95, pp. 2509–2514, Mar. 1998.

Henry et al., "Characterization of the Knob Domain of the Adenovirus Type 5 Fiber Protein Expressed in *Escherichia coli*," Journal of Virology, 68(8), 5239–5246 (1994).

Hidaka, Chisa, et al., "CAR–dependent and CAR–independent pathways of adenovirus vector–mediated gene transfer and expression in human fibroblasts," 013(4) The Journal of Clinical Investigation 579–87 (Feb. 1999).

Hierholzer et al., "Adenoviruses from Patients with AIDS: A Plethora of Serotypes and A Description of Five New Serotypes of Subgenus D (Types 43–47)," The Journal Of Infectious Diseases vol. 158, No. 4 Oct. 1988.

Hong et al., "The Amino Terminus of the Adenovirus Fiber Protein Encodes the Nuclear Localization Signal," Virology, 185(2), 758–767 (1991).

Horvath et al., "Nonpermissivity of Human Peripheral Blood Lymphocytes to Adenovirus Type 2 Infection," Journal of Virology, 62(1), 341–345 (1988).

Huang et al., "Upregulation of Integrins γ3 and γ5 on Human Monocytes and T Lymphocytes Facilitates Adenovirus–Mediated Gene Delivery," Journal of Virology, 69(4), 2257–2263 (1995).

Imler et al., "Novel complementation cell lines derived from human lung carcinoma A549 cells support the growth of E1–deleted adenovirus vectors," vol. 3: p. 75–84, 1996.

Jolly; viral vector systems for gene therapy, 1994, Cancer Gene Therapy, vol. 1, No. 1: 51–64.

Kang et al., "Molecular Cloning And Physical Mapping Of The Dna Of Human Adenovirus Type 35," Acta Microbiologica Hungarica 36 (1), pp. 67–75 (1989).

Kang et al., "Relationship Of E1 And E3 Regions Of Human Adenovirus 35 To Those Of Human Adenovirus Subgroups A, C And D," Acta Microbiological Hungarica 36 (4), pp. 445–457 (1989).

Karayan et al., "Oligomerization of Recombinant Penton Base of Adenovirus Type 2 and Its Assembly with Fiber in Baculovirus–Infected Cells," Virology, 202, 782–795 (1994).

Kass–Eisler et al., "Quantitative determination of adenovirus–mediated gene delivery to rat cardiac myocytes *in vitro* and *in vivo*," Proc. Natl. Acad. Sci. USA, 90, 11498–11502 (1993).

Kmiec, "Gene Therapy," American Scientist, vol. 87, pp. 240.

Komoriya et al., The Minimal Essential Sequence for a Major Cell Type–specific Adhesion Site (CSI) within the Alternatively Spliced Type III Connecting Segment Domain of Fibronectin Is Leucine–Aspartic Acid–Valine,: Journal of Biological Chemistry, 266(23), 11498–11502 (1993).

Krasnykh et al.: "Generation Of Recombinant Adenovirus Vectors With Modified Fibers For Altering Viral Tropism" Journal Of Virology, The American Society For Microbiology, US, vol. 70, No. 10, Oct. 1, 1996, pp. 6839–6846, XP002067518 ISSN: 0022–538X.

Lattanzi, Laura, et al., "High Efficiency Myogenic Conversion of Human Fibroblasts by Adenoviral Vector–mediated *MyoD* Gene Transfer," 101(10) J. Clin. Invest. 2119–28 (May 1998).

Lee et al., "The Constitutive expression of the immunomodulatory gp 19k protein in E1; E3 adenoviral vectors strongly reduces the host cytotoxic T cell response against the vector," Gene Therapy (1995) 2, 256–262.

Levrero et al., "Defective and nondefective adenovirus vectors for expressing foreign genes in vitro and in vivo," Gene, 101 (1991) 195–202.

Li et al., "Genetic Relationship between Thirteen Genome Types of Adenovirus 11, 34, and 35 with Different Tropisms," Intervirology 1991;32:338–350.

Liu et al., Molecular Basis of the inflammatory response to adenovirus vectors. Gene Therapy (2003 10, 935–40.

Maraveyas et al., "Targeted Immunotherapy B An update with special emphasis on ovarian cancer," Acta Oncologica, 32(7/8), 741–746 (1993).

Mastrangeli et al., "Sero–Switch" Adenovirus–Mediated *In Vivo* Gene Transfer: Circumvention of Anti–Adenovirus Humoral Immune Defenses Against Repeat Adenovirus Vector Administration by Changing the Adenovirus Serotype, Human Gene Therapy, 7, 79–87 (1996).

Mathias et al., "Multiple Adenovirus Serotypes Use v Integrins for Infection," Journal of Virology, 68(10), 6811–6814 (1994).

Mautner et al., "Recombination in Adenovirus: DNA Sequence Analysis of Crossover Sites in Intertypic Recombinants," Virology, 131, 1–10 (1983).

Mautner et al., "Recombination in Adenovirus: Analysis of Crossover Sites in Intertypic Overlap Recombinants," Virology, 139, 43–52, (1984).

Merriam–Webster Dictionary (on line) retrieved from the internet<URL:http://www.m–w.com/cgi–bin/dictionary, "derive," 2002.

Michael et al., "Addition of a short peptide ligand to the adenovirus fiber protein," Gene Therapy, 2, 660–668 (1995).

Michael et al., "Binding–incompetent Adenovirus Facilitates Molecular Conjugate–mediated Gene Transfer by the Receptor–mediated Endocytosis Pathway," Journal of Biological Chemistry, 268(10), 6866–6869 (1993).

Miller et al., "Targeted vectors for gene therapy," FASEB Journal, 9, 190–199 (1995).

Neda et al., "Chemical Modification of an Ecotropic Murine Leukemia Virus Results in Redirection of Its Target Cell Specificity," Journal of Biology Chemistry, 266(22), 14143–14146 (1991).

Nemerow et al., "The Role of αv Integrins in Adenovirus Infection," Biology of Vitronectins and their Receptors, 177–184 (1993).

Nemerow et al., "Adenovirus entry into host cells: a role for $α_v$ integrins," Trends In Cell Biology, 4, 52–55 (1994).

Ngo et al., The Protein Folding Problem and Tertiary Structure Prediction, "Computational Complexity, Protein Structure Prediction, and Levinthal Paradox," 1994, Merz et al. (editors), Birkhauser, Boston, MA, pp. 433 and 492–95.

Novelli et al., "Deletion Analysis of Functional Domains in Baculovirus–Expressed Adenovirus Type 2 Fiber," Virology, 185, 365–376 (1991).

Orkin et al., "Report and Recommendations of the Panel to Assess the NIH Investment in Research on Gene Therapy," (1995), [Retrieved on Nov. 16, 2004] [online] Retrieved from http://www.nih.gov/news/panelrep.html.

Peteranderl et al., "Trimerization of the Heat Shock Transcription Factor by a Triple–Stranded–Helical Coiled–Coil," Biochemistry, 31, 12272–12276 (1992).

Prince, "Gene Transfer: A Review Of Methods And Applications," Pathology (1998), 30, pp. 335–347.

Pring–Akerblom et al., "Sequence Characterization and Comparison of Human Adenovirus Subgenus B and E Hexons," Virology, 212, 232–36 (1995).

Ragot et al., "Efficient adenovirus–mediated transfer of a human minidystrophin gene to skeletal muscle of mdx mice" Nature, Macmillan Journals Ltd. London, GB, vol. 361, No. 6413, 1993, pp. 647–650, XP002162515 ISSN: 0028–0836.

Rea et al., "Highly efficient transduction of human monocyte–derived dendritic cells with a subgroup B fiber–modified adenovirus vectors enhances transgene–encoded antigen presentation to cytotoxic T cells," Journal Of Immunology, Apr. 15, 2000) 166 (8) 5236–44., —Apr. 15, 2001 XP02192775.

Robbins et al., "Viral Vectors for Gene Therapy," Pharmacol. Ther. vol. 80, No. 1, pp. 35–47, 1998.

Roberts et al., "Three–Dimensional Structure of the Adenovirus Major Coat Protein Hexon," Science, 232, 1148–51 (1986).

Roelvink et al., The Coxsackievirus–Adevirus Receptor Protein Can Function as a Cellular Attachment Protein for AdenovirusSerotypes from Subgroups A, C, D, E, and F, Journal Of Virology, Oct. 1998, p. 7909–7915, vol. 72, No. 10.

Romano, "Gene Transfer in Experimental Medicine," Drug & News Perspectives, vol. 16, No. 5, 2003, 13 pages.

Russell et al., "Retroviral vectors displaying functional antibody fragments," Nucleic Acids Research, 21(5), 1081–1085 (1993).

Russell, "Replicating Vectors for Gene Therapy of Cancer: Risks, Limitations and Prospects," Eurpean Journal of Cancer, vol. 30A, No. 8, pp. 1165.

Sabourin et al., "The molecular regulation of myogenesis," (2000) Clin. Genet. 57(1): 16–25.

Schurr et al., "Two New Candidate Adenovirus Serotypes," Intervirology 1993;36:79–83.

Schulick et al., "Established Immunity Precludes Adenovirus–mediated Gene Transfer in Rat Carotid Arteries," The Journal of Clinical Investigation Vol. 99, No. 2, Jan. 1997, 209–219.

Segerman et al.: "Adenovirus types IIp and 35p show high binding efficiencies for committed hematopoietic cell lines and are infective to these cell lines" Journal of Virology, The American Society for Microbiology, US, vol. 74, No. 3, Feb. 2000, pp. 1457–1467, XP002161682 ISSN: 0022–538X.

Shayakhmetov et al., "Efficient Gene Transfer into Human CD34+ Cells by a Retargeted Adenovirus Vector," Journal of Virology, Mar. 2000, p. 2567–2583.

Signäs et al., "Adenovirus 3 Fiber Polypeptide Gene: Implications for the Structure of the Fiber Protein," Journal of Virology, 53(2), 672–678 (1985).

Silver et al., "Interaction of Human Adenovirus Serotype 2 with Human Lymphoid Cells," Virology, 165, 377–387 (1988).

Stevenson et al.; Selective Targeting of Human Cells by a Chimeric Adenovirus Vector Containing a Modified Fiber Protein, 1997, Journal of Virology, vol. 71: 4782–4790.

Stewart et al., "Difference imaging of adenovirus: bridging the resolution gap between X–ray crystallography and electron microscopy,"EMBO Journal, 12(7), 2589–2599 (1993).

Stratford–Perricaudet LD et al.; "Widespread Long–Term Gene Transfer To Mouse Skeletal Muscles And Heart" Journal of Clinical Investigation, New York, NY, US, vol. 90 No. 2, Aug. 1992, ISSN; 0021–9738.

Toogood et al., "The Adenovirus Type 40 Hexon: Sequence, Predicated Structure and Relationship to Other Adenovirus Hexons," J. gen. Virol (1989), 70, 3203–3214.

Valderrama–Leon et al., "Restriction Endonuclease Mapping of Adenovirus 35, a Type Isolated from Immunocompromised Hosts," Journal of Virology, Nov. 1985, p. 647–650.

Verma et al., Nature, "Gene therapy–promises, problems and prospects," Sep. 1997, vol. 389, pp. 239–242.

Wadell, "Molecular Epidemiology of Human Adenoviruses," Microbiology and Immunology, vol. 110 pp. 191–120.

Wagner et al., "Coupling of adenovirus to transferring–polylysine/DNA complexes greatly enhances receptor–mediated gene delivery and expression of transfered genes," Proc. Natl. Acad. Sci. USA, 89, 6099–6103 (1992).

Watson et al., "An Antigenic Analysis of the Adenovirus Type 2 Fibre Polypeptide," Journal of Virology, 69, 525–535 (1998).

Wickham et al., "Integrins$_{v3}$ and $_{v3}$ Promote Adenovirus Internalization but Not Virus Attachment," Cell, 73, 309–319 (1993).

Wickham et al., "Integrin γ5 Selectively Promotes Adenovirus Mediated Cell Membrane Permeabilization," Journal of Cell Biology, 127(1), 257–264 (1994).

Wickham et al.; "Increased In Vitro and In Vivo Gene Transfer by Adenovirus Vectors Containing Chimeric Fiber Proteins," Journal of Virology, Nov. 1997, p. 8221–8229.

Zhong et al.; "Recombinant Advenovirus Is An Efficient And Non–Pertubing Genetic Vector For Human Dendritic Cells" European Journal Of Immunology, Weinheim, DE, vol. 29, No. 3, 1999, pp. 964–97, XP000938797 ISSN: 0014–2980.

* cited by examiner

% of human sera with neutralising capacity for human adenovirus (n=100)

Figure 37 B: Alignment of E1B-55K sequences from pCC536s, wtAd35 and wtAd5

Figure 37 A: Alignment of E1B-21K sequences from pCC536s, wtAd35 and wtAd5

SEQUENCE LISTING

```
<160> NUMBER OF SEQ ID NOS: 50

<210> SEQ ID NO 1
<211> LENGTH: 14
<212> TYPE: DNA
<213> ORGANISM: adenoviridae
<220> FEATURE:
<221> NAME/KEY: misc_feature
<222> LOCATION: (1)..(14)
<223> OTHER INFORMATION: /note="5'end"

<400> SEQUENCE: 1
ccaataatat acct                                                       14

<210> SEQ ID NO 2
<211> LENGTH: 21
<212> TYPE: DNA
<213> ORGANISM: adenoviridae
<220> FEATURE:
<221> NAME/KEY: misc_feature
<222> LOCATION: (1)..(21)
<223> OTHER INFORMATION: /note="3'end"

<400> SEQUENCE: 2
```

```
aggtatatta ttgatgatgg g                                              21
```

<210> SEQ ID NO 3
<211> LENGTH: 18
<212> TYPE: DNA
<213> ORGANISM: adenoviridae
<220> FEATURE:
<221> NAME/KEY: misc_feature
<222> LOCATION: (1)..(18)
<223> OTHER INFORMATION: /note="Terminal sequence"

<400> SEQUENCE: 3

```
catcatcaat aatatacc                                                  18
```

<210> SEQ ID NO 4
<211> LENGTH: 47
<212> TYPE: DNA
<213> ORGANISM: Artificial Sequence
<220> FEATURE:
<223> OTHER INFORMATION: Description of Artificial Sequence: oligo
      ExSalPacF
<220> FEATURE:
<221> NAME/KEY: misc_feature
<222> LOCATION: (1)..(47)

<400> SEQUENCE: 4

```
tcgatggcaa acagctatta tgggtattat gggttcgaat taattaa                  47
```

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence: oligo
      ExSalPacR
<220> FEATURE:
<221> NAME/KEY: misc_feature
<222> LOCATION: (1)..(47)

<400> SEQUENCE: 5

```
tcgattaatt aattcgaacc cataataccc ataatagctg tttgcca                  47
```

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: primer
      PCLIPMSF
<220> FEATURE:
<221> NAME/KEY: misc_feature
<222> LOCATION: (1)..(42)

<400> SEQUENCE: 6

```
ccccaattgg tcgaccatca tcaataatat accttatttt gg                       42
```

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: primer
      pCLIPBSRGI
<220> FEATURE:
<221> NAME/KEY: misc_feature
<222> LOCATION: (1)..(22)

<400> SEQUENCE: 7

```
gcgaaaattg tcacttcctg tg                                             22
```

```
<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: oligo
      Ecolinker+
<220> FEATURE:
<221> NAME/KEY: misc_feature
<222> LOCATION: (1)..(37)

<400> SEQUENCE: 8
aattcggcgc gccgtcgacg atatcgatag cggccgc                              37

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: oligo
      Ecolinker-
<220> FEATURE:
<221> NAME/KEY: misc_feature
<222> LOCATION: (1)..(37)

<400> SEQUENCE: 9
aattgcggcc gctatcgata tcgtcgacgg cgcgccg                              37

<210> SEQ ID NO 10
<211> LENGTH: 49
<212> TYPE: DNA
<213> ORGANISM: Artificial Sequence
<220> FEATURE:
<223> OTHER INFORMATION: Description of Artificial Sequence:
      oligonucleotide HindXba+
<220> FEATURE:
<221> NAME/KEY: misc_feature
<222> LOCATION: (1)..(49)

<400> SEQUENCE: 10
agctctagag gatccgttaa cgctagcgaa ttcaccggta ccaagctta                 49

<210> SEQ ID NO 11
<211> LENGTH: 49
<212> TYPE: DNA
<213> ORGANISM: Artificial Sequence
<220> FEATURE:
<223> OTHER INFORMATION: Description of Artificial Sequence:
      oligonucleotide HindXba-
<220> FEATURE:
<221> NAME/KEY: misc_feature
<222> LOCATION: (1)..(49)

<400> SEQUENCE: 11
ctagtaagct tggtaccggt gaattcgcta gcgttaacgg atcctctag                 49

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: primer 35F1
<220> FEATURE:
<221> NAME/KEY: misc_feature
<222> LOCATION: (1)..(44)

<400> SEQUENCE: 12
cggaattctt aattaatcga catcatcaat aatatacctt atag                      44
```

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: primer 35R2
<220> FEATURE:
<221> NAME/KEY: misc_feature
<222> LOCATION: (1)..(33)

<400> SEQUENCE: 13
ggtggtccta ggctgacacc tacgtaaaaa cag         33

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: primer
      335F3
<220> FEATURE:
<221> NAME/KEY: misc_feature
<222> LOCATION: (1)..(30)

<400> SEQUENCE: 14
tggtggagat ctggtgagta ttgggaaaac         30

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: primer
      435R4
<220> FEATURE:
<221> NAME/KEY: misc_feature
<222> LOCATION: (1)..(37)

<400> SEQUENCE: 15
cggaattctt aattaaggga aatgcaaatc tgtgagg         37

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: primer
      535F5
<220> FEATURE:
<221> NAME/KEY: misc_feature
<222> LOCATION: (1)..(34)

<400> SEQUENCE: 16
cggaattcgc ggccgcggtg agtattggga aaac         34

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: primer
      635R6
<220> FEATURE:
<221> NAME/KEY: misc_feature
<222> LOCATION: (1)..(22)

<400> SEQUENCE: 17
cgccagatcg tctacagaac ag         22

```
<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: primer
      735F7
<220> FEATURE:
<221> NAME/KEY: misc_feature
<222> LOCATION: (1)..(23)

<400> SEQUENCE: 18
gaatgctggc ttcagttgta atc                                              23

<210> SEQ ID NO 19
<211> LENGTH: 42
<212> TYPE: DNA
<213> ORGANISM: Artificial Sequence
<220> FEATURE:
<223> OTHER INFORMATION: Description of Artificial Sequence: primer
      835R8
<220> FEATURE:
<221> NAME/KEY: misc_feature
<222> LOCATION: (1)..(42)

<400> SEQUENCE: 19
cggaattcgc ggccgcattt aaatcatcat caataatata cc                         42

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: primer
      135F11
<220> FEATURE:
<221> NAME/KEY: misc_feature
<222> LOCATION: (1)..(33)

<400> SEQUENCE: 20
ggggtaccga attctcgcta gggtatttat acc                                   33

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: primer
      235F10
<220> FEATURE:
<221> NAME/KEY: misc_feature
<222> LOCATION: (1)..(38)

<400> SEQUENCE: 21
gctctagacc tgcaggttag tcagtttctt ctccactg                              38

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: primer
      3HBV-F
<220> FEATURE:
<221> NAME/KEY: misc_feature
<222> LOCATION: (1)..(27)

<400> SEQUENCE: 22
```

```
ggctctagag atccttcgcg ggacgtc                                              27
```

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: primer
      4HBV-R
<220> FEATURE:
<221> NAME/KEY: misc_feature
<222> LOCATION: (1)..(26)

<400> SEQUENCE: 23

```
ggcgaattca ctgccttcca ccaagc                                               26
```

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence:
      oligonucleotide 1BB1
<220> FEATURE:
<221> NAME/KEY: misc_feature
<222> LOCATION: (1)..(17)

<400> SEQUENCE: 24

```
gtgcctaggc cacgggg                                                         17
```

<210> SEQ ID NO 25
<211> LENGTH: 13
<212> TYPE: DNA
<213> ORGANISM: Artificial Sequence
<220> FEATURE:
<223> OTHER INFORMATION: Description of Artificial Sequence:
      oligonucleotide 2BB2
<220> FEATURE:
<221> NAME/KEY: misc_feature
<222> LOCATION: (1)..(13)

<400> SEQUENCE: 25

```
gtggcctagg cac                                                             13
```

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: primer
      3270F
<220> FEATURE:
<221> NAME/KEY: misc_feature
<222> LOCATION: (1)..(20)

<400> SEQUENCE: 26

```
cacctctgcc taatcatctc                                                      20
```

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: primer
      4270R
<220> FEATURE:
<221> NAME/KEY: misc_feature
<222> LOCATION: (1)..(27)

<400> SEQUENCE: 27

```
gctctagaaa ttccactgcc ttccacc                                27
```

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: primer
      135D21/ 535D21
<220> FEATURE:
<221> NAME/KEY: misc_feature
<222> LOCATION: (1)..(25)

<400> SEQUENCE: 28

```
ttagatccat ggatcccgca gactc                                  25
```

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: primer
      235B3/635B3
<220> FEATURE:
<221> NAME/KEY: misc_feature
<222> LOCATION: (1)..(18)

<400> SEQUENCE: 29

```
cctcagcccc atttccag                                          18
```

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: primer
      15E1A-F
<220> FEATURE:
<221> NAME/KEY: misc_feature
<222> LOCATION: (1)..(20)

<400> SEQUENCE: 30

```
gagacgcccg acatcacctg                                        20
```

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: primer
      25E1B-R
<220> FEATURE:
<221> NAME/KEY: misc_feature
<222> LOCATION: (1)..(26)

<400> SEQUENCE: 31

```
caagcctcca tggggtcaga tgtaac                                 26
```

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: primer
      45AK/5AK
<220> FEATURE:
<221> NAME/KEY: misc_feature
<222> LOCATION: (1)..(21)

```
<400> SEQUENCE: 32
gagcgaagaa acccatctga g                                              21

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: primer
      52155R/2155R
<220> FEATURE:
<221> NAME/KEY: misc_feature
<222> LOCATION: (1)..(19)

<400> SEQUENCE: 33
ggtccaggcc ggctctcgg                                                 19

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: primer
      62155F
<220> FEATURE:
<221> NAME/KEY: misc_feature
<222> LOCATION: (1)..(18)

<400> SEQUENCE: 34
ccgagagccg gcctggac                                                  18

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence: primer
      735F10/35F10
<220> FEATURE:
<221> NAME/KEY: misc_feature
<222> LOCATION: (1)..(38)

<400> SEQUENCE: 35
gctctagacc tgcaggttag tcagtttctt ctccactg                            38

<210> SEQ ID NO 36
<211> LENGTH: 43
<212> TYPE: DNA
<213> ORGANISM: Artificial Sequence
<220> FEATURE:
<223> OTHER INFORMATION: Description of Artificial Sequence: primer
      Bsp-R
<220> FEATURE:
<221> NAME/KEY: misc_feature
<222> LOCATION: (1)..(43)

<400> SEQUENCE: 36
gctctagacc tgcagggtag caacaattcc ggatatttac aag                      43

<210> SEQ ID NO 37
<211> LENGTH: 69
<212> TYPE: DNA
<213> ORGANISM: Artificial Sequence
<220> FEATURE:
<223> OTHER INFORMATION: Description of Artificial Sequence:
      oligonucleotide C2SPA-1
<220> FEATURE:
<221> NAME/KEY: misc_feature
<222> LOCATION: (1)..(69)
```

```
<400> SEQUENCE: 37
ccctgcaggg acttgactca tgcttgtttc actttcacat ggaatttccc agttatgaaa    60
ttaataaag                                                              69

<210> SEQ ID NO 38
<211> LENGTH: 69
<212> TYPE: DNA
<213> ORGANISM: Artificial Sequence
<220> FEATURE:
<223> OTHER INFORMATION: Description of Artificial Sequence:
      oligonucleotide C2SPA-2
<220> FEATURE:
<221> NAME/KEY: misc_feature
<222> LOCATION: (1)..(69)

<400> SEQUENCE: 38
gtctagacac acaaaaaacc aacacactat tgcaatgaaa ataaatttcc tttattaatt    60
tcataactg                                                              69

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: primer
      C2for
<220> FEATURE:
<221> NAME/KEY: misc_feature
<222> LOCATION: (1)..(24)

<400> SEQUENCE: 39
cgggatcccc tgcagggact tgac                                             24

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence: primer
      SPArev
<220> FEATURE:
<221> NAME/KEY: misc_feature
<222> LOCATION: (1)..(31)

<400> SEQUENCE: 40
ttgcgactta agtctagaca cacaaaaaac c                                     31

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: primer
      2155F
<220> FEATURE:
<221> NAME/KEY: misc_feature
<222> LOCATION: (1)..(19)

<400> SEQUENCE: 41
ccgagagccg gcctggacc                                                   19

<210> SEQ ID NO 42
<211> LENGTH: 20
<212> TYPE: DNA
<213> ORGANISM: Artificial Sequence
<220> FEATURE:
```

```
<223> OTHER INFORMATION: Description of Artificial Sequence: primer
      35E3for
<220> FEATURE:
<221> NAME/KEY: misc_feature
<222> LOCATION: (1)..(20)

<400> SEQUENCE: 42
aatgactaat gcaggtgcgc                                                  20

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: primer
      35E3rev
<220> FEATURE:
<221> NAME/KEY: misc_feature
<222> LOCATION: (1)..(28)

<400> SEQUENCE: 43
cgacgcgttg tagtcgttga gcttctag                                         28

<210> SEQ ID NO 44
<211> LENGTH: 34794
<212> TYPE: DNA
<213> ORGANISM: adenoviridae
<220> FEATURE:
<221> NAME/KEY: misc_feature
<222> LOCATION: (1)..(34794)
<223> OTHER INFORMATION: /note="Nucleic acid sequence of Ad 35"

<400> SEQUENCE: 44
catcatcaat aatatacctt atagatggaa tggtgccaat atgtaaatga ggtgatttta      60
aaaagtgtgg gccgtgtggt gattggctgt ggggttaacg gttaaaaggg gcggcgcggc     120
cgtgggaaaa tgacgtttta tggggtggga gttttttttgc aagttgtcgc gggaaatgtt    180
acgcataaaa aggcttcttt tctcacggaa ctacttagtt ttcccacggt atttaacagg     240
aaatgaggta gttttgaccg gatgcaagtg aaaattgctg attttcgcgc gaaaactgaa     300
tgaggaagtg tttttctgaa taatgtggta tttatggcag ggtggagtat ttgttcaggg     360
ccaggtagac tttgacccat tacgtggagg tttcgattac cgtgtttttt acctgaattt     420
ccgcgtaccg tgtcaaagtc ttctgttttt acgtaggtgt cagctgatcg ctagggtatt     480 tataccteag ggtttgtgtc aagaggccac tcttgagtgc cagcgagaag agttttctcc     540
tctgcgccgg cagtttaata ataaaaaaat gagagatttg cgatttctgc ctcaggaaat     600
aatctctgct gagactggaa atgaaatatt ggagcttgtg gtgcacgccc tgatgggaga     660
cgatccggag ccacctgtgc agcttttttga gcctcctacg cttcaggaac tgtatgattt    720
agaggtagag ggatcggagg attctaatga ggaagctgtg aatggctttt ttaccgattc    780 tatgcttttta gctgctaatg aaggattaga attagatccg cctttggaca cttttcaatac  840 tccagggggtg attgtggaaa gcggtacagg tgtaagaaaa ttacctgatt tgagttccgt    900
ggactgtgat ttgcactgct atgaagacgg gtttcctccg agtgatgagg aggaccatga    960
aaaggagcag tccatgcaga ctgcagcggg tgagggagtg aaggctgcca atgttggttt   1020
tcagttggat tgcccggagc ttcctggaca tggctgtaag tcttgtgaat tcacaggaa     1080 aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
```

-continued

```
atctcctgat tctactacct cacctcctga tattcaagca cctgttcctg tggacgtgcg   1320
caagcccatt cctgtgaagc ttaagcctgg gaaacgtcca gcagtggaga acttgagga    1380 cttgttacag ggtggggacg gacctttgga cttgagtaca cggaaacgtc caagacaata   1440
agtgttccat atccgtgttt acttaaggtg acgtcaatat ttgtgtgaga gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagagcgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga cttttttgaag  1800 ctcttaattt gggccatcag gttcacttta agaaaaagt tttatcagtt ttagactttt    1860 caacccccagg tagaactgct gctgctgtgg cttttcttac ttttatatta gataaatgga  1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcca gtggtactga tgctagatct gagttggctt aagtttaat    2280 gagtcgcaga cgtcctgaaa ccatttggtg gcatgaggtt cagaaagagg aagggatga    2340 agtttctgta ttgcaggaga aatattcact ggaacaggtg aaaacatgtt ggttggagcc   2400
agaggatgat tgggcggtgg ccattaaaaa ttatgccaag atagctttga ggcctgataa   2460
acagtataag atcagtagac ggattaatat ccggaatgct tgttacatat ctggaaatgg   2520
ggctgaggtg gtaatagata ctcaagacaa gacagttatt agatgctgca tgatggatat   2580
gtggcctgga gtagtcggta tggaagcagt cactttgta aatgttaagt ttaggggaga    2640
tggttataat ggaatagtgt ttatggccaa taccaaactt atattgcatg gttgtagctt   2700
ttttggtttc aacaataccct gtgtagatgc ctggggacag gttagtgtac ggggggtgtag  2760 tttctatgcg tgttggattg ccacagctgg cagaaccaag agtcaattgt ctctgaagaa   2820
atgcatattc caaagatgta acctgggcat tctgaatgaa ggcgaagcaa gggtccgtca   2880
ctgcgcttct acagatactg gatgttttat tttaattaag ggaaatgcca gcgtaaagca   2940
taacatgatt tgtggtgctt ccgatgagag gccttatcaa atgctcactt gtgctggtgg   3000
gcattgtaat atgctggcta ctgtgcatat tgtttcccat caacgcaaaa aatggcctgt   3060
ttttgatcac aatgtgttga ccaagtgcac catgcatgca ggtgggcgta gaggaatgtt   3120
tatgccttac cagtgtaaca tgaatcatgt gaaagtgttg ttggaaccag atgccttttc   3180
cagaatgagc ctaacaggaa tctttgacat gaacacgcaa atctggaaga tcctgaggta   3240
tgatgatacg agatcgaggg tgcgcgcatg cgaatgcgga ggcaagcatg ccaggttcca   3300
gccggtgtgt gtagatgtga ccgaagatct cagaccggat catttggtta ttgcccgcac   3360
tggagcagag ttcggatcca gtggagaaga aactgactaa ggtgagtatt gggaaaactt   3420
tggggtggga ttttcagatg gacagattga gtaaaaattt gttttttctg tcttgcagct   3480
gacatgagtg gaaatgcttc ttttaagggg ggagtcttca gcccttatct gacagggcgt   3540
ctcccatcct gggcaggagt tcgtcagaat gttatgggat ctactgtgga tggaagaccc   3600
```

```
gttcaacccg ccaattcttc aacgctgacc tatgctactt taagttcttc acctttggac    3660
gcagctgcag ccgctgccgc cgcctctgtc gccgctaaca ctgtgcttgg aatgggttac    3720 tatgaagca tcgtggctaa ttccacttcc tctaataacc cttctacact gactcaggac    3780
aagttacttg tccttttggc ccagctggag gctttgaccc aacgtctggg tgaactttct    3840
cagcaggtgg ccgagttgcg agtacaaact gagtctgctg tcggcacggc aaagtctaaa    3900 taaaaaaat tccagaatca atgaataaat aaacgagctt gttgttgatt taaaatcaag    3960 tgttttatt tcattttcg cgcacggtat gccctggacc accgatctcg atcattgaga    4020
actcggtgga ttttttccag aatcctatag aggtgggatt gaatgtttag atacatgggc    4080
attaggccgt ctttggggtg gagatagctc cattgaaggg attcatgctc cggggtagtg    4140
ttgtaaatca cccagtcata acaaggtcgc agtgcatggt gttgcacaat atcttttaga    4200
agtaggctga ttgccacaga taagcccttg gtgtaggtgt ttacaaaccg gttgagctgg    4260 gagggtgca ttcgaggtga aattatgtgc attttggatt ggattttaa gttggcaata    4320 ttgccgccaa gatcccgtct tgggttcatg ttatgaagga ctaccaagac ggtgtatccg    4380
gtacatttag gaaatttatc gtgcagcttg atggaaaag cgtggaaaaa tttggagaca    4440
cccttgtgtc ctccgagatt ttccatgcac tcatccatga taatagcaat ggggccgtgg    4500
gcagcggcgc gggcaaacac gttccgtggg tctgacacat catagttatg ttcctgagtt    4560
aaatcatcat aagccatttt aatgaatttg gggcggagcg taccagattg gggtatgaat    4620
gttccttcgg gccccggagc atagttcccc tcacagattt gcatttccca agctttcagt    4680
tctgagggtg gaatcatgtc cacctgggg gctatgaaga acaccgtttc ggggcgggg    4740 gtgattagtt gggatgatag caagtttctg agcaattgag atttgccaca tccggtgggg    4800
ccataaataa ttccgattac aggttgcagg tggtagttta gggaacggca actgccgtct    4860
tctcgaagca aggggccac ctcgttcatc atttcccta catgcatatt ttcccgcacc    4920
aaatccatta ggaggcgctc tcctcctagt gatagaagtt cttgtagtga ggaaaagttt    4980
ttcagcggtt ttagaccgtc agccatgggc attttggaaa gagtttgctg caaaagttct    5040
agtctgttcc acagttcagt gatgtgttct atggcatctc gatccagcag acctcctcgt    5100
ttcgcgggtt tggacggctc ctggagtagg gtatgagacg atgggcgtcc agcgctgcca    5160
gggttcggtc cttccagggt ctcagtgttc gagtcagggt tgtttccgtc acagtgaagg    5220
ggtgtgcgcc tgcttgggcg cttgccaggg tgcgcttcag actcattctg ctggtggaga    5280
acttctgtcg cttggcgccc tgtatgtcgg ccaagtagca gtttaccatg agttcgtagt    5340
tgagcgcctc ggctgcgtgg cctttggcgc ggagcttacc tttggaagtt ttcttgcata    5400
ccgggcagta taggcatttc agcgcataca gcttgggcgc aaggaaaatg gattctgggg    5460
agtatgcatc cgcgccgcag gaggcgcaaa cagtttcaca ttccaccagc caggttaaat    5520
ccggttcatt ggggtcaaaa acaagttttc cgccatattt tttgatgcgt ttcttacctt    5580
tggtctccat aagttcgtgt cctcgttgag tgacaaacag gctgtccgta tctccgtaga    5640
ctgattttac aggcctcttc tccagtggag tgcctcggtc ttcttcgtac aggaactctg    5700
accactctga tacaaaggcg cgcgtccagg ccagcacaaa ggaggctatg tgggagggt    5760 agcgatcgtt gtcaaccagg gggtccacct tttccaaagt atgcaaacac atgtcaccct    5820
cttcaacatc caggaatgtg attggcttgt aggtgtattt cacgtgacct ggggtccccg    5880
ctgggggggt ataaaagggg gcggttcttt gctcttcctc actgtcttcc ggatcgctgt    5940
ccaggaacgt cagctgttgg ggtaggtatt ccctctcgaa ggcgggcatg acctctgcac    6000
```

-continued

```
tcaggttgtc agtttctaag aacgaggagg atttgatatt gacagtgccg gttgagatgc      6060 cttttcatgag gttttcgtcc atttggtcag aaaacacaat ttttttattg tcaagtttgg     6120
tggcaaatga tccatacagg gcgttggata aagtttggc aatggatcgc atggtttggt      6180
tcttttcctt gtccgcgcgc tctttggcgg cgatgttgag ttggacatac tcgcgtgcca     6240
ggcacttcca ttcggggaag atagttgtta attcatctgg cacgattctc acttgccacc    6300
ctcgattatg caaggtaatt aaatccacac tggtggccac ctcgcctcga agggttcat     6360 tggtccaaca gagcctacct cctttcctag aacagaaagg gggaagtggg tctagcataa    6420
gttcatcggg agggtctgca tccatggtaa agattcccgg aagtaaatcc ttatcaaaat    6480
agctgatggg agtgggtca tctaaggcca tttgccattc tcgagctgcc agtgcgcgct      6540
catatgggtt aaggggactg ccccagggca tgggatgggt gagagcagag gcatacatgc    6600
cacagatgtc atagacgtag atgggatcct caaagatgcc tatgtaggtt ggatagcatc    6660
gcccccctct gatacttgct cgcacatagt catatagttc atgtgatggc gctagcagcc    6720
ccggacccaa gttggtgcga ttgggttttt ctgttctgta gacgatctgg cgaaagatgg    6780
cgtgagaatt ggaagagatg gtgggtcttt gaaaaatgtt gaaatgggca tgaggtagac    6840
ctacagagtc tctgacaaag tgggcataag attcttgaag cttggttacc agttcggcgg    6900
tgacaagtac gtctagggcg cagtagtcaa gtgtttcttg aatgatgtca taacctggtt    6960 ggttttctt tccccacagt tcgcggttga aaggtattc ttcgcgatcc ttccagtact      7020
cttctagcgg aaacccgtct ttgtctgcac ggtaagatcc tagcatgtag aactgattaa   7080
ctgccttgta agggcagcag cccttctcta cgggtagaga gtatgcttga gcagcttttc    7140
gtagcgaagc gtgagtaagg gcaaaggtgt ctctgaccat gactttgaga aattggtatt   7200
tgaagtccat gtcgtcacag gctccctgtt cccagagttg gaagtctacc cgtttcttgt    7260
aggcggggtt gggcaaagcg aaagtaacat cattgaagag aatcttaccg gctctgggca   7320
taaaattgcg agtgatgcgg aaaggctgtg gtacttccgc tcgattgttg atcacctggg    7380
cagctaggac gatttcgtcg aaaccgttga tgttgtgtcc tacgatgtat aattctatga   7440
aacgcggcgt gcctctgacg tgaggtagct tactgagctc atcaaaggtt aggtctgtgg    7500
ggtcagataa ggcgtagtgt tcgagagccc attcgtgcag gtgaggattt gcatgtagga   7560
atgatgacca aagatctacc gccagtgctg tttgtaactg gtcccgatac tgacgaaaat    7620
gccggccaat tgccattttt tctggagtga cacagtagaa ggttctgggg tcttgttgcc    7680
atcgatccca cttgagttta atggctagat cgtgggccat gttgacgaga cgctcttctc    7740
ctgagagttt catgaccagc atgaaaggaa ctagttgttt gccaaaggat cccatccagg    7800
tgtaagtttc cacatcgtag gtcaggaaga gtctttctgt gcgaggatga gagccgatcg    7860
ggaagaactg gatttcctgc caccagttgg aggattggct gttgatgtga tggaagtaga    7920
agtttctgcg gcgcgccgag cattcgtgtt tgtgcttgta cagacggccg cagtagtcgc    7980
agcgttgcac gggttgtatc tcgtgaatga gctgtacctg gcttcccttg acgagaaatt    8040
tcagtgggaa gccgaggcct ggcgattgta tctcgtgctc ttctatattc gctgtatcgg   8100
cctgttcatc ttctgtttcg atggtggtca tgctgacgag ccccgcgggg aggcaagtcc    8160
agacctcggc gcgggagggg cggagctgaa ggacgagagc gcgcaggctg gagctgtcca   8220
gagtcctgag acgctgcgga ctcaggttag taggtaggga cagaagatta acttgcatga   8280
tcttttccag ggcgtgcggg aggttcagat ggtacttgat ttccacaggt tcgtttgtag   8340
```

```
agacgtcaat ggcttgcagg gttccgtgtc ctttgggcgc cactaccgta cctttgtttt      8400
ttcttttgat cggtggtggc tctcttgctt cttgcatgct cagaagcggt gacgggacg       8460 cgcgccgggc ggcagcggtt gttccggacc cggggggcatg gctggtagtg gcacgtcggc    8520
gccgcgcacg ggcaggttct ggtattgcgc tctgagaaga cttgcgtgcg ccaccacgcg      8580
tcgattgacg tcttgtatct gacgtctctg ggtgaaagct accggccccg tgagcttgaa      8640
cctgaaagag agttcaacag aatcaatttc ggtatcgtta acggcagctt gtctcagtat      8700
ttcttgtacg tcaccagagt tgtcctggta ggcgatctcc gccatgaact gctcgatttc      8760
ttcctcctga agatctccgc gacccgctct ttcgacggtg gccgcgaggt cattggagat      8820
acggcccatg agttgggaga atgcattcat gcccgcctcg ttccagacgc ggctgtaaac      8880
cacggccccc tcggagtctc ttgcgcgcat caccacctga gcgaggttaa gctccacgtg      8940
tctggtgaag accgcatagt tgcataggcg ctgaaaaagg tagttgagtg tggtggcaat     9000
gtgttcggcg acgaagaaat acatgatcca tcgtctcagc ggcatttcgc taacatcgcc      9060
cagagcttcc aagcgctcca tggcctcgta gaagtccacg gcaaaattaa aaaactggga     9120
gtttcgcgcg gacacggtca attcctcctc gagaagacgg atgagttcgg ctatggtggc      9180
ccgtacttcg cgttcgaagg ctcccgggat ctcttcttcc tcttctatct cttcttccac      9240
taacatctct tcttcgtctt caggcggggg cggaggggc acgcggcgac gtcgacggcg       9300
cacgggcaaa cggtcgatga atcgttcaat gacctctccg cggcggcggc gcatggtttc     9360
agtgacggcg cggccgttct cgcgcggtcg cagagtaaaa acaccgccgc gcatctcctt      9420
aaagtggtga ctgggaggtt ctccgtttgg gagggagagg gcgctgatta tacattttat     9480
taattggccc gtagggactg cgcgcagaga tctgatcgtg tcaagatcca cgggatctga     9540
aaacctttcg acgaaagcgt ctaaccagtc acagtcacaa ggtaggctga gtacggcttc     9600
ttgtgggcgg gggtggttat gtgttcggtc tgggtcttct gtttcttctt catctcggga     9660
aggtgagacg atgctgctgg tgatgaaatt aaagtaggca gttctaagac ggcggatggt     9720
ggcgaggagc accaggtctt tgggtccggc ttgctggata cgcaggcgat tggccattcc     9780
ccaagcatta tcctgacatc tagcaagatc tttgtagtag tcttgcatga gccgttctac     9840
gggcacttct tcctcacccg ttctgccatg catacgtgtg agtccaaatc cgcgcattgg     9900
ttgtaccagt gccaagtcag ctacgactct ttcggcgagg atggcttgct gtacttgggt     9960
aagggtggct tgaaagtcat caaaatccac aaagcggtgg taagcccctg tattaatggt    10020
gtaagcacag ttggccatga ctgaccagtt aactgtctgg tgaccagggc gcacgagctc     10080
ggtgtattta aggcgcgaat aggcgcgggt gtcaaagatg taatcgttgc aggtgcgcac    10140
cagatactgg taccctataa gaaaatgcgg cggtggttgg cggtagagag gccatcgttc    10200
tgtagctgga gcgccagggg cgaggtcttc caacataagg cggtgatagc cgtagatgta    10260
cctggacatc caggtgattc ctgcggcggt agtagaagcc cgaggaaact cgcgtacgcg    10320
gttccaaatg ttgcgtagcg gcatgaagta gttcattgta ggcacggttt gaccagtgag    10380
gcgcgcgcag tcattgatgc tctatagaca cggagaaaat gaaagcgttc agcgactcga    10440
ctccgtagcc tggaggaacg tgaacgggtt gggtcgcggt gtaccccggt tcgagacttg     10500
tactcgagcc ggccggagcc gcggctaacg tggtattggc actcccgtct cgacccagcc     10560
tacaaaaatc caggatacgg aatcgagtcg ttttgctggt ttccgaatgg cagggaagtg    10620
agtcctattt ttttttttt tttgccgctc agatgcatcc cgtgctgcga cagatgcgcc     10680
cccaacaaca gcccccctcg cagcagcagc agcagcaacc acaaaaggct gtccctgcaa     10740
```

```
ctactgcaac tgccgccgtg agcggtgcgg gacagcccgc ctatgatctg gacttggaag    10800
agggcgaagg actggcacgt ctaggtgcgc cttcgcccga gcggcatccg cgagttcaac    10860
tgaaaaaaga ttctcgcgag gcgtatgtgc cccaacagaa cctatttaga gacagaagcg    10920
gcgaggagcc ggaggagatg cgagcttccc gctttaacgc gggtcgtgag ctgcgtcacg    10980
gtttggaccg aagacgagtg ttgcgagacg aggatttcga agttgatgaa gtgacaggga    11040
tcagtcctgc cagggcacac gtggctgcag ccaaccttgt atcggcttac gagcagacag    11100
taaaggaaga gcgtaacttc caaaagtctt ttaataatca tgtgcgaacc ctgattgccc    11160
gcgaagaagt taccctttggt ttgatgcatt tgtgggattt gatggaagct atcattcaga    11220
accctactag caaacctctg accgcccagc tgtttctggt ggtgcaacac agcagagaca    11280
atgaggcttt cagagaggcg ctgctgaaca tcaccgaacc cgaggggaga tggttgtatg    11340
atcttatcaa cattctacag agtatcatag tgcaggagcg gagcctgggc ctggccgaga    11400
aggtagctgc catcaattac tcggttttga gcttgggaaa atattacgct cgcaaaatct    11460
acaagactcc atacgttccc atagacaagg aggtgaagat agatgggttc tacatgcgca    11520
tgacgctcaa ggtcttgacc ctgagcgatg atcttggggt gtatcgcaat gacagaatgc    11580
atcgcgcggt tagcgccagc aggaggcgcg agttaagcga cagggaactg atgcacagtt    11640
tgcaaagagc tctgactgga gctggaaccg agggtgagaa ttacttcgac atgggagctg    11700
acttgcagtg gcagcctagt cgcagggctc tgagcgccgc gacggcagga tgtgagcttc    11760
cttacataga agaggcggat gaaggcgagg aggaagaggg cgagtacttg gaagactgat    11820
ggcacaaccc gtgttttttg ctagatggaa cagcaagcac cggatcccgc aatgcgggcg    11880
gcgctgcaga gccagccgtc cggcattaac tcctcggacg attggaccca ggccatgcaa    11940
cgtatcatgg cgttgacgac tcgcaacccc gaagccttta gacagcaacc ccaggccaac    12000
cgtctatcgg ccatcatgga agctgtagtg ccttcccgat ctaatcccac tcatgagaag    12060
gtcctggcca tcgtgaacgc gttggtggag aacaaagcta ttcgtccaga tgaggccgga    12120
ctggtataca acgctctctt agaacgcgtg gctcgctaca acagtagcaa tgtgcaaacc    12180
aatttggacc gtatgataac agatgtacgc gaagccgtgt ctcagcgcga aaggttccag    12240
cgtgatgcca acctgggttc gctggtggcg ttaaatgctt tcttgagtac tcagcctgct    12300
aatgtgccgc gtggtcaaca ggattatact aacttttaa gtgctttgag actgatggta    12360
tcagaagtac ctcagagcga agtgtatcag tccggtcctg attacttctt tcagactagc    12420
agacagggct tgcagacggt aaatctgagc caagctttta aaaaccttaa aggtttgtgg    12480
ggagtgcatg ccccggtagg agaaagagca accgtgtcta gcttgttaac tccgaactcc    12540
cgcctgttat tactgttggt agctccttc accgacagcg gtagcatcga ccgtaattcc    12600
tatttgggtt acctactaaa cctgtatcgc gaagccatag gcaaagtca ggtggacgag    12660
cagacctatc aagaaattac ccaagtcagt cgcgctttgg gacaggaaga cactggcagt    12720
ttggaagcca ctctgaactt cttgcttacc aatcggtctc aaaagatccc tcctcaatat    12780
gctcttactg cggaggagga gaggatcctt agatatgtgc agcagagcgt gggattgttt    12840
ctgatgcaag aggggcaac tccgactgca gcactggaca tgacagcgcg aaatatggag    12900
cccagcatgt atgccagtaa ccgaccttc attaacaaac tgctggacta cttgcacaga    12960
gctgccgcta tgaactctga ttatttcacc aatgccatct aaacccgca ctggctgccc    13020
ccacctggtt tctacacggg cgaatatgac atgcccgacc ctaatgacgg atttctgtgg    13080
```

```
gacgacgtgg acagcgatgt tttttcacct ctttctgatc atcgcacgtg gaaaaaggaa   13140
ggcggtgata gaatgcattc ttctgcatcg ctgtccgggg tcatgggtgc taccgcggct   13200
gagcccgagt ctgcaagtcc ttttcctagt ctaccctttt ctctacacag tgtacgtagc   13260
agcgaagtgg gtagaataag tcgcccgagt ttaatgggcg aagaggagta cctaaacgat   13320
tccttgctca gaccggcaag agaaaaaaat ttcccaaaca atggaataga aagtttggtg   13380
gataaaatga gtagatggaa gacttatgct caggatcaca gagacgagcc tgggatcatg   13440
gggactacaa gtagagcgag ccgtagacgc cagcgccatg acagacagag gggtcttgtg   13500
tgggacgatg aggattcggc cgatgatagc agcgtgttgg acttgggtgg gagaggaagg   13560
ggcaacccgt ttgctcattt cgcccctcgc ttgggtggta tgttgtgaaa aaaaataaaa   13620
aagaaaaact caccaaggcc atggcgacga gcgtacgttc gttcttcttt attatctgtg   13680
tctagtataa tgaggcgagt cgtgctaggc ggagcggtgg tgtatccgga gggtcctcct   13740
ccttcgtacg agagcgtgat gcagcagcag caggcgacgg cggtgatgca atccccactg   13800
gaggctccct ttgtgcctcc gcgatacctg gcacctacgg agggcagaaa cagcattcgt   13860
tactcggaac tggcacctca gtacgatacc accaggttgt atctggtgga caacaagtcg   13920
gcggacattg cttctctgaa ctatcagaat gaccacagca acttcttgac cacggtggtg   13980
cagaacaatg actttacccc tacggaagcc agcacccaga ccattaactt tgatgaacga   14040
tcgcggtggg gcggtcagct aaagaccatc atgcatacta acatgccaaa cgtgaacgag   14100
tatatgttta gtaacaagtt caaagcgcgt gtgatggtgt ccagaaaacc tcccgacggt   14160
gctgcagttg gggatactta tgatcacaag caggatattt tggaatatga gtggttcgag   14220
tttactttgc cagaaggcaa cttttcagtt actatgacta ttgatttgat gaacaatgcc   14280
atcatagata attacttgaa agtgggtaga cagaatggag tgcttgaaag tgacattggt   14340
gttaagttcg acaccaggaa cttcaagctg ggatgggatc ccgaaaccaa gttgatcatg   14400
cctggagtgt atacgtatga agccttccat cctgacattg tcttactgcc tggctgcgga   14460
gtggatttta ccgagagtcg tttgagcaac cttcttggta tcagaaaaaa acagccattt   14520
caagagggtt ttaagatttt gtatgaagat ttagaaggtg gtaatattcc ggccctcttg   14580
gatgtagatg cctatgagaa cagtaagaaa gaacaaaaag ccaaaataga agctgctaca   14640
gctgctgcag aagctaaggc aaacatagtt gccagcgact ctacaagggt tgctaacgct   14700
ggagaggtca gaggagacaa ttttgcgcca acacctgttc cgactgcaga atcattattg   14760
gccgatgtgt ctgaaggaac ggacgtgaaa ctcactattc aacctgtaga aaaagatagt   14820
aagaatagaa gctataatgt gttggaagac aaaatcaaca cagcctatcg cagttggtat   14880
ctttcgtaca attatggcga tcccgaaaaa ggagtgcgtt cctggacatt gctcaccacc   14940
tcagatgtca cctgcggagc agagcaggtt tactggtcgc ttccagacat gatgaaggat   15000
cctgtcactt tccgctccac tagacaagtc agtaactacc ctgtggtggg tgcagagctt   15060
atgcccgtct tctcaaagag cttctacaac gaacaagctg tgtactccca gcagctccgc   15120
cagtccacct cgcttacgca cgtcttcaac cgctttcctg agaaccagat tttaatccgt   15180
ccgccggcgc ccaccattac caccgtcagt gaaaacgttc ctgctctcac agatcacggg   15240
accctgccgt tgcgcagcag tatccgggga gtccaacgtg tgaccgttac tgacgccaga   15300
cgccgcacct gtccctacgt gtacaaggca ctgggcatag tcgtaccgcg cgtccttca   15360
agccgcactt tctaaaaaaa aaaaatgtcc attcttatct cgcccagtaa taacaccggt   15420
tggggtctgc gcgctccaag caagatgtac ggaggcgcac gcaaacgttc tacccaacat   15480
```

-continued

```
cccgtgcgtg ttcgcggaca ttttcgcgct ccatggggtg ccctcaaggg ccgcactcgc    15540
gttcgaacca ccgtcgatga tgtaatcgat caggtggttg ccgacgcccg taattatact    15600
cctactgcgc ctacatctac tgtggatgca gttattgaca gtgtagtggc tgacgctcgc    15660
aactatgctc gacgtaagag ccggcgaagg cgcattgcca gacgccaccg agctaccact    15720
gccatgcgag ccgcaagagc tctgctacga agagctagac gcgtggggcg aagagccatg    15780
cttagggcgg ccagacgtgc agcttcgggc gccagcgccg gcaggtcccg caggcaagca    15840
gccgctgtcg cagcggcgac tattgccgac atggcccaat cgcgaagagg caatgtatac    15900
tgggtgcgtg acgctgccac cggtcaacgt gtacccgtgc gcacccgtcc ccctcgcact    15960
tagaagatac tgagcagtct ccgatgttgt gtcccagcgg cgaggatgtc caagcgcaaa    16020
tacaaggaag aaatgctgca ggttatcgca cctgaagtct acggccaacc gttgaaggat    16080
gaaaaaaaac cccgcaaaat caagcgggtt aaaaaggaca aaaaagaaga ggaagatggc    16140
gatgatgggc tggcggagtt tgtgcgcgag tttgccccac ggcgacgcgt gcaatggcgt    16200
gggcgcaaag ttcgacatgt gttgagacct ggaacttcgg tggtctttac acccggcgag    16260
cgttcaagcg ctacttttaa gcgttcctat gatgaggtgt acgggatga tgatattctt    16320 gagcaggcgg ctgaccgatt aggcgagttt gcttatggca agcgtagtag aataacttcc    16380
aaggatgaga cagtgtcaat acccttggat catggaaatc ccaccctag tcttaaaccg    16440 gtcactttgc agcaagtgtt acccgtaact ccgcgaacag gtgttaaacg cgaaggtgaa    16500
gatttgtatc ccactatgca actgatggta cccaaacgcc agaagttgga ggacgttttg    16560
gagaaagtaa aagtggatcc agatattcaa cctgaggtta aagtgagacc cattaagcag    16620
gtagcgcctg gtctgggggt acaaactgta gacattaaga ttcccactga agtatgaaa    16680 gtgcaaactg aacccgcaaa gcctactgcc acctccactg aagtgcaaac ggatccatgg    16740
atgcccatgc ctattacaac tgacgccgcc ggtcccactc gaagatcccg acgaaagtac    16800
ggtccagcaa gtctgttgat gcccaattat gttgtacacc catctattat tcctactcct    16860
ggttaccgag gcactcgcta ctatcgcagc cgaaacagta cctcccgccg tcgccgcaag    16920
acacctgcaa atcgcagtcg tcgccgtaga cgcacaagca aaccgactcc cggcgccctg    16980
gtgcggcaag tgtaccgcaa tggtagtgcg gaacctttga cactgccgcg tgcgcgttac    17040
catccgagta tcatcactta atcaatgttg ccgctgcctc cttgcagata tggccctcac    17100
ttgtcgcctt cgcgttccca tcactggtta ccgaggaaga aactcgcgcc gtagaagagg    17160
gatgttggga cgcggaatgc gacgctacag gcgacggcgt gctatccgca agcaattgcg    17220
gggtggtttt ttaccagcct taattccaat tatcgctgct gcaattggcg cgataccagg    17280
catagcttcc gtggcggttc aggcctcgca acgacattga cattggaaaa aaaacgtata    17340
aataaaaaaa aatacaatgg actctgacac tcctggtcct gtgactatgt tttcttagag    17400
atggaagaca tcaattttc atccttggct ccgcgacacg gcacgaagcc gtacatgggc    17460
acctggagcg acatcggcac gagccaactg aacgggggcg ccttcaattg gagcagtatc    17520
tggagcgggc ttaaaaattt tggctcaacc ataaaaacat acgggaacaa agcttggaac    17580
agcagtacag gacaggcgct tagaaataaa cttaaagacc agaacttcca acaaaaagta    17640
gtcgatggga tagcttccgg catcaatgga gtggtagatt tggctaacca ggctgtgcag    17700
aaaaagataa acagtcgttt ggacccgccg ccagcaaccc caggtgaaat gcaagtggag    17760
gaagaaattc ctccgccaga aaaacgaggc gacaagcgtc cgcgtcccga tttggaagag    17820
```

```
acgctggtga cgcgcgtaga tgaaccgcct tcttatgagg aagcaacgaa gcttggaatg    17880
cccaccacta gaccgatagc cccaatggcc accggggtga tgaaaccttc tcagttgcat    17940
cgacccgtca ccttggattt gcccccteee cctgctgcta ctgctgtacc cgcttctaag    18000
cctgtcgctg ccccgaaacc agtcgccgta gccaggtcac gtcccggggg cgctcctcgt    18060
ccaaatgcgc actggcaaaa tactctgaac agcatcgtgg gtctaggcgt gcaaagtgta    18120
aaacgccgtc gctgctttta attaaatatg gagtagcgct taacttgcct atctgtgtat    18180
atgtgtcatt acacgccgtc acagcagcag aggaaaaaag gaagaggtcg tgcgtcgacg    18240
ctgagttact ttcaagatgg ccaccccatc gatgctgccc caatgggcat acatgcacat    18300
cgccggacag gatgcttcgg agtacctgag tccgggtctg gtgcagttcg cccgcgccac    18360
agacacctac ttcaatctgg gaataagtt tagaaatccc accgtagcgc cgacccacga    18420
tgtgaccacc gaccgtagcc agcggctcat gttgcgcttc gtgcccgttg accgggagga    18480
caatacatac tcttacaaag tgcggtacac cctggccgtg ggcgacaaca gagtgctgga    18540
tatggccagc acgttctttg acattagggg cgtgttggac agaggtccca gtttcaaacc    18600
ctattctggt acggcttaca actctctggc tcctaaaggc gctccaaatg catctcaatg    18660
gattgcaaaa ggcgtaccaa ctgcagcagc cgcaggcaat ggtgaagaag aacatgaaac    18720
agaggagaaa actgctactt cacttttgc caatgctcct gtaaaagccg aggctcaaat    18780
tacaaaagag ggcttaccaa taggtttgga gatttcagct gaaaacgaat ctaaacccat    18840
ctatgcagat aaactttatc agccagaacc tcaagtggga gatgaaactt ggactgacct    18900
agacggaaaa accgaagagt atggaggcag ggctctaaag cctactacta acatgaaacc    18960
ctgttacggg tcctatgcga agcctactaa ttaaaaggt ggtcaggcaa aaccgaaaaa    19020
ctcggaaccg tcgagtgaaa aaattgaata tgatattgac atggaatttt ttgataactc    19080
atcgcaaaga acaaacttca gtcctaaaat tgtcatgtat gcagaaaatg taggtttgga    19140
aacgccagac actcatgtag tgtacaaacc tggaacagaa gacacaagtt ccgaagctaa    19200
tttgggacaa cagtctatgc ccaacagacc caactacatt ggcttcagag ataacttat    19260
tggactcatg tactataaca gtactggtaa catgggggtg ctggctggtc aagcgtctca    19320
gttaaatgca gtggttgact tgcaggacag aaacacagaa cttcttacc aactcttgct    19380
tgactctctg ggcgacagaa ccagatactt tagcatgtgg aatcaggctg tggacagtta    19440
tgatcctgat gtacgtgtta ttgaaaatca tggtgtggaa gatgaacttc ccaactattg    19500
ttttccactg gacggcatag gtgttccaac aaccagttac aaatcaatag ttccaaatgg    19560
agaagataat aataattgga agaacctga agtaaatgga acaagtgaga tcggacaggg    19620
taatttgttt gccatggaaa ttaaccttca gccaatctca tggcgaagtt tcctttattc    19680
caatgtggct ctgtatctcc cagactcgta caaatacacc ccgtccaatg tcactcttcc    19740
agaaaacaaa aacacctacg actacatgaa cgggcgggtg gtgccgccat ctctagtaga    19800
cacctatgtg aacattggtg ccaggtggtc tctggatgcc atggacaatg tcaacccatt    19860
caaccaccac cgtaacgctg gcttgcgtta ccgatctatg cttctgggta acggacgtta    19920
tgtgcctttc cacatacaag tgcctcaaaa attcttcgct gttaaaaacc tgctgcttct    19980
cccaggctcc tacacttatg agtggaactt taggaaggat gtgaacatgg ttctacagag    20040
ttccctcggt aacgacctgc gggtagatgg cgccagcatc agtttcacga gcatcaacct    20100
ctatgctact tttttccca tggctcacaa caccgcttcc acccttgaag ccatgctgcg    20160
gaatgacacc aatgatcagt cattcaacga ctacctatct gcagctaaca tgctctaccc    20220
```

```
cattcctgcc aatgcaacca atattcccat ttccattcct tctcgcaact gggcggcttt    20280
cagaggctgg tcatttacca gactgaaaac caaagaaact ccctctttgg ggtctggatt    20340 tgaccectac tttgtctatt ctggttctat tccctacctg gatggtacct tctacctgaa    20400
ccacactttt aagaaggttt ccatcatgtt tgactcttca gtgagctggc ctggaaatga    20460
caggttacta tctcctaacg aatttgaaat aaagcgcact gtggatggcg aaggctacaa    20520
cgtagcccaa tgcaacatga ccaaagactg gttcttggta cagatgctcg ccaactacaa    20580
catcggctat cagggcttct acattccaga aggatacaaa gatcgcatgt attcattttt    20640
cagaaacttc cagcccatga gcaggcaggt ggttgatgag gtcaattaca aagacttcaa    20700
ggccgtcgcc atacctacc aacacaacaa ctctggcttt gtgggttaca tggctccgac    20760
catgcgccaa ggtcaaccct atcccgctaa ctatccctat ccactcattg aacaactgc    20820 cgtaaatagt gttacgcaga aaagttctt gtgtgacaga accatgtggc gcataccgtt    20880
ctcgagcaac ttcatgtcta tgggggccct tacagacttg ggacagaata tgctctatgc    20940
caactcagct catgctctgg acatgaccttt gaggtggat cccatggatg agcccaccct    21000
gctttatctt ctcttcgaag ttttcgacgt ggtcagagtg catcagccac accgcggcat    21060
catcgaggca gtctacctgc gtacaccgtt ccggccggt aacgctacca cgtaagaagc    21120
ttcttgcttc ttgcaaatag cagctgcaac catggcctgc ggatcccaaa acggctccag    21180
cgagcaagag ctcagagcca ttgtccaaga cctgggttgc ggaccctatt ttttgggaac    21240
ctacgataag cgcttcccgg ggttcatggc ccccgataag ctcgcctgtg ccattgtaaa    21300
tacggccgga cgtgagacgg ggggagagca ctggttggct ttcggttgga acccacgttc    21360
taacacctgc tacctttttg atccttttgg attctcggat gatcgtctca aacagattta    21420
ccagtttgaa tatgagggtc tcctgcgccg cagcgctctt gctaccaagg accgctgtat    21480
tacgctggaa aaatctaccc agaccgtgca gggcccccgt tctgccgcct gcggacttttt    21540 ctgctgcatg ttccttcacg cctttgtgca ctggcctgac cgtcccatgg acggaaaccc    21600
caccatgaaa ttgctaactg gagtgccaaa caacatgctt cattctccta aagtccagcc    21660
caccctgtgt gacaatcaaa agcactcta ccattttctt aatacccatt cgccttattt    21720
tcgctctcat cgtacacaca tcgaaagggc cactgcgttc gaccgtatgg atgttcaata    21780
atgactcatg taaacaacgt gttcaataaa catcacttta tttttttaca tgtatcaagg    21840
ctctggatta cttatttatt tacaagtcga atgggttctg acgagaatca gaatgacccg    21900
caggcagtga tacgttgcgg aactgatact tgggttgcca cttgaattcg ggaatcacca    21960
acttgggaac cggtatatcg ggcaggatgt cactccacag ctttctggtc agctgcaaag    22020
ctccaagcag gtcaggagcc gaaatcttga aatcacaatt aggaccagtg ctctgagcgc    22080
gagagttgcg gtacaccgga ttgcagcact gaaacaccat cagcgacgga tgtctcacgc    22140
ttgccagcac ggtgggatct gcaatcatgc ccacatccag atcttcagca ttggcaatgc    22200 tgaacgggt catcttgcag gtctgcctac ccatggcggg cacccaatta ggcttgtggt    22260
tgcaatcgca gtgcaggggg atcagtatca tcttggcctg atcctgtctg attcctggat    22320
acacggctct catgaaagca tcatattgct tgaaagcctg ctgggcttta ctaccctcgg    22380
tataaaacat cccgcaggac ctgctcgaaa actggttagc tgcacagccg gcatcattca    22440
cacagcagcg ggcgtcattg ttggctattt gcaccacact tctgcccag cggttttggg    22500 tgattttggt tcgctcggga ttctccttta aggctcgttg tccgttctcg ctggccacat    22560
```

-continued

| | |
|---|---|
| ccatctcgat aatctgctcc ttctgaatca taatattgcc atgcaggcac ttcagcttgc | 22620 |
| cctcataatc attgcagcca tgaggccaca acgcacagcc tgtacattcc caattatggt | 22680 |
| gggcgatctg agaaaaagaa tgtatcattc cctgcagaaa tcttcccatc atcgtgctca | 22740 |
| gtgtcttgtg actagtgaaa gttaactgga tgcctcggtg ctcttcgttt acgtactggt | 22800 |
| gacagatgcg cttgtattgt tcgtgttgct caggcattag tttaaaacag gttctaagtt | 22860 |
| cgttatccag cctgtacttc tccatcagca gacacatcac ttccatgcct ttctcccaag | 22920 |
| cagacaccag gggcaagcta atcggattct taacagtgca ggcagcagct cctttagcca | 22980 |
| gagggtcatc tttagcgatc ttctcaatgc ttcttttgcc atccttctca acgatgcgca | 23040 |
| cgggcgggta gctgaaaccc actgctacaa gttgcgcctc ttctctttct tcttcgctgt | 23100 |
| cttgactgat gtcttgcatg gggatatgtt tggtcttcct tggcttcttt ttggggggta | 23160 |
| tcggaggagg aggactgtcg ctccgttccg gagacaggga ggattgtgac gtttcgctca | 23220 |
| ccattaccaa ctgactgtcg gtagaagaac ctgaccccac acggcgacag gtgtttttct | 23280 |
| tcggggggcag aggtggaggc gattgcgaag ggctgcggtc cgacctggaa ggcggatgac | 23340 |
| tggcagaacc ccttccgcgt tcggggggtgt gctccctgtg gcggtcgctt aactgatttc | 23400 |
| cttcgcggct ggccattgtg ttctcctagg cagagaaaca acagacatgg aaactcagcc | 23460 |
| attgctgtca acatcgccac gagtgccatc acatctcgtc ctcagcgacg aggaaaagga | 23520 |
| gcagagctta agcattccac cgcccagtcc tgccaccacc tctaccctag aagataagga | 23580 |
| ggtcgacgca tctcatgaca tgcagaataa aaaagcgaaa gagtctgaga cagacatcga | 23640 |
| gcaagacccg ggctatgtga caccggtgga acacgaggaa gagttgaaac gctttctaga | 23700 |
| gagagaggat gaaaactgcc caaaacagcg agcagataac tatcaccaag atgctggaaa | 23760 |
| tagggatcag aacaccgact acctcatagg gcttgacggg gaagacgcgc tccttaaaca | 23820 |
| tctagcaaga cagtcgctca tagtcaagga tgcattattg gacagaactg aagtgcccat | 23880 |
| cagtgtggaa gagctcagct gcgcctacga gcttaacctt ttttcacctc gtactccccc | 23940 |
| caaacgtcag ccaaacggca cctgcgagcc aaatcctcgc ttaaactttt atccagcttt | 24000 |
| tgctgtgcca gaagtactgg ctacctatca catcttttt aaaaatcaaa aaattccagt | 24060 |
| ctcctgccgc gctaatcgca cccgcgccga tgccctactc aatctgggac ctggttcacg | 24120 |
| cttacctgat atagcttcct tggaagaggt tccaaagatc ttcgagggtc tgggcaataa | 24180 |
| tgagactcgg gccgcaaatg ctctgcaaaa gggagaaaat ggcatggatg agcatcacag | 24240 |
| cgttctggtg gaattggaag gcgataatgc cagactcgca gtactcaagc gaagcgtcga | 24300 |
| ggtcacacac ttcgcatatc ccgctgtcaa cctgccccct aaagtcatga cggcggtcat | 24360 |
| ggaccagtta ctcattaagc gcgcaagtcc cctttcagaa gacatgcatg acccagatgc | 24420 |
| ctgtgatgag ggtaaaccag tggtcagtga tgagcagcta acccgatggc tgggcaccga | 24480 |
| ctctccccgg gatttggaag agcgtcgcaa gcttatgatg gccgtggtgc tggttaccgt | 24540 |
| agaactagag tgtctccgac gtttctttac cgattcagaa accttgcgca aactcgaaga | 24600 |
| gaatctgcac tacacttttta gacacggctt tgtgcggcag gcatgcaaga tatctaacgt | 24660 |
| ggaactcacc aacctggttt cctacatggg tattctgcat gagaatcgcc taggacaaag | 24720 |
| cgtgctgcac agcacccta aggggggaagc ccgccgtgat tacatccgcg attgtgtcta | 24780 |
| tctctacctg tgccacacgt ggcaaaccgg catgggtgta tggcagcaat gtttagaaga | 24840 |
| acagaacttg aaagagcttg acaagctctt acagaaatct cttaaggttc tgtggacagg | 24900 |
| gttcgacgag cgcaccgtcg cttccgacct ggcagacctc atcttcccag agcgtctcag | 24960 |

```
ggttactttg cgaaacggat tgcctgactt tatgagccag agcatgctta acaattttcg   25020
ctctttcatc ctggaacgct ccggtatcct gcccgccacc tgctgcgcac tgccctccga   25080
ctttgtgcct ctcacctacc gcgagtgccc ccgccgcta tggagtcact gctacctgtt    25140
ccgtctggcc aactatctct cctaccactc ggatgtgatc gaggatgtga gcggagacgg   25200
cttgctggag tgccactgcc gctgcaatct gtgcacgccc caccggtccc tagcttgcaa   25260
cccccagttg atgagcgaaa cccagataat aggcaccttt gaattgcaag ccccagcag    25320
ccaaggcgat gggtcttctc ctgggcaaag tttaaaactg accccgggac tgtggacctc   25380
cgcctacttg cgcaagtttg ctccggaaga ttaccacccc tatgaaatca gttctatga    25440
ggaccaatca cagcctccaa aggccgaact ttcggcttgc gtcatcaccc aggggcaat    25500
tctggcccaa ttgcaagcca tccaaaaatc ccgccaagaa tttctactga aaagggtaa    25560
gggggtctac cttgaccccc agaccggcga ggaactcaac acaaggttcc ctcaggatgt   25620
cccaacgacg agaaaacaag aagttgaagg tgcagccgcc gcccccagaa gatatggagg   25680
aagattggga cagtcaggca gaggaggcgg aggaggacag tctggaggac agtctggagg   25740
aagacagttt ggaggaggaa aacgaggagg cagaggaggt ggaagaagta accgccgaca   25800
aacagttatc ctcggctgcg gagacaagca acagcgctac catctccgct ccgagtcgag   25860
gaacccggcg gcgtcccagc agtagatggg acgagaccgg acgcttcccg aacccaacca   25920
gcgcttccaa gaccggtaag aaggatcggc agggatacaa gtcctggcgg gggcataaga   25980
atgccatcat ctcctgcttg catgagtgcg ggggcaacat atccttcacg cggcgctact   26040
tgctattcca ccatggggtg aactttccgc gcaatgtttt gcattactac cgtcacctcc   26100
acagccccta ctatagccag caaatcccga cagtctcgac agataaagac agcggcggcg   26160
acctccaaca gaaaccagc agcggcagtt agaaaataca caacaagtgc agcaacagga    26220
ggattaaaga ttacagccaa cgagccagcg caaacccgag agttaagaaa tcggatcttt   26280
ccaaccctgt atgccatctt ccagcagagt cggggtcaag agcaggaact gaaaataaaa   26340
aaccgatctc tgcgttcgct caccagaagt tgtttgtatc acaagagcga agatcaactt   26400
cagcgcactc tcgaggacgc cgaggctctc ttcaacaagt actgcgcgct gactcttaaa   26460
gagtaggcag cgaccgcgct tattcaaaaa aggcgggaat tacatcatcc tcgacatgag   26520
taaagaaatt cccacgcctt acatgtggag ttatcaaccc caaatgggat tggcagcagg   26580
cgcctcccag gactactcca cccgcatgaa ttggctcagc gccgggcctt ctatgatttc   26640
tcgagttaat gatatacgcg cctaccgaaa ccaaatactt ttggaacagt cagctcttac   26700
caccacgccc cgccaacacc ttaatcccag aaattggccc gccgcctag tgtaccagga    26760
aagtcccgct cccaccactg tattacttcc tcgagacgcc caggccgaag tccaaatgac   26820
taatgcaggt gcgcagttag ctggcggctc caccctatgt cgtcacaggc ctcggcataa   26880
tataaaacgc ctgatgatca gaggccgagg tatccagctc aacgacgagt cggtgagctc   26940
tccgcttggt ctacgaccag acggaatctt tcagattgcc ggctgcggga gatcttcctt   27000
cacccctcgt caggctgttc tgactttgga agttcgtct tcgcaacccc gctcgggcgg    27060
aatcgggacc gttcaatttg tagaggagtt tactccctct gtctacttca accccttctc   27120
cggatctcct gggcactacc cggacgagtt cataccgaac ttcgacgcga ttagcgagtc   27180
agtggacggc tacgattgat gtctggtgac gcggctgagc tatctcggct gcgacatcta   27240
gaccactgcc gccgctttcg ctgctttgcc cgggaactta ttgagttcat ctacttcgaa   27300
```

```
ctccccaagg atcaccctca aggtccggcc cacggagtgc ggattactat cgaaggcaaa    27360
atagactctc gcctgcaacg aatttctcc cagcggcccg tgctgatcga gcgagaccag     27420
ggaaacacca cggtttccat ctactgcatt tgtaatcacc ccggattgca tgaaagcctt    27480
tgctgtctta tgtgtactga gtttaataaa aactgaatta agactctcct acggactgcc   27540
gcttcttcaa cccggatttt acaaccagaa gaacaaaact tttcctgtcg tccaggactc    27600
tgttaacttc acctttccta ctcacaaact agaagctcaa cgactacacc gcttttccag   27660
aagcattttc cctactaata ctactttcaa aaccggaggt gagctccacg gtctccctac   27720
agaaaaccct tgggtggaag cgggccttgt agtactagga attcttgcgg gtgggcttgt    27780
gattattctt tgctacctat acacaccttg cttcactttc ctagtggtgt tgtggtattg    27840
gtttaaaaaa tggggcccat actagtcttg cttgttttac tttcgctttt ggaaccgggt   27900
tctgccaatt acgatccatg tctagacttt gacccagaaa actgcacact acttttgca    27960 cccgacacaa gccgcatctg tggagttctt attaagtgcg gatgggaatg caggtccgtt   28020
gaaattacac acaataacaa aacctggaac aataccttat ccaccacatg ggagccagga   28080
gttcccgagt ggtacactgt ctctgtccga ggtcctgacg gttccatccg cattagtaac   28140
aacactttca ttttttctga aatgtgcgat ctggccatgt tcatgagcaa acagtattct    28200
ctatggcctc ctagcaagga caacatcgta acgttctcca ttgcttattg cttgtgcgct   28260
tgccttctta ctgctttact gtgcgtatgc atacacctgc ttgtaaccac tcgcatcaaa   28320
aacgccaata acaaagaaaa aatgccttaa cctctttctg tttacagaca tggcttctct   28380
tacatctctc atatttgtca gcattgtcac tgccgctcac ggacaaacag tcgtctctat    28440
cccactagga cataattaca ctctcatagg accccccaatc acttcagagg tcatctggac   28500
caaactggga agcgttgatt actttgatat aatctgtaac aaaacaaaac caataatagt    28560
aacttgcaac atacaaaatc ttacattgat taatgttagc aaagtttaca gcggttacta    28620
ttatggttat gacagataca gtagtcaata tagaaattac ttggttcgtg ttacccagtt    28680
gaaaaccacg aaaatgccaa atatggcaaa gattcgatcc gatgacaatt ctctagaaac    28740
ttttacatct cccaccacac ccgacgaaaa aaacatccca gattcaatga ttgcaattgt    28800
tgcagcggtg gcagtggtga tggcactaat aataatatgc atgctttat atgcttgtcg    28860 ctacaaaaag tttcatccta aaaaacaaga tctcctacta aggcttaaca tttaattct    28920 ttttatacag ccatggtttc cactaccaca ttccttatgc ttactagtct cgcaactctg    28980
acttctgctc gctcacacct cactgtaact ataggctcaa actgcacact aaaaggacct    29040
caaggtggtc atgtcttttg gtggagaata tatgacaatg gatggttac aaaaccatgt    29100 gaccaacctg gtagatttt ctgcaacggc agagacctaa ccattatcaa cgtgacagca    29160
aatgacaaag gcttctatta tggaaccgac tataaaagta gtttagatta acattatt    29220 gtactgccat ctaccactcc agcaccccgc acaactactt tctctagcag cagtgtcgct    29280
aacaatacaa tttccaatcc aaccttgcc gcgcttttaa aacgcactgt gaataattct    29340
acaacttcac atacaacaat ttccacttca acaatcagca tcatcgctgc agtgacaatt    29400
ggaatatcta ttcttgtttt taccataacc tactacgcct gctgctatag aaaagacaaa    29460
cataaaggtg atccattact tagatttgat atttaatttg ttcttttttt ttatttacag    29520
tatggtgaac accaatcatg gtacctagaa atttcttctt caccatactc atctgtgctt    29580
ttaatgtttg cgctactttc acagcagtag ccacagcaac cccagactgt ataggagcat    29640
ttgcttccta tgcactttt gcttttgtta cttgcatctg cgtatgtagc atagtctgcc    29700
```

```
tggttattaa ttttttccaa cttctagact ggatccttgt gcgaattgcc tacctgcgcc   29760
accatcccga ataccgcaac caaaatatcg cggcacttct tagactcatc taaaaccatg   29820
caggctatac taccaatatt tttgcttcta ttgcttccct acgctgtctc aaccccagct   29880
gcctatagta ctccaccaga acaccttaga aaatgcaaat tccaacaacc gtggtcattt   29940
cttgcttgct atcgagaaaa atcagaaatc cccccaaatt taataatgat tgctggaata   30000
attaatataa tctgttgcac cataatttca tttttgatat accccctatt tgattttggc   30060
tggaatgctc ccaatgcaca tgatcatcca caagacccag aggaacacat tcccccacaa   30120
aacatgcaac atccaatagc gctaatagat tacgaaagtg aaccacaacc cccactactc   30180
cctgctatta gttacttcaa cctaaccggc ggagatgact gaaacactca ccacctccaa   30240
ttccgccgag gatctgctcg atatggacgg ccgcgtctca gaacaacgac ttgcccaact   30300
acgcatccgc cagcagcagg aacgcgtggc caaagagctc agagatgtca tccaaattca   30360
ccaatgcaaa aaaggcatat tctgtttggt aaaacaagcc aagatatcct acgagatcac   30420
cgctactgac catcgcctct cttacgaact tggcccccaa cgacaaaaat ttacctgcat   30480
ggtgggaatc aaccccatag ttatcaccca acaaagtgga gatactaagg gttgcattca   30540
ctgctcctgc gattccatcg agtgcaccta caccctgctg aagacccttat gcggcctaag   30600 agacctgcta ccaatgaatt aaaaaaaaat gattaataaa aaatcactta cttgaaatca   30660
gcaataaggt ctctgttgaa attttctccc agcagcacct cacttccctc ttcccaactc   30720
tggtattcta aaccccgttc agcggcatac tttctccata cttaaaggg gatgtcaaat    30780 tttagctcct ctcctgtacc cacaatcttc atgtcttttct tcccagatga ccaagagagt   30840
ccggctcagt gactccttca accctgtcta cccctatgaa gatgaaagca cctcccaaca   30900 ccccttata aacccagggt ttatttcccc aaatggcttc acacaaagcc cagacggagt   30960
tcttacttta aaatgtttaa ccccactaac aaccacaggc ggatctctac agctaaaagt   31020
gggaggggga cttacagtgg atgacactga tggtacctta caagaaaaca tacgtgctac   31080
agcacccatt actaaaaata atcactctgt agaactatcc attggaaatg gattagaaac   31140
tcaaaacaat aaactatgtg ccaaattggg aaatgggtta aaatttaaca acggtgacat   31200
ttgtataaag gatagtatta acaccttatg gactggaata aaccctccac ctaactgtca   31260
aattgtggaa aacactaata caaatgatgg caaacttact ttagtattag taaaaaatgg   31320
agggcttgtt aatggctacg tgtctctagt tggtgtatca gacactgtga accaaatgtt   31380
cacacaaaag acagcaaaca tccaattaag attatatttt gactcttctg gaaatctatt   31440
aactgaggaa tcagacttaa aaattccact taaaaataaa tcttctacag cgaccagtga   31500
aactgtagcc agcagcaaag cctttatgcc aagtactaca gcttatccct tcaacaccac   31560
tactagggat agtgaaaact acattcatgg aatatgttac tacatgacta gttatgatag   31620
aagtctattt cccttgaaca tttctataat gctaaacagc cgtatgattt cttccaatgt   31680
tgcctatgcc atacaattg aatggaatct aaatgcaagt gaatctccag aaagcaacat   31740
agctacgctg accacatccc cctttttctt ttcttacatt acagaagacg acaactaaaa   31800
taaagtttaa gtgttttttat ttaaaatcac aaaaattcgag tagttatttt gcctccacct   31860
tcccatttga cagaatacac caatctctcc ccacgcacag ctttaaacat ttggatacca   31920
ttagagatag acattgtttt agattccaca ttccaaacag tttcgagcg agccaatctg   31980 gggtcagtga tagataaaaa tccatcgcga tagtcttta aagcgctttc acagtccaac   32040
```

-continued

```
tgctgcggat gcgactccgg agtttggatc acggtcatct ggaagaagaa cgatgggaat    32100
cataatccga aaacggtatc ggacgattgt gtctcatcaa acccacaagc agccgctgtc    32160
tgcgtcgctc cgtgcgactg ctgttttatgg gatcagggtc cacagttttcc tgaagcatga  32220
ttttaatagc ccttaacatc aactttctgg tgcgatgcgc gcagcaacgc attctgattt    32280
cactcaaatc tttgcagtag gtacaacaca ttattacaat attgtttaat aaaccataat    32340
taaaagcgct ccagccaaaa ctcatatctg atataatcgc ccctgcatga ccatcatacc    32400
aaagtttaat ataaattaaa tgacgttccc tcaaaaacac actacccaca tacatgatct    32460
cttttggcat gtgcatatta acaatctgtc tgtaccatgg acaacgttgg ttaatcatgc    32520
aacccaatat aaccttccgg aaccacactg ccaacaccgc tcccccagcc atgcattgaa    32580
gtgaaccctg ctgattacaa tgacaatgaa gaacccaatt ctctcgaccg tgaatcactt    32640
gagaatgaaa aatatctata gtggcacaac atagacataa atgcatgcat cttctcataa    32700
tttttaactc ctcaggattt agaaacatat cccaggaat aggaagctct tgcagaacag    32760
taaagctggc agaacaagga agaccacgaa cacaacttac actatgcata gtcatagtat    32820
cacaatctgg caacagcggg tggtcttcag tcatagaagc tcgggtttca ttttcctcac    32880
aacgtggtaa ctgggctctg gtgtaagggt gatgtctggc gcatgatgtc gagcgtgcgc    32940
gcaaccttgt cataatggag ttgcttcctg acattctcgt attttgtata gcaaaacgcg    33000
gccctggcag aacacactct tcttcgcctt ctatcctgcc gcttagcgtg ttccgtgtga    33060
tagttcaagt acagccacac tcttaagttg gtcaaaagaa tgctggcttc agttgtaatc    33120
aaaactccat cgcatctaat tgttctgagg aaatcatcca cggtagcata tgcaaatccc    33180
aaccaagcaa tgcaactgga ttgcgtttca agcaggagag gagagggaag agacggaaga    33240
accatgttaa tttttattcc aaacgatctc gcagtacttc aaattgtaga tcgcgcagat    33300
ggcatctctc gcccccactg tgttggtgaa aaagcacagc taaatcaaaa gaaatgcgat    33360
tttcaaggtg ctcaacggtg gcttccaaca aagcctccac gcgcacatcc aagaacaaaa    33420
gaataccaaa agaaggagca ttttctaact cctcaatcat catattacat tcctgcacca    33480
ttcccagata attttcagct ttccagcctt gaattattcg tgtcagttct tgtggtaaat    33540
ccaatccaca cattacaaac aggtcccgga gggcgccctc caccaccatt cttaaacaca    33600
ccctcataat gacaaaatat cttgctcctg tgtcacctgt agcgaattga gaatggcaac    33660
atcaattgac atgcccttgg ctctaagttc ttctttaagt tctagttgta aaaactctct    33720
catattatca ccaaactgct tagccagaag ccccccggga acaagagcag gggacgctac    33780
agtgcagtac aagcgcagac ctccccaatt ggctccagca aaaacaagat tggaataagc    33840
atattgggaa ccaccagtaa tatcatcgaa gttgctggaa atataatcag gcagagtttc    33900
ttgtagaaat tgaataaaag aaaaatttgc caaaaaaaca ttcaaaacct ctgggatgca    33960
aatgcaatag gttaccgcgc tgcgctccaa cattgttagt tttgaattag tctgcaaaaa    34020
taaaaaaaaa acaagcgtca tatcatagta gcctgacgaa caggtggata atcagtctt    34080
tccatcacaa gacaagccac agggtctcca gctcgaccct cgtaaaacct gtcatcgtga    34140
ttaaacaaca gcaccgaaag ttcctcgcgg tgaccagcat gaataagtct tgatgaagca    34200
tacaatccag acatgttagc atcagttaag gagaaaaaac agccaacata gcctttgggt    34260
ataattatgc ttaatcgtaa gtatagcaaa gccaccccctc gcggatacaa agtaaaaggc    34320
acaggagaat aaaaaatata attatttctc tgctgctgtt taggcaacgt cgcccccggt    34380
ccctctaaat acacatacaa agcctcatca gccatggctt accagagaaa gtacagcggg    34440
```

-continued

```
cacacaaacc acaagctcta aagtcactct ccaacctstc cacaatatat atacacaagc    34500
cctaaactga cgtaatggga ctaaagtgta aaaatcccg ccaaacccaa cacacacccc    34560
gaaactgcgt caccagggaa aagtacagtt tcacttccgc aatcccaaca agcgtcactt    34620
cctctttctc acggtacgtc catcccatt aacttacaac gtcattttcc cacggccgcg    34680
ccgccccttt taaccgttaa ccccacagcc aatcaccaca cggcccacac ttttttaaaat  34740 cacctcattt acatattggc accattccat ctataaggta tattattgat gatg          34794
```

<210> SEQ ID NO 45
<211> LENGTH: 180
<212> TYPE: PRT
<213> ORGANISM: adenoviridae
<220> FEATURE:
<221> NAME/KEY: SITE
<222> LOCATION: (1)..(180)
<223> OTHER INFORMATION: /note="pCC536s E1B-21K sequence"

<400> SEQUENCE: 45

```
Met Glu Ala Trp Glu Cys Leu Glu Asp Phe Ser Ala Val Arg Asn Leu
 1               5                  10                  15

Leu Glu Gln Ser Ser Asn Ser Thr Ser Trp Phe Trp Arg Phe Leu Trp
            20                  25                  30

Gly Ser Ser Gln Ala Lys Leu Val Cys Arg Ile Lys Glu Asp Tyr Lys
        35                  40                  45

Trp Glu Phe Glu Glu Leu Leu Lys Ser Cys Gly Glu Leu Phe Asp Ser
    50                  55                  60

Leu Asn Leu Gly His Gln Ala Leu Phe Gln Glu Lys Val Ile Lys Thr
65                  70                  75                  80

Leu Asp Phe Ser Thr Pro Gly Arg Ala Ala Ala Val Ala Phe Leu
                85                  90                  95

Ser Phe Ile Lys Asp Lys Trp Ser Glu Glu Thr His Leu Ser Gly Gly
            100                 105                 110

Tyr Leu Leu Asp Phe Leu Ala Met His Leu Trp Arg Ala Val Val Arg
        115                 120                 125

His Lys Asn Arg Leu Leu Leu Ser Ser Val Arg Pro Ala Ile Ile
    130                 135                 140

Pro Thr Glu Glu Gln Gln Gln Gln Glu Glu Ala Arg Arg Arg Arg
145                 150                 155                 160

Gln Glu Gln Ser Pro Trp Asn Pro Arg Ala Gly Leu Asp Pro Val
                165                 170                 175

Glu Glu Ala Glu
            180
```

<210> SEQ ID NO 46
<211> LENGTH: 176
<212> TYPE: PRT
<213> ORGANISM: adenoviridae
<220> FEATURE:
<221> NAME/KEY: SITE
<222> LOCATION: (1)..(176)
<223> OTHER INFORMATION: /note="Ad5. E1B-21K sequence"

<400> SEQUENCE: 46

```
Met Glu Ala Trp Glu Cys Leu Glu Asp Phe Ser Ala Val Arg Asn Leu
 1               5                  10                  15

Leu Glu Gln Ser Ser Asn Ser Thr Ser Trp Phe Trp Arg Phe Leu Trp
            20                  25                  30
```

```
Gly Ser Ser Gln Ala Lys Leu Val Cys Arg Ile Lys Glu Asp Tyr Lys
            35                  40                  45

Trp Glu Phe Glu Glu Leu Leu Lys Ser Cys Gly Glu Leu Phe Asp Ser
     50                  55                  60

Leu Asn Leu Gly His Gln Ala Leu Phe Gln Glu Lys Val Ile Lys Thr
 65                  70                  75                  80

Leu Asp Phe Ser Thr Pro Gly Arg Ala Ala Ala Val Ala Phe Leu
                85                  90                  95

Ser Phe Ile Lys Asp Lys Trp Ser Glu Glu Thr His Leu Ser Gly Gly
                100                 105                 110

Tyr Leu Leu Asp Phe Leu Ala Met His Leu Trp Arg Ala Val Val Arg
            115                 120                 125

His Lys Asn Arg Leu Leu Leu Ser Ser Val Arg Pro Ala Ile Ile
 130                 135                 140

Pro Thr Glu Glu Gln Gln Gln Gln Glu Glu Ala Arg Arg Arg Arg
145                 150                 155                 160

Gln Glu Gln Ser Pro Trp Asn Pro Arg Ala Gly Leu Asp Pro Arg Glu
                165                 170                 175
```

<210> SEQ ID NO 47
<211> LENGTH: 180
<212> TYPE: PRT
<213> ORGANISM: adenoviridae
<220> FEATURE:
<221> NAME/KEY: SITE
<222> LOCATION: (1)..(180)
<223> OTHER INFORMATION: /note="Ad35.E1B-21K sequence"

<400> SEQUENCE: 47

```
Met Glu Val Trp Ala Ile Leu Glu Asp Leu Arg Lys Thr Arg Gln Leu
 1               5                  10                  15

Leu Glu Ser Ala Ser Asp Gly Val Ser Gly Phe Trp Arg Phe Trp Phe
            20                  25                  30

Ala Ser Glu Leu Ala Arg Val Val Phe Arg Ile Lys Gln Asp Tyr Lys
            35                  40                  45

Gln Glu Phe Glu Lys Leu Leu Val Asp Cys Pro Gly Leu Phe Glu Ala
     50                  55                  60

Leu Asn Leu Gly His Gln Val His Phe Lys Glu Lys Val Leu Ser Val
 65                  70                  75                  80

Leu Asp Phe Ser Thr Pro Gly Arg Thr Ala Ala Val Ala Phe Leu
                85                  90                  95

Thr Phe Ile Leu Asp Lys Trp Ile Pro Gln Thr His Phe Ser Arg Gly
                100                 105                 110

Tyr Val Leu Asp Phe Ile Ala Thr Ala Leu Trp Arg Thr Trp Lys Val
            115                 120                 125

Arg Lys Met Arg Thr Ile Leu Gly Tyr Trp Pro Val Gln Pro Leu Gly
 130                 135                 140

Val Ala Gly Ile Leu Arg His Pro Val Met Pro Ala Val Leu Glu
145                 150                 155                 160

Glu Glu Gln Gln Glu Asp Asn Pro Arg Ala Gly Leu Asp Pro Val
                165                 170                 175

Glu Glu Ala Glu
            180
```

<210> SEQ ID NO 48
<211> LENGTH: 494
<212> TYPE: PRT

-continued

```
<213> ORGANISM: adenoviridae
<220> FEATURE:
<221> NAME/KEY: SITE
<222> LOCATION: (1)..(494)
<223> OTHER INFORMATION: /note="pCC536s E1B-55K sequence"

<400> SEQUENCE: 48
```

| Met | Glu | Arg | Arg | Asn | Pro | Ser | Glu | Arg | Gly | Val | Pro | Ala | Gly | Phe | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | His | Ala | Ser | Val | Glu | Ser | Gly | Cys | Glu | Thr | Gln | Glu | Ser | Pro | Ala |
|     |     |     | 20  |     |     |     |     | 25  |     |     |     |     | 30  |     |     |

| Thr | Val | Val | Phe | Arg | Pro | Pro | Gly | Asp | Asn | Thr | Asp | Gly | Gly | Ala | Ala |
|     |     | 35  |     |     |     |     | 40  |     |     |     |     | 45  |     |     |     |

| Ala | Ala | Ala | Gly | Gly | Ser | Gln | Ala | Ala | Ala | Gly | Ala | Glu | Pro | Met |
|     | 50  |     |     |     |     | 55  |     |     |     |     | 60  |     |     |     |

| Glu | Pro | Glu | Ser | Arg | Pro | Gly | Pro | Ser | Ser | Gly | Gly | Gly | Val | Ala |
| 65  |     |     |     |     | 70  |     |     |     |     | 75  |     |     |     | 80  |

| Asp | Leu | Ser | Pro | Glu | Leu | Gln | Arg | Val | Leu | Thr | Gly | Ser | Thr | Ser | Thr |
|     |     |     |     | 85  |     |     |     |     | 90  |     |     |     |     | 95  |     |

| Gly | Arg | Asp | Arg | Gly | Val | Lys | Arg | Glu | Arg | Ala | Ser | Ser | Gly | Thr | Asp |
|     |     |     | 100 |     |     |     |     | 105 |     |     |     |     | 110 |     |     |

| Ala | Arg | Ser | Glu | Leu | Ala | Leu | Ser | Leu | Met | Ser | Arg | Arg | Arg | Pro | Glu |
|     |     | 115 |     |     |     |     | 120 |     |     |     |     | 125 |     |     |     |

| Thr | Ile | Trp | Trp | His | Glu | Val | Gln | Lys | Glu | Gly | Arg | Asp | Glu | Val | Ser |
|     | 130 |     |     |     |     | 135 |     |     |     |     | 140 |     |     |     |     |

| Val | Leu | Gln | Glu | Lys | Tyr | Ser | Leu | Glu | Gln | Val | Lys | Thr | Cys | Trp | Leu |
| 145 |     |     |     |     | 150 |     |     |     |     | 155 |     |     |     |     | 160 |

| Glu | Pro | Glu | Asp | Asp | Trp | Ala | Val | Ala | Ile | Lys | Asn | Tyr | Ala | Lys | Ile |
|     |     |     | 165 |     |     |     |     | 170 |     |     |     |     | 175 |     |     |

| Ala | Leu | Arg | Pro | Asp | Lys | Gln | Tyr | Lys | Ile | Ser | Arg | Arg | Ile | Asn | Ile |
|     |     |     | 180 |     |     |     |     | 185 |     |     |     |     | 190 |     |     |

| Arg | Asn | Ala | Cys | Tyr | Ile | Ser | Gly | Asn | Gly | Ala | Glu | Val | Val | Ile | Asp |
|     |     | 195 |     |     |     |     | 200 |     |     |     |     | 205 |     |     |     |

| Thr | Gln | Asp | Lys | Thr | Val | Ile | Arg | Cys | Cys | Met | Met | Asp | Met | Trp | Pro |
|     | 210 |     |     |     |     | 215 |     |     |     |     | 220 |     |     |     |     |

| Gly | Val | Val | Gly | Met | Glu | Ala | Val | Thr | Phe | Val | Asn | Val | Lys | Phe | Arg |
| 225 |     |     |     |     | 230 |     |     |     |     | 235 |     |     |     |     | 240 |

| Gly | Asp | Gly | Tyr | Asn | Gly | Ile | Val | Phe | Met | Ala | Asn | Thr | Lys | Leu | Ile |
|     |     |     |     | 245 |     |     |     |     | 250 |     |     |     |     | 255 |     |

| Leu | His | Gly | Cys | Ser | Phe | Phe | Gly | Phe | Asn | Asn | Thr | Cys | Val | Asp | Ala |
|     |     |     |     | 260 |     |     |     |     | 265 |     |     |     |     | 270 |     |

| Trp | Gly | Gln | Val | Ser | Val | Arg | Gly | Cys | Ser | Phe | Tyr | Ala | Cys | Trp | Ile |
|     |     |     | 275 |     |     |     |     | 280 |     |     |     |     | 285 |     |     |

| Ala | Thr | Ala | Gly | Arg | Thr | Lys | Ser | Gln | Leu | Ser | Leu | Lys | Lys | Cys | Ile |
|     |     | 290 |     |     |     |     | 295 |     |     |     |     | 300 |     |     |     |

| Phe | Gln | Arg | Cys | Asn | Leu | Gly | Ile | Leu | Asn | Glu | Gly | Glu | Ala | Arg | Val |
| 305 |     |     |     |     | 310 |     |     |     |     | 315 |     |     |     |     | 320 |

| Arg | His | Cys | Ala | Ser | Thr | Asp | Thr | Gly | Cys | Phe | Ile | Leu | Ile | Lys | Gly |
|     |     |     |     | 325 |     |     |     |     | 330 |     |     |     |     | 335 |     |

| Asn | Ala | Ser | Val | Lys | His | Asn | Met | Ile | Cys | Gly | Ala | Ser | Asp | Glu | Arg |
|     |     |     |     | 340 |     |     |     |     | 345 |     |     |     |     | 350 |     |

| Pro | Tyr | Gln | Met | Leu | Thr | Cys | Ala | Gly | Gly | His | Cys | Asn | Met | Leu | Ala |
|     |     |     |     | 355 |     |     |     |     | 360 |     |     |     |     | 365 |     |

| Thr | Val | His | Ile | Val | Ser | His | Gln | Arg | Lys | Lys | Trp | Pro | Val | Phe | Asp |
|     |     |     | 370 |     |     |     |     | 375 |     |     |     |     | 380 |     |     |

-continued

```
His Asn Val Leu Thr Lys Cys Thr Met His Ala Gly Gly Arg Arg Gly
385                 390                 395                 400

Met Phe Met Pro Tyr Gln Cys Asn Met Asn His Val Lys Val Leu Leu
                405                 410                 415

Glu Pro Asp Ala Phe Ser Arg Met Ser Leu Thr Gly Ile Phe Asp Met
                420                 425                 430

Asn Thr Gln Ile Trp Lys Ile Leu Arg Tyr Asp Asp Thr Arg Ser Arg
                435                 440                 445

Val Arg Ala Cys Glu Cys Gly Gly Lys His Ala Arg Phe Gln Pro Val
        450                 455                 460

Cys Val Asp Val Thr Glu Asp Leu Arg Pro Asp His Leu Val Ile Ala
465                 470                 475                 480

Arg Thr Gly Ala Glu Phe Gly Ser Ser Gly Glu Glu Thr Asp
                485                 490
```

<210> SEQ ID NO 49
<211> LENGTH: 494
<212> TYPE: PRT
<213> ORGANISM: adenoviridae
<220> FEATURE:
<221> NAME/KEY: SITE
<222> LOCATION: (1)..(494)
<223> OTHER INFORMATION: /note="Ad35. E1B-55K sequence"

<400> SEQUENCE: 49

```
Met Asp Pro Ala Asp Ser Phe Gln Gln Gly Ile Arg Phe Gly Phe His
1               5                   10                  15

Ser His Ser Ile Val Glu Asn Met Glu Gly Ser Gln Asp Glu Asp Asn
                20                  25                  30

Leu Arg Leu Leu Ala Ser Ala Ala Phe Gly Cys Ser Gly Asn Pro Glu
            35                  40                  45

Ala Ser Thr Gly His Ala Ser Gly Ser Gly Gly Thr Ala Arg Gly
        50                  55                  60

Gln Pro Glu Ser Arg Pro Gly Pro Ser Ser Gly Gly Gly Val Ala
65                  70                  75                  80

Asp Leu Ser Pro Glu Leu Gln Arg Val Leu Thr Gly Ser Thr Ser Thr
                85                  90                  95

Gly Arg Asp Arg Gly Val Lys Arg Glu Arg Ala Ser Ser Gly Thr Asp
                100                 105                 110

Ala Arg Ser Glu Leu Ala Leu Ser Leu Met Ser Arg Arg Arg Pro Glu
            115                 120                 125

Thr Ile Trp Trp His Glu Val Gln Lys Glu Gly Arg Asp Glu Val Ser
    130                 135                 140

Val Leu Gln Glu Lys Tyr Ser Leu Glu Gln Val Lys Thr Cys Trp Leu
145                 150                 155                 160

Glu Pro Glu Asp Asp Trp Ala Val Ala Ile Lys Asn Tyr Ala Lys Ile
                165                 170                 175

Ala Leu Arg Pro Asp Lys Gln Tyr Lys Ile Ser Arg Arg Ile Asn Ile
            180                 185                 190

Arg Asn Ala Cys Tyr Ile Ser Gly Asn Gly Ala Glu Val Val Ile Asp
        195                 200                 205

Thr Gln Asp Lys Thr Val Ile Arg Cys Cys Met Met Asp Met Trp Pro
    210                 215                 220

Gly Val Val Gly Met Glu Ala Val Thr Phe Val Asn Val Lys Phe Arg
225                 230                 235                 240
```

```
Gly Asp Gly Tyr Asn Gly Ile Val Phe Met Ala Asn Thr Lys Leu Ile
                245                 250                 255

Leu His Gly Cys Ser Phe Phe Gly Phe Asn Asn Thr Cys Val Asp Ala
                260                 265                 270

Trp Gly Gln Val Ser Val Arg Gly Cys Ser Phe Tyr Ala Cys Trp Ile
                275                 280                 285

Ala Thr Ala Gly Arg Thr Lys Ser Gln Leu Ser Leu Lys Lys Cys Ile
            290                 295                 300

Phe Gln Arg Cys Asn Leu Gly Ile Leu Asn Glu Gly Glu Ala Arg Val
305                 310                 315                 320

Arg His Cys Ala Ser Thr Asp Thr Gly Cys Phe Ile Leu Ile Lys Gly
                325                 330                 335

Asn Ala Ser Val Lys His Asn Met Ile Cys Gly Ala Ser Asp Glu Arg
                340                 345                 350

Pro Tyr Gln Met Leu Thr Cys Ala Gly Gly His Cys Asn Met Leu Ala
                355                 360                 365

Thr Val His Ile Val Ser His Gln Arg Lys Lys Trp Pro Val Phe Asp
                370                 375                 380

His Asn Val Leu Thr Lys Cys Thr Met His Ala Gly Gly Arg Arg Gly
385                 390                 395                 400

Met Phe Met Pro Tyr Gln Cys Asn Met Asn His Val Lys Val Leu Leu
                405                 410                 415

Glu Pro Asp Ala Phe Ser Arg Met Ser Leu Thr Gly Ile Phe Asp Met
                420                 425                 430

Asn Thr Gln Ile Trp Lys Ile Leu Arg Tyr Asp Asp Thr Arg Ser Arg
            435                 440                 445

Val Arg Ala Cys Glu Cys Gly Gly Lys His Ala Arg Phe Gln Pro Val
        450                 455                 460

Cys Val Asp Val Thr Glu Asp Leu Arg Pro Asp His Leu Val Ile Ala
465                 470                 475                 480

Arg Thr Gly Ala Glu Phe Gly Ser Ser Gly Glu Thr Asp
                485                 490

<210> SEQ ID NO 50
<211> LENGTH: 496
<212> TYPE: PRT
<213> ORGANISM: adenoviridae
<220> FEATURE:
<221> NAME/KEY: SITE
<222> LOCATION: (1)..(496)
<223> OTHER INFORMATION: /note="Ad5. E1B-55K sequence"

<400> SEQUENCE: 50

Met Glu Arg Arg Asn Pro Ser Glu Arg Gly Val Pro Ala Gly Phe Ser
  1               5                  10                  15

Gly His Ala Ser Val Glu Ser Gly Cys Glu Thr Gln Glu Ser Pro Ala
             20                  25                  30

Thr Val Val Phe Arg Pro Pro Gly Asp Asn Thr Asp Gly Gly Ala Ala
         35                  40                  45

Ala Ala Ala Gly Gly Ser Gln Ala Ala Ala Ala Gly Ala Glu Pro Met
     50                  55                  60

Glu Pro Glu Ser Arg Pro Gly Pro Ser Gly Met Asn Val Val Gln Val
65                  70                  75                  80

Ala Glu Leu Tyr Pro Glu Leu Arg Arg Ile Leu Thr Ile Thr Glu Asp
                 85                  90                  95

Gly Gln Gly Leu Lys Gly Val Lys Arg Glu Arg Gly Ala Cys Glu Ala
```

-continued

```
                100                 105                 110
Thr Glu Glu Ala Arg Asn Leu Ala Phe Ser Leu Met Thr Arg His Arg
        115                 120                 125

Pro Glu Cys Ile Thr Phe Gln Gln Ile Lys Asp Asn Cys Ala Asn Glu
        130                 135                 140

Leu Asp Leu Leu Ala Gln Lys Tyr Ser Ile Glu Gln Leu Thr Thr Tyr
145                 150                 155                 160

Trp Leu Gln Pro Gly Asp Asp Phe Glu Glu Ala Ile Arg Val Tyr Ala
                165                 170                 175

Lys Val Ala Leu Arg Pro Asp Cys Lys Tyr Lys Ile Ser Lys Leu Val
                180                 185                 190

Asn Ile Arg Asn Cys Cys Tyr Ile Ser Gly Asn Gly Ala Glu Val Glu
                195                 200                 205

Ile Asp Thr Glu Asp Arg Val Ala Phe Arg Cys Ser Met Ile Asn Met
210                 215                 220

Trp Pro Gly Val Leu Gly Met Asp Gly Val Val Ile Met Asn Val Arg
225                 230                 235                 240

Phe Thr Gly Pro Asn Phe Ser Gly Thr Val Phe Leu Ala Asn Thr Asn
                245                 250                 255

Leu Ile Leu His Gly Val Ser Phe Tyr Gly Phe Asn Asn Thr Cys Val
                260                 265                 270

Glu Ala Trp Thr Asp Val Arg Val Arg Gly Cys Ala Phe Tyr Cys Cys
                275                 280                 285

Trp Lys Gly Val Val Cys Arg Pro Lys Ser Arg Ala Ser Ile Lys Lys
        290                 295                 300

Cys Leu Phe Glu Arg Cys Thr Leu Gly Ile Leu Ser Glu Gly Asn Ser
305                 310                 315                 320

Arg Val Arg His Asn Val Ala Ser Asp Cys Gly Cys Phe Met Leu Val
                325                 330                 335

Lys Ser Val Ala Val Ile Lys His Asn Met Val Cys Gly Asn Cys Glu
                340                 345                 350

Asp Arg Ala Ser Gln Met Leu Thr Cys Ser Asp Gly Asn Cys His Leu
        355                 360                 365

Leu Lys Thr Ile His Val Ala Ser His Ser Arg Lys Ala Trp Pro Val
        370                 375                 380

Phe Glu His Asn Ile Leu Thr Arg Cys Ser Leu His Leu Gly Asn Arg
385                 390                 395                 400

Arg Gly Val Phe Leu Pro Tyr Gln Cys Asn Leu Ser His Thr Lys Ile
                405                 410                 415

Leu Leu Glu Pro Glu Ser Met Ser Lys Val Asn Leu Asn Gly Val Phe
                420                 425                 430

Asp Met Thr Met Lys Ile Trp Lys Val Leu Arg Tyr Asp Glu Thr Arg
        435                 440                 445

Thr Arg Cys Arg Pro Cys Glu Cys Gly Gly Lys His Ile Arg Asn Gln
        450                 455                 460

Pro Val Met Leu Asp Val Thr Glu Glu Leu Arg Pro Asp His Leu Val
465                 470                 475                 480

Leu Ala Cys Thr Arg Ala Glu Phe Gly Ser Ser Asp Glu Asp Thr Asp
                485                 490                 495
```

COMPLEMENTING CELL LINES

CROSS-REFERENCE TO RELATED APPLICATION

This application is a continuation-in-part of application Ser. No. 09/713,678, filed Nov. 15, 2000, now U.S. Pat. No. 6,492,169.

TECHNICAL FIELD

The invention relates to the field of biotechnology generally and, more specifically, to adenoviral-based complementing cell lines.

BACKGROUND OF THE INVENTION

Typically, vector and packaging cells have to be adapted to one another so that they have all the necessary elements, but they do not have overlapping elements that lead to replication-competent virus by recombination. Therefore, the sequences necessary for proper transcription of the packaging construct may be heterologous regulatory sequences derived from, for example, other human adenovirus (Ad) serotypes, nonhuman adenoviruses other viruses like, but not limited to, SV40, hepatitis B virus (HBV), Rous Sarcoma Virus (RSV), cytomegalovirus (CMV), etc. or from higher eukaryotes such as mammals. In general, these sequences include a promoter, enhancer and polyadenylation sequences.

The PER.C6 is an example of a cell line devoid of sequence overlap between the packaging construct and the adenoviral vector (Fallaux et al, 1998). The PER.C6 cell line was deposited under ECACC deposit number 96022940 under the provisions of the Budapest Treaty with the Centre for Applied Microbiology and Research Authority (European Collection of Animal Cell Cultures), Porton Down, Salisbury, Wiltshire SP4, OJG, United Kingdom, an International Depository Authority on Feb. 29, 1996. Recombinant viruses based on subgroup C adenoviruses, such as Ad5 and Ad2, can be propagated efficiently on these packaging cells. Generation and propagation of adenoviruses from other serotypes, like subgroup B viruses, has proven to be more difficult on PER.C6 cells. However, as described in European patent application 00201738.2, recombinant viruses based on subgroup B virus Ad35 can be made by co-transfection of an expression construct containing the Ad35 early region-1 sequences (Ad35-E1). Furthermore, Ad35-based viruses that are deleted for E1A sequences were shown to replicate efficiently on PER.C6 cells. Thus, the E1A proteins of Ad5 complement Ad35-E1A functions, whereas, at least part of the E1B functions of Ad35 are necessary. This serotype specificity in E1B functions was recently also described for Ad7 recombinant viruses. In an attempt to generate recombinant adenoviruses derived from subgroup B virus Ad7, Abrahamsen et al. (1997) were not able to generate E1-deleted viruses on 293 cells without contamination of wild-type (wt) Ad7. Viruses that were picked after plaque purification on 293-ORF6 cells (Brough et al., 1996) were shown to have incorporated Ad7-E1B sequences by nonhomologous recombination. Thus, efficient propagation of Ad7 recombinant viruses proved possible only in the presence of Ad7-E1B expression and Ad5-E4-ORF6 expression. The E1B proteins are known to interact with cellular, as well as viral, proteins (Bridge et al., 1993; White, 1995). Possibly, the complex formed between the E1B-55K protein and E4-ORF6 which is necessary to increase mRNA export of viral proteins and to inhibit export of most cellular mRNAs, is critical and in some way serotype-specific.

DESCRIPTION OF THE INVENTION

The present invention provides new packaging cell lines capable of complementing recombinant adenoviruses based on serotypes other than subgroup C viruses, such as serotypes from subgroup B like adenovirus type 35.

In one aspect, the invention provides packaging cell lines capable of complementing recombinant adenovirus based on a serotype of subgroup B, preferably of serotype 35. With the terms "based on or derived from an adenovirus" is meant that it utilizes nucleic acid corresponding to nucleic acid found in the serotype. The utilized nucleic acid may be derived by PCR cloning or other methods known in the art.

In one aspect, the new packaging cells are derived from primary, diploid human cells such as, but not limited to, primary human retinoblasts, primary human embryonic kidney cells or primary human amniocytes. Transfection of primary cells or derivatives thereof with the adenovirus E1A gene alone can induce unlimited proliferation (immortalization), but does not result in complete transformation. However, expression of E1A in most cases results in induction of programmed cell death (apoptosis), and occasionally immortalization is obtained (Jochemsen et al., 1987). Co-expression of the E1B gene is required to prevent induction of apoptosis and for complete morphological transformation to occur (reviewed in White, 1995). Therefore, in one aspect of the invention, primary human cells or derivatives thereof are transformed by expression of adenovirus E1 proteins of a subgroup other than subgroup C, preferably subgroup B, more preferably adenovirus type 35. The combined activity of the E1A and E1B proteins establishes indefinite growth of the cells and enables complementation of recombinant adenoviruses.

The complete morphological transformation of primary cells by adenovirus E1 genes is the result of the combined activities of the proteins encoded by the E1A and E1B regions. The roles of the different E1 proteins in lytic infection and in transformation have been studied extensively (reviewed in Zantema and van der Eb, 1995; White, 1995, 1996). The adenovirus E1A proteins are essential for transformation of primary cells. The E1A proteins exert this effect through direct interaction with a number of cellular proteins that are involved in regulation of transcription. These include the pRB family of proteins, p300/CBP and TATA binding protein. In addition to this E1A increases the level of p53 protein in the cells. In the absence of adenovirus E1B activity the rise in p53 levels leads to the induction of apoptosis. Both proteins encoded by the E1B region counteract the induction of apoptosis although by different mechanisms. E1B-21K seems to counteract apoptosis in a manner similar to Bcl-2 via interaction with the effector proteins downstream in the apoptosis pathway (Han et al., 1996), whereas E1B-55K functions through direct interaction with p53. Importantly, the molecular mechanism by which the E1B-55K proteins of Ad2 and 5 (subgroup C) and Ad12 (subgroup A) function in the ability to neutralise p53 may differ. Whereas Ad5 E1B-55K binds p53 strongly and the complex locals to the cytoplasm, Ad12 E1B-55K binds p53 weakly and both proteins are localised in the nucleus (Zantema et al, 1985; Grand et al., 1999). Both proteins, however, inhibit the transactivation of other genes by p53 (Yew and Berk, 1992).

In rodent cells, the activity of E1A together with either E1B-21K or 55K is sufficient for full transformation although expression of both E1B proteins together is twice as efficient (Rao et al, 1992). In human cells however, the activity of the E1B-55K protein seems to be more important given the observation that E1B-55K is indispensible for the establishment of transformed cells (Gallimore, 1986).

Example 6 hereof describes the generation of pIG270. In this construct the Ad35-E1 genes are expressed from the HPGK promoter and transcription is terminated by the HBVpA. The HPGK promoter constitutes a HincII-EcoRI fragment of the promoter sequence described by Singer-Sam et al. (1984). The HBVpA is located in a BamHI-BglII fragment of the Hepatitis B virus genome (Simonsen and Levinson, 1983; see also Genbank HBV-AF090841). As mentioned before, the promoter and polyadenylation sequences of the E1 expression constructs described in this invention may be derived from other sources without de n from the invention. Also, other functional fragments of the hPGK and HBVpA sequences mentioned above may be used.

The functionality of pIG270 was shown by transformation of Baby Rat Kidney cells (BRK). Comparison with an equivalent Ad5-E1 expression construct taught that Ad35-E1 genes were less efficient in transforming these cells. The same has been found for the E1 genes of Ad12 (B et al., 1982).

It is unclear which E1 protein(s) determine(s) the difference in transformation efficiency of E1 sequences observed for adenoviruses from different subgroups. In the case of Ad12, transfection studies with chimeric E1A/E1B genes suggested that the efficiency of transformation of BRK cells was determined by the E1A proteins (Bernards et al., 1982). The E1B-55K protein is shown infra to contain serotype-specific functions necessary for complementation of E1-deleted adenoviruses. If these functions are related to the regulation of mRNA distribution or another late viral function, it is unlikely that these are involved in the transformation efficiency.

Analysis of functional domains in the Ad2 or Ad5 E1B-55K proteins using insertion mutants have revealed that functions related to viral replication, late protein synthesis and host protein shut-off are not confined to specific domains but are distributed along the protein (Yew et al., 1990). Using the same set of mutants, the domains important for interaction with p53 and E4-Orf6 were found to be more restricted. In addition to one common binding region (amino acids 262 to 326), p53 binding was affected by mutations at aa 180 and E4-Oaf6 binding was affected by mutations at aa 143 (Yew and Berk, 1992; Rubenwolf et al., 1997).

Altogether these results indicate that it is difficult to separate the E1B-55K functions related to transformation p53 binding) and late protein synthesis (Orf6 binding).

The invention discloses now E1 constructs that combine the high efficiency of transformation of one serotype with the serotype-specific complementation function of another serotype. These new constructs are used to transform primary human embryonic retinoblast cells and human amniocytes.

In another aspect of the invention, the transforming E1 sequences are derived from different serotypes. As disclosed in European Patent application 002017382, Ad35E1 sequences are capable of transforming Baby Rat Kidney (BRK) cells, albeit with a lower efficiency than that seen with Ad5-E1 sequences. This was also observed for E1 sequences from Ad12 (Bernards et al., 1982). Therefore, in this aspect of the invention, primary diploid human cells or derivatives thereof are transformed with chimeric E1 construct that consists of part of the E1 sequences of a serotype that enables efficient transformation of primary human cells or derivatives thereof and part of the E1 sequences of another serotype which E1 sequences provide the serotype-specific E1B function(s) that enable(s) efficient propagation of E1-deleted viruses of that serotype. In a preferred embodiment of this aspect of the invention, the E1A region is derived from a subgroup C adenovirus like, but not limited to, Ad5, and the E1B coding sequences are derived from an alternative adenovirus, more particularly from an adenovirus of subgroup B, even more particularly from adenovirus type 35. E1B-21K coding sequences may also be chimeric comprising both subgroup C and subgroup B coding sequences. Preferably, all or most of E1B-21K comprises subgroup C coding sequences. In a more preferred embodiment, the E1A coding sequences and the E1B-21K coding sequences are derived from a subgroup C adenovirus, like, but not limited to, Ad5. In one embodiment the cell further comprises E1B-55k coding sequences that are, preferably, as far as not overlapping with the 21K coding sequences-derived from an adenovirus of subgroup B, more particularly from adenovirus type 35. In an even more preferred embodiment, all E1 coding sequences are derived from a subgroup C adenovirus, like but not limited to Ad5, except for at least the part of the E1B-55K coding sequences that are necessary for serotype-specific complementation of an alternative adenovirus subgroup, more particularly adenovirus subgroup B, even more particular adenovirus type 35. The invention also provides a packaging cell line wherein the primary, diploid human cells or derivatives thereof have been transformed with a chimeric adenovirus E1 construct comprising part of a first adenovirus E1 coding sequence of a first adenovirus serotype that enables efficient transformation of primary human cells and derivatives thereof; and part of a second adenovirus E1 coding sequence of a second adenovirus serotype, wherein the second adenovirus E1 coding sequence provides the serotype-specific adenovirus E1B function(s) that enable(s) efficient propagation of recombinant adenovirus E1-deleted ruses of the second adenovirus serotype. Preferably, the first adenovirus serotype is a subgroup C adenovirus and the second adenovirus serotype is a subgroup B adenovirus, more particular adenovirus type 35. In one embodiment the packing cell line of the invention comprises bovine adenovirus E1B-55k. Such a bovine E1B-55k expressing cell line is particularly suited for obtaining high yields of a complemented bovine recombinant adenovirus.

The primary diploid human cells or derivatives thereof are transformed by adenovirus E1 sequences, either operatively linked on one DNA molecule or located on two separate DNA molecules. In the latter case, one DNA molecule carries at least part of the E1 sequences of the serotype-enabling efficient transformation and the second DNA molecule carries at least part of the sequences necessary for serotype-specific complementation. Also provided is a hybrid construct including E1-sequences of the serotype enabling efficient transformation and E1 sequences of another serotype necessary for serotype-specific complementation. The sequences providing serotype specific complementation may of course also contain further activities contributing to transformation. Preferably, the sequences enabling efficient transformation comprise E1A. Preferably, the sequences and the sequences necessary for serotype specific complementation preferably comprise E1B sequences. More preferably, the sequences enabling efficient transforming comprise E1A and E1B-21K sequences and the sequences necessary for serotype specific complementation comprise E1B-55K sequences. Also provided are cells transformed by such hybrid construct Such cells can favorably be used for the propagation of recombinant E1 deleted adenovirus of another serotype. Of course, it is also possible to provide both functions of E1 sequences on separate constructs. In all aspects, the sequences are operatively linked to regulatory sequences enabling transcription and translation of the encoded proteins. Preferably, a packaging cell of the invention further comprises a DNA encoding at least E4-orf6 of an adenovirus of subgroup B, preferably adenovirus serotype 35. Preferably, the E4-orf6 is derived from the another serotype. Preferably, the cell comprises E1B-55K and E4-orf6 of the same serotype as the recombinant vector to be propagated/complemented or otherwise produced.

In another aspect of the invention, new packaging cells are described that are derived from PER.C6 (ECACC deposit number 96022940; Fallaux et al., 1998) and contain Ad35-E1 sequences integrated into their genome. These Ad35-E1 sequences are present in a functional expression cassette, but preferably do not contain sequences overlapping with sequences present in the recombinant viral vector. Preferably, the functional expression cassette consists of a heterologous promoter and poly-adenylation signal functionally linked to Ad35-E1 sequences. More specifically, the Ad35-E1 coding sequences are functionally linked to the human phosphoglycerate gene promoter (hPGK) and hepatitus B virus poly-adenylation signal (HBV-pA). Preferably, Ad35-E1 coding sequences comprise the coding regions of the E1A proteins and the E1B promoter sequences linked to E1B coding sequences up to and including the stop codon of the E1B 55K protein. More preferably, the Ad35-E1 sequences comprise nucleotide 468 to nucleotide 3400 of the Ad35 wt sequence. To be able to select for transfected cells, a dominant selection marker like, but not limited to, the neo gene has to be incorporated on the expression vector or the Ad35 expression vector is cotransfected with a separate expression vector mediating expression of the selection marker. In both cases, the selection marker becomes integrated in the cellular genome. Other Ad5-E1 transformed cell lines like 293 (Graham et al., 1977) and 911 (Fallaux et al., 1996) or established human cell lines like A549 cells may be used without departing from the present invention.

In another aspect of the invention, PER.C6-derived cells are described that express functional Ad35-E1B sequences. In one embodiment, the Ad35-E1B coding sequences are driven by the E1B promoter and terminated by a heterologous poly-adenylation signal like, but not limited to, the HBVpA In a preferred embodiment, the Ad35-E1B coding sequences are driven by a heterologous promoter like, but not limited to, the hPGK promoter or Elongation Factor-1α (EF-1α) promoter and terminated by a heterologous pA signal like, but not limited to, the HBVpA. These Ad35-E1B sequences preferably comprise the coding regions of the E1B-21K and the E1B-55K proteins located between nucleotides 1611 and 3400 of the wild-type (wt) Ad35 sequence. More preferably, the Ad35-E1B sequences comprise nucleotides 1550 to 3400 of the wt Ad35 sequence. In an even more preferred embodiment, the E1B sequences comprise the coding sequences of the E1B-55K gene located between nucleotides 1916 and 3400 of the wt Ad35 sequence. In an even more preferred embodiment a packaging cell line or a cell line of the invention lacks a functional coding sequence for E1B 21k. Such cell line, in general, produce significantly more recombinant adenovirus than E1B 21K positive cell lines.

The invention further provides a method for complementing a recombinant adenovirus comprising providing a packaging cell line or a cell line according to the invention, with the recombinant adenovirus and culturing the cell to allow for complementation. In a preferred embodiment the method further comprises harvesting complemented recombinant adenovirus. Preferably, the recombinant adenovirus is derived from adenovirus subgroup B. More preferably, the recombinant adenovirus is derived from adenovirus serotype 35.

In another aspect, the invention provides a recombinant adenovirus obtained by a method of the invention or with a packaging cell of the invention. Such an adenovirus can be obtained essentially free from contaminating wild type adenovirus, or replication competent adenovirus. Such recombinant adenovirus preparations are very suited for administration of therapeutic sequences to somatic tissues in vivo in for instance a gene therapeutic setting. Preferred are recombinant adenoviruses comprising a deletion of nucleic acid encoding at least one E1-region protein. Preferably, such adenovirus further comprises a deletion of nucleic acid encoding at least one E3-region protein. Preferably, such adenovirus further comprises a deletion of nucleic acid encoding at least one E4region protein. Preferably, such adenovirus further comprises a deletion of nucleic acid encoding at least E4-Orf6 protein. For this reason, the invention also provides the use of a recombinant adenovirus of the invention for the preparation of a medicament.

With the term E1B-55K protein as used herein, is meant the protein encoded by the E1B-region in an adenovirus serotype having a similar function in the serotype as provided by the E1B-55K protein Ad5.

With the term E1B-21K protein as used herein, is meant the protein enclosed by the E1B-region in an adenovirus serotype having a similar function in the serotype as provided by the E1B-19K protein of Ad5. The same terminology applies for the sequences encoding these proteins. When referring to Ad35-E1 sequences from a specified nucleotide to nucleotide 3400 is meant up to and including nucleotide 3400'.

Cell lines subject of this invention are useful for, among other th the production of recombinant adenoviruses designed for gene therapy and vaccination. The cell lines, being derived from cells of human origin, are also useful for the production of human recombinant therapeutic proteins like, but not limited to human growth factors, human antibodies. In addition the cell lines are useful for the production of human viruses other than adenovirus like, but not limited to, influenza virus, herpes simplex virus, rotavirus, measles virus.

A preferred derivative of primary, diploid human cells is the PER.C6 cell line (ECACC deposit number 960022940).

It is within the skills of the artisan to provide for proteins having a similar function in kind as the adenovirus E1 protein referred to in this document. For instance a functional part may be provided and/or a derivative may be provided with a similar function in kind, not necessarily in amount.

Such parts and derivatives are considered to be part of the invention, in as far as similar transforming/complementing and/or serotype specificity function is provided in kind, not necessarily in amount.

BRIEF DESCRIPTION OF THE FIGS

FIG. 1: Bar graph showing the percentage of serum samples positive for neutralization for each human wt adenovirus tested (see, Example 1 for description of the neutralization assay).

Figure 2:
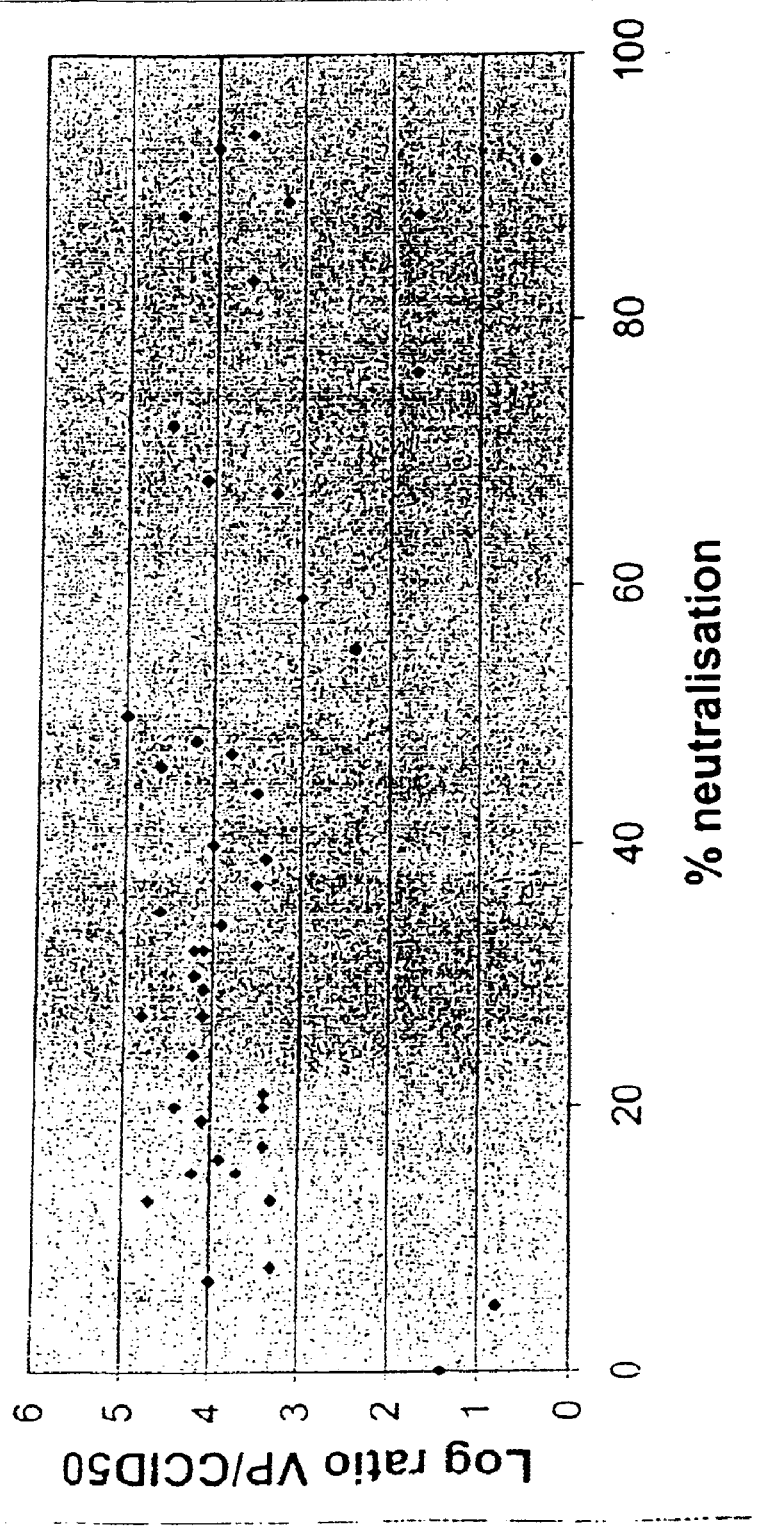

FIG. 2: Graph showing absence of correlation between the VP/CCID50 ratio and the percentage of neutralization.

Figure 3:
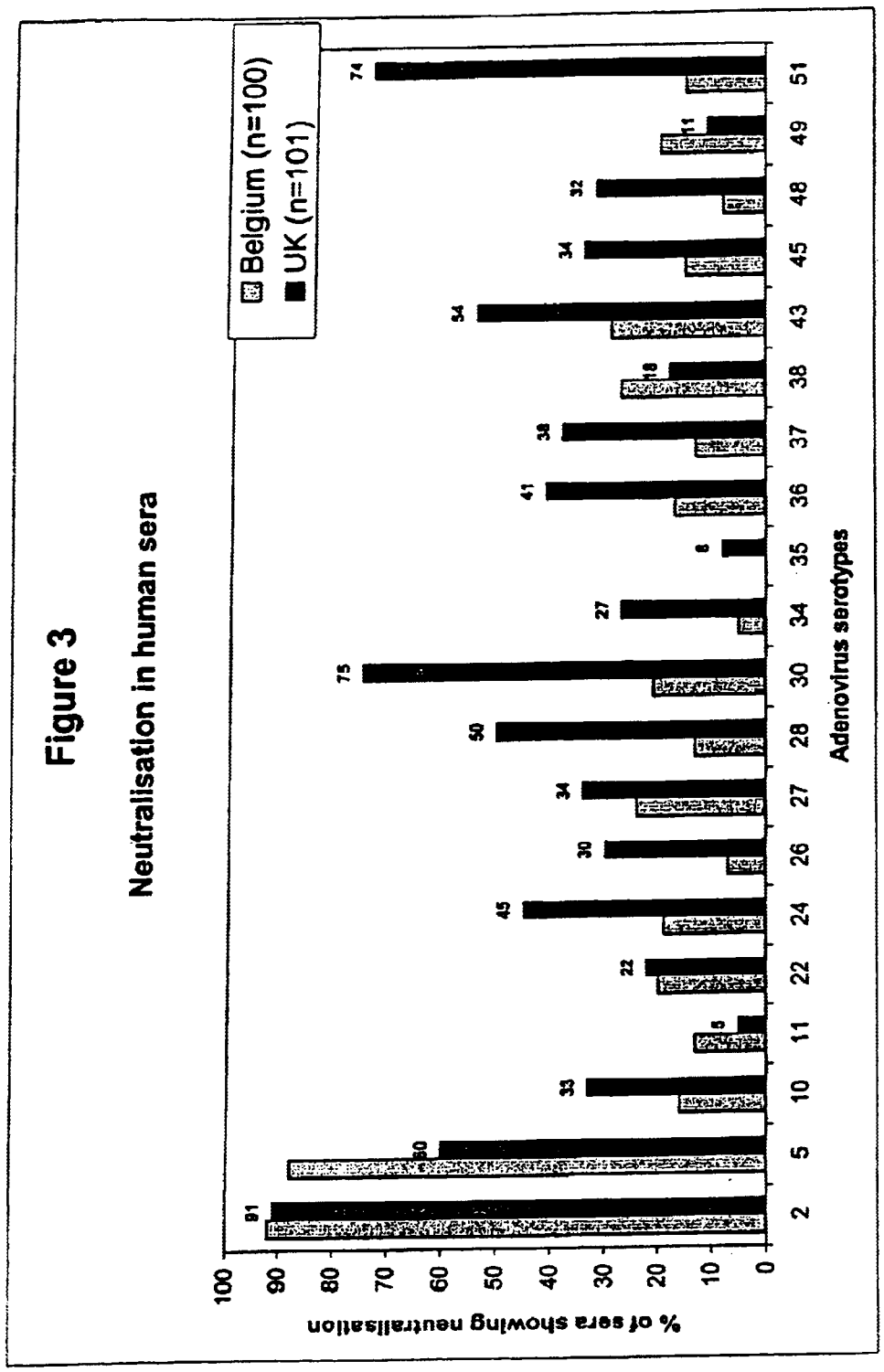

FIG. 3: Bar graph presenting the percentage sera samples that show neutralizing activity to a selection of adenovirus serotype. Sera were derived from healthy volunteers from Belgium and the UK.

Figure 4:
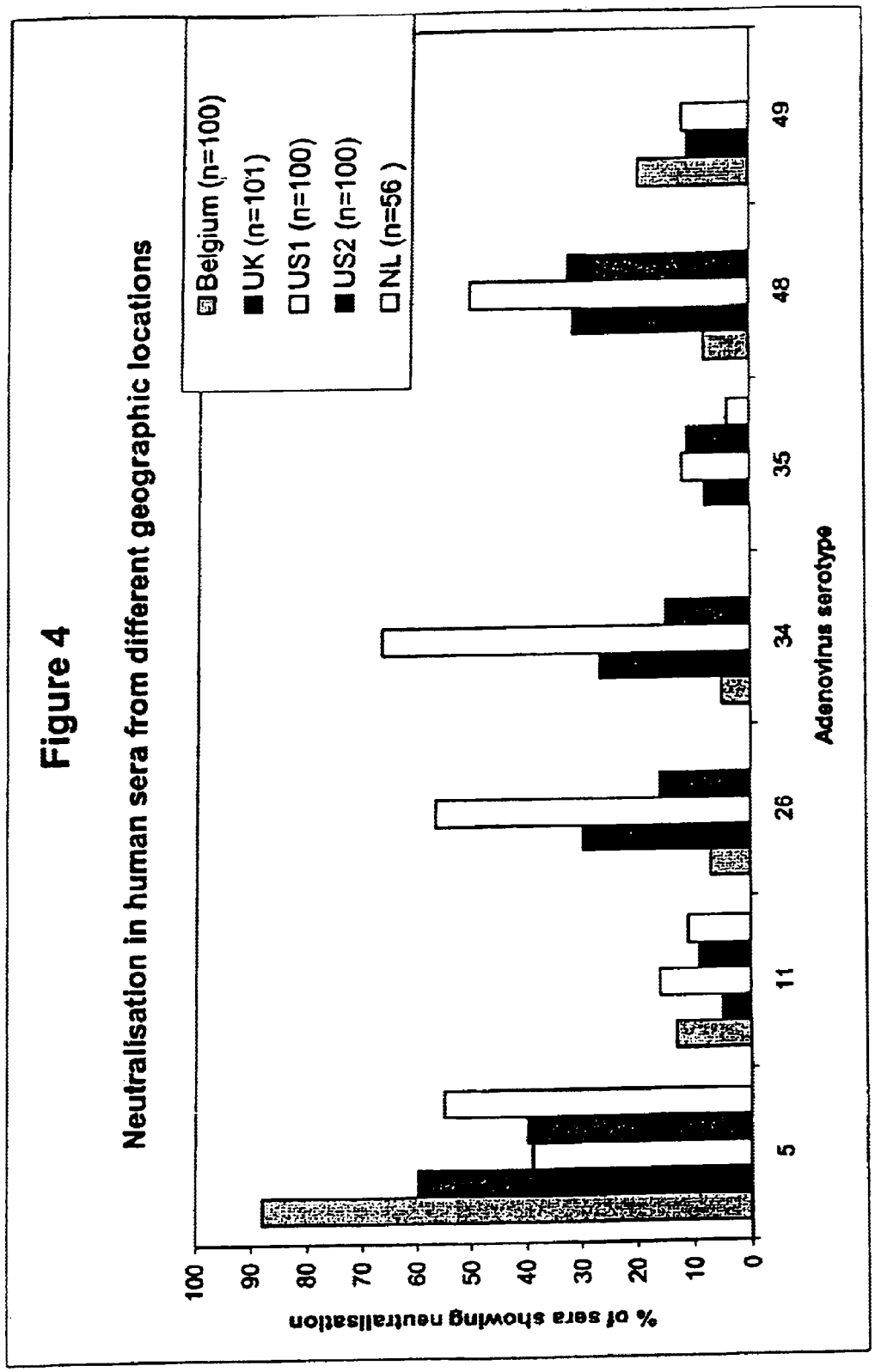

FIG. 4: Bar graph presenting the percentage sera samples that show neutralizing activity to adenovirus serotypes 5, 11, 26, 34, 35, 48 and 49. Sera were derived from five different locations in Europe and the United States.

Figure 5:
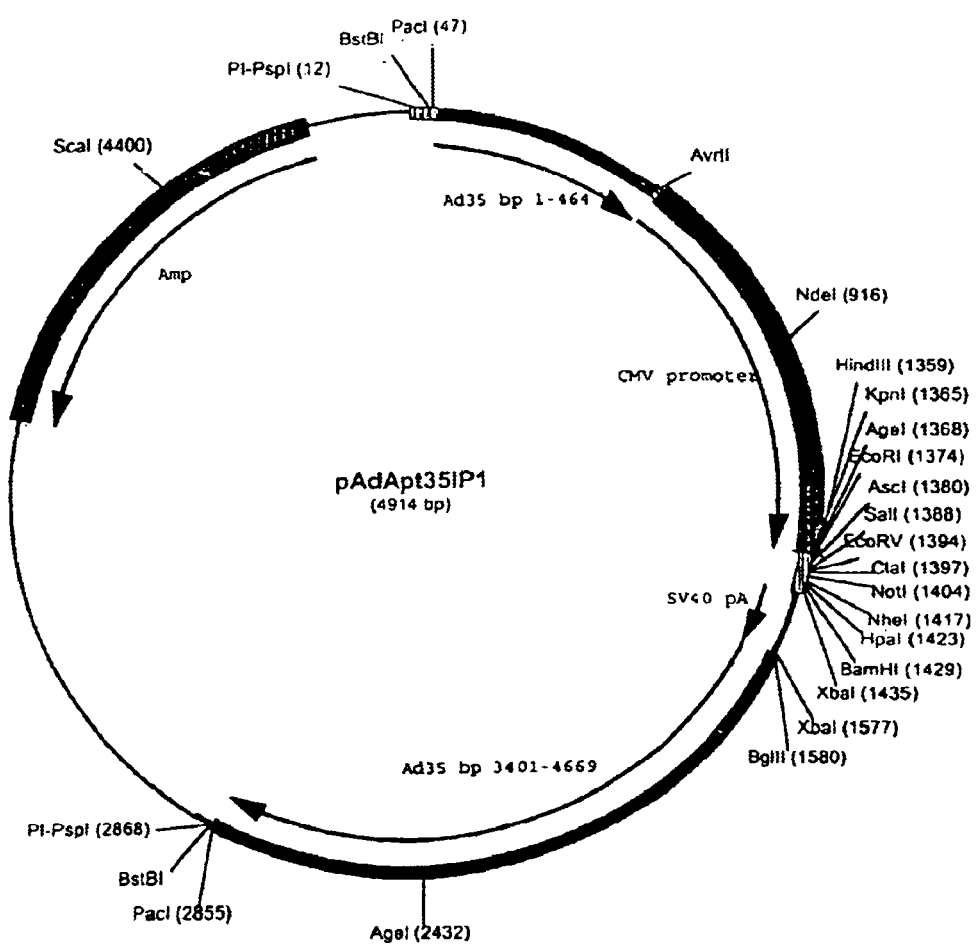

FIG. 5: Map of pAdApt35IP1.

Figure 6:
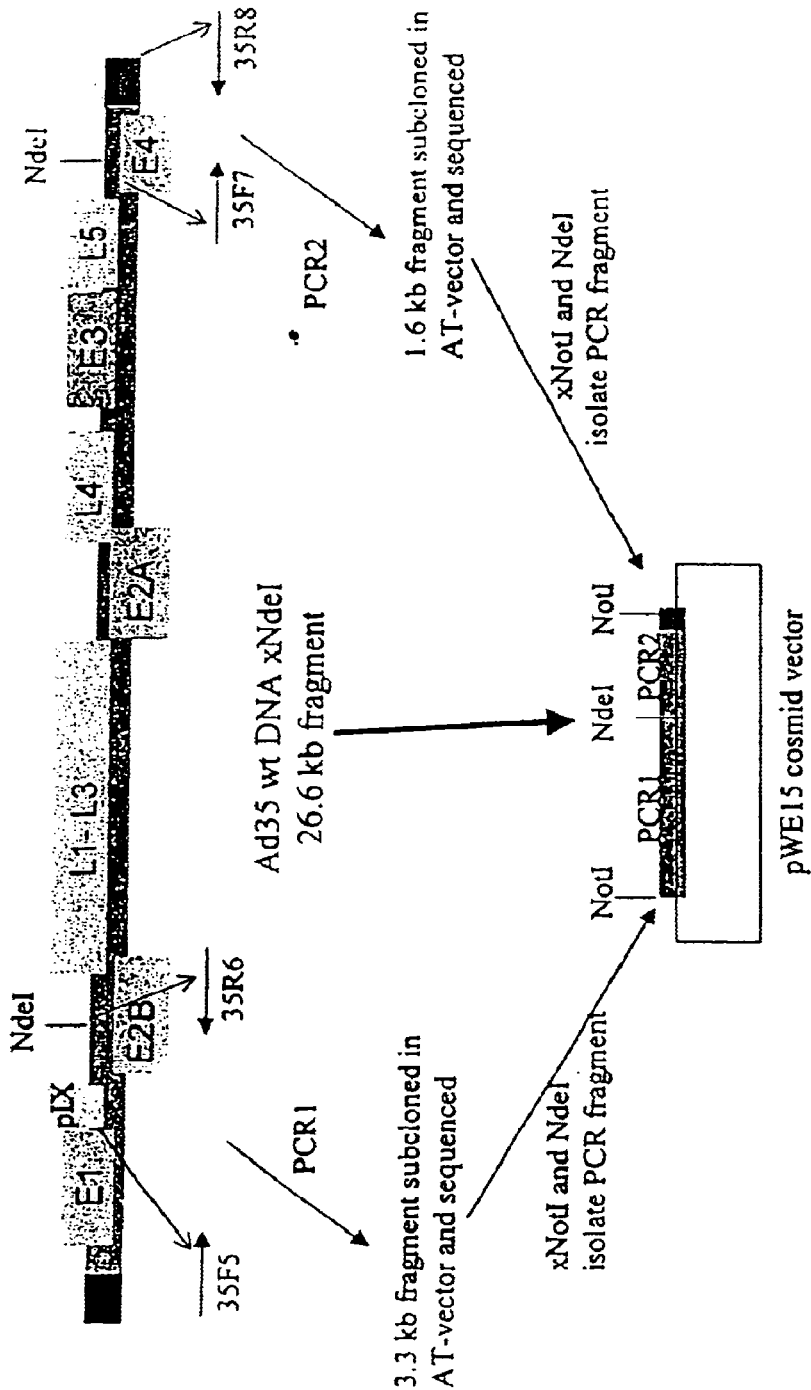

FIG. 6: Schematic representation of the steps undertaken to construct pWE.Ad35.pIX-rITR.

Figure 7:
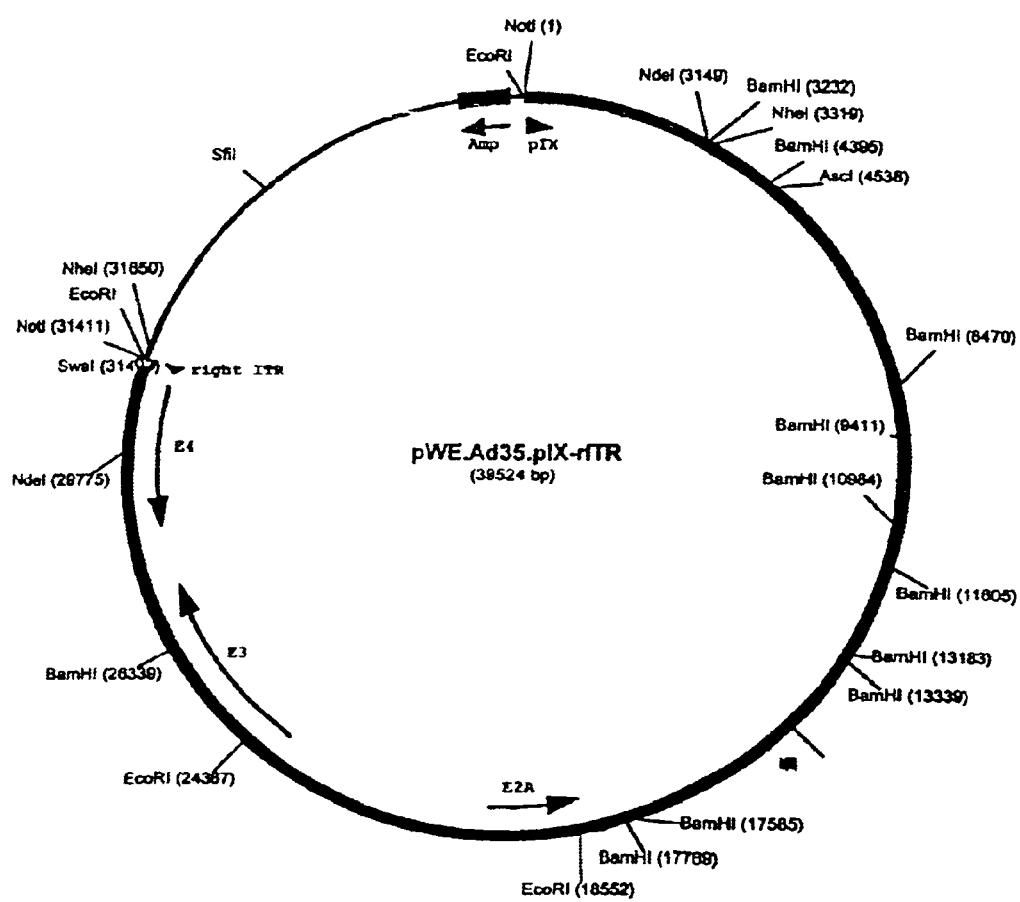

FIG. 7: Map of pWE.Ad35.pIX-rITR.

Figure 8:
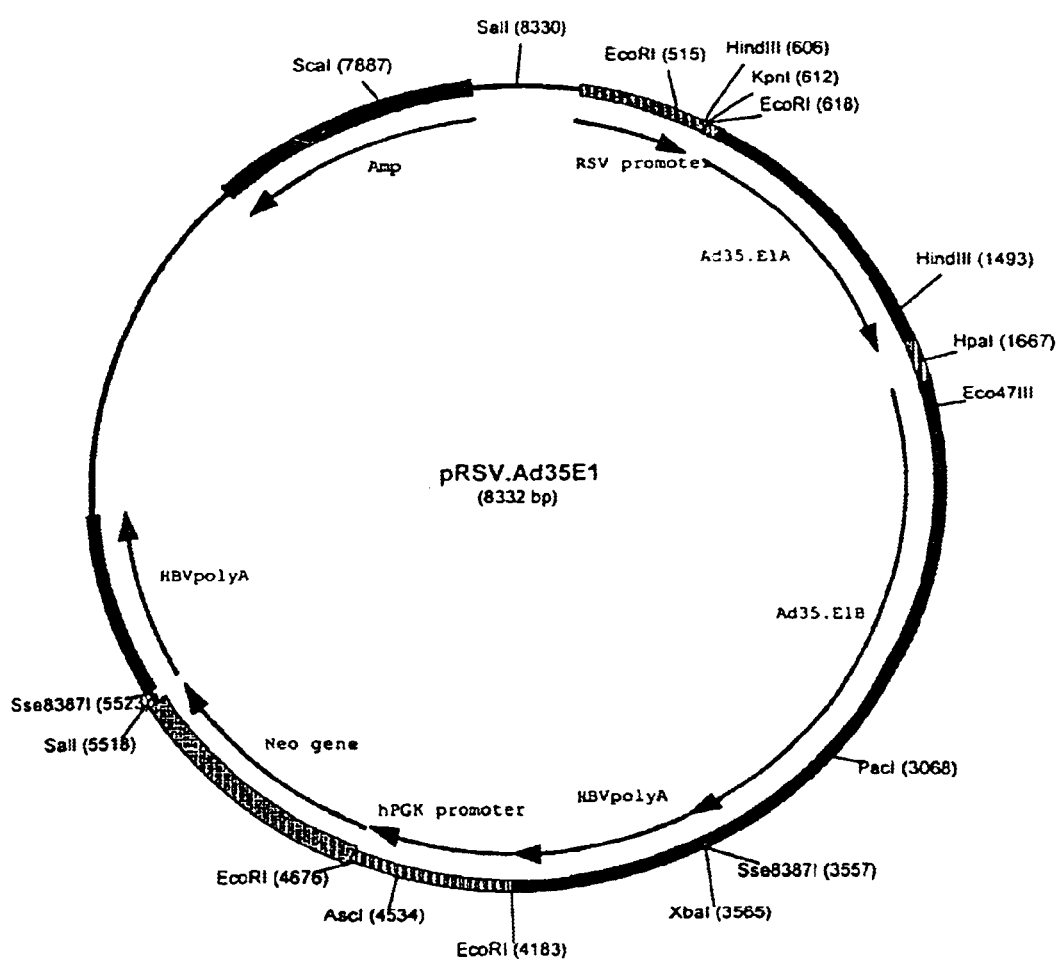

FIG. 8: Map of pRSV.Ad35-E1.

Figure 9:
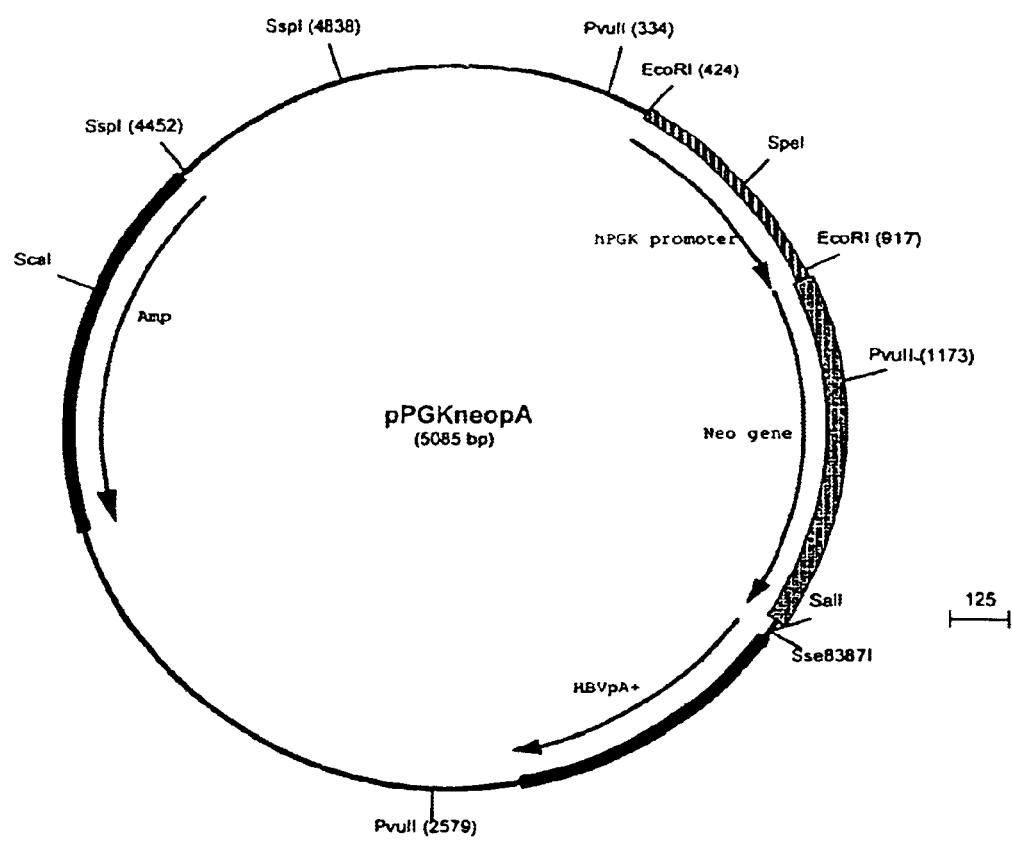

FIG. 9 Map of pPGKneopA

Figure 10:
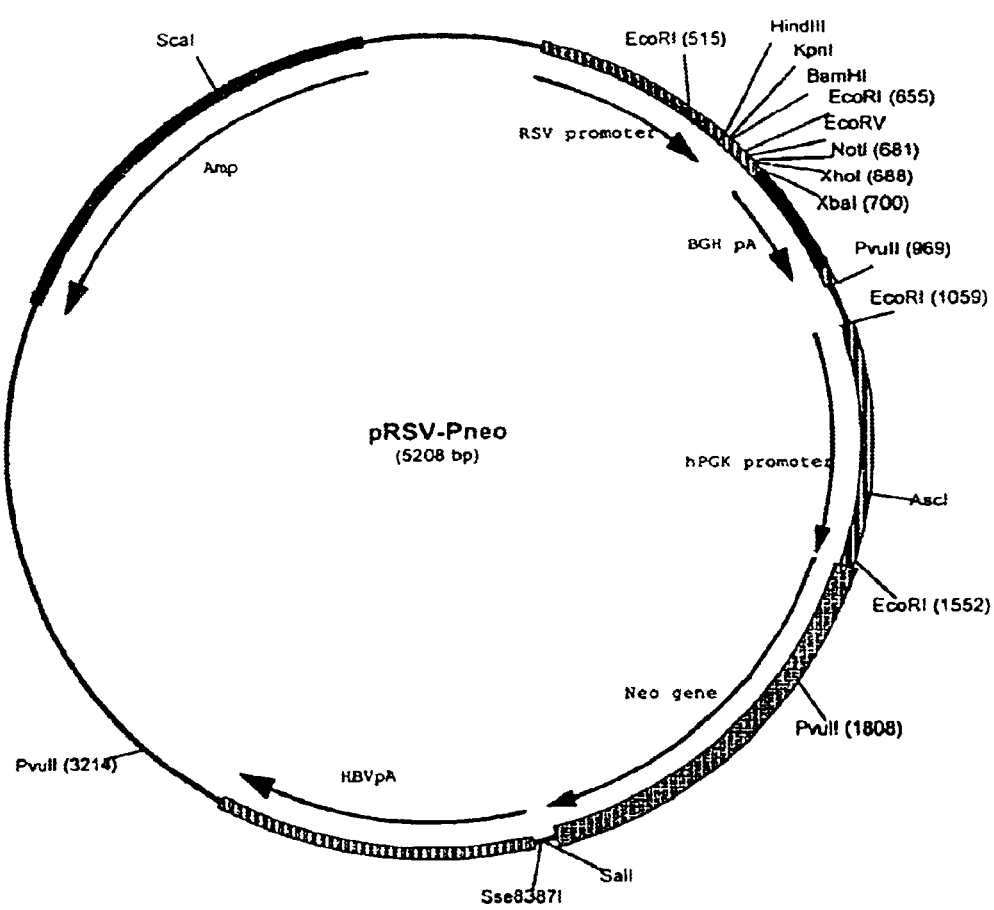

FIG. 10: Map of pRSV-Pneo.

Figure 11:
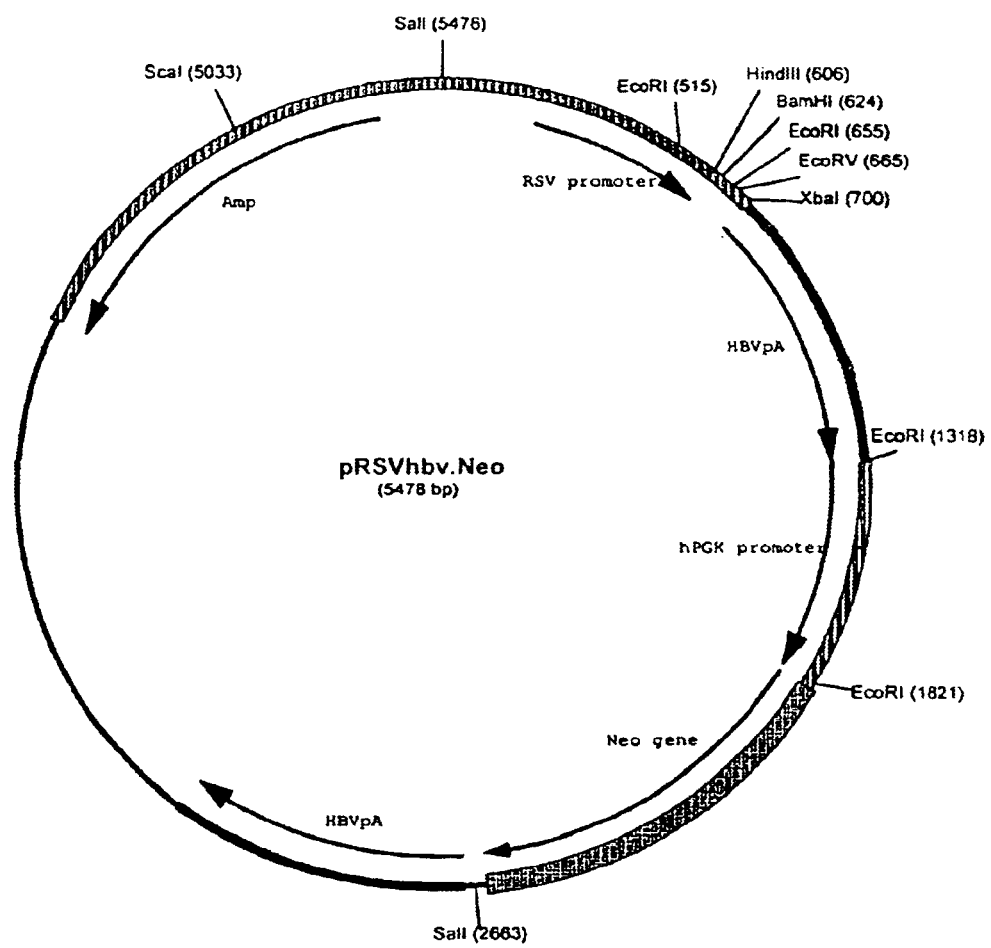

FIG. 11: Map of pRSVhbv.Neo.

Figure 12:
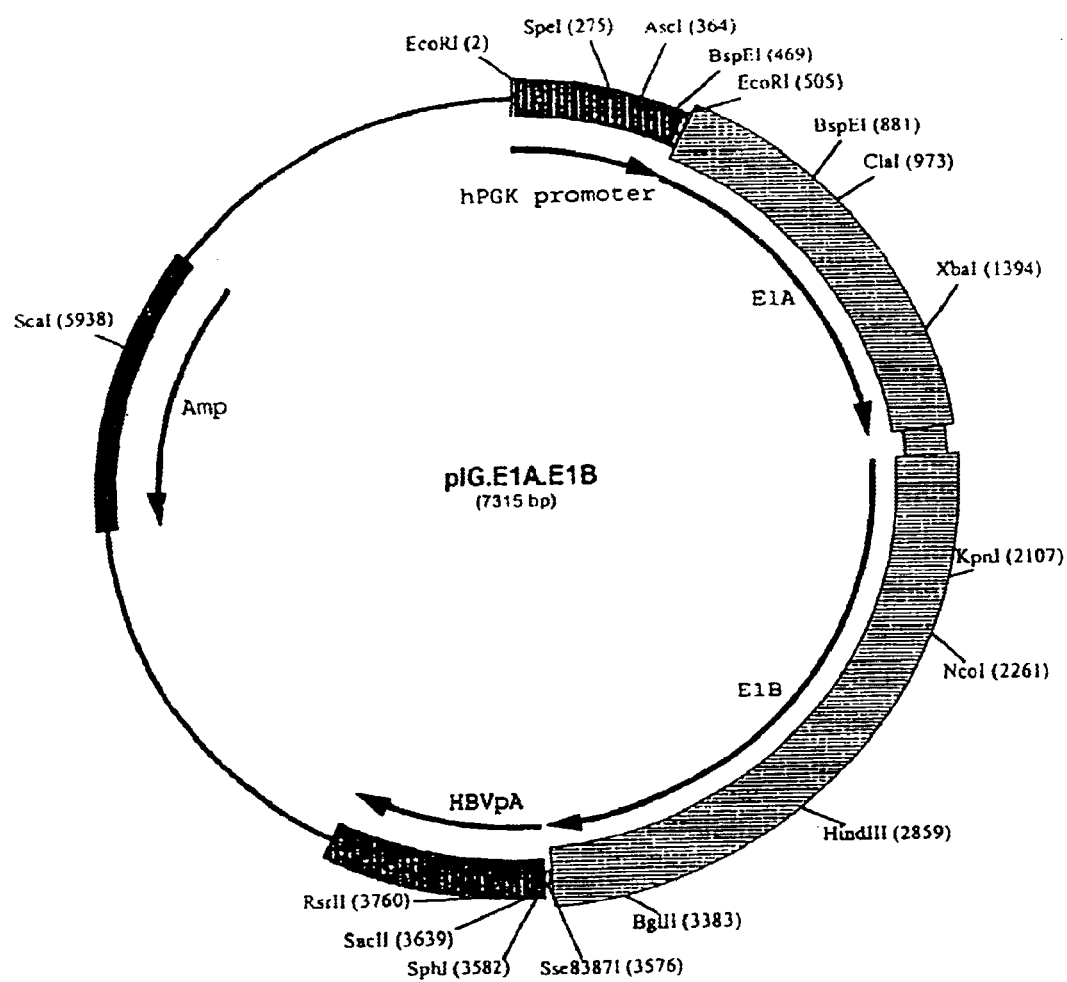

FIG. 12: Map of pIG.E1A.E1B.

Figure 13:
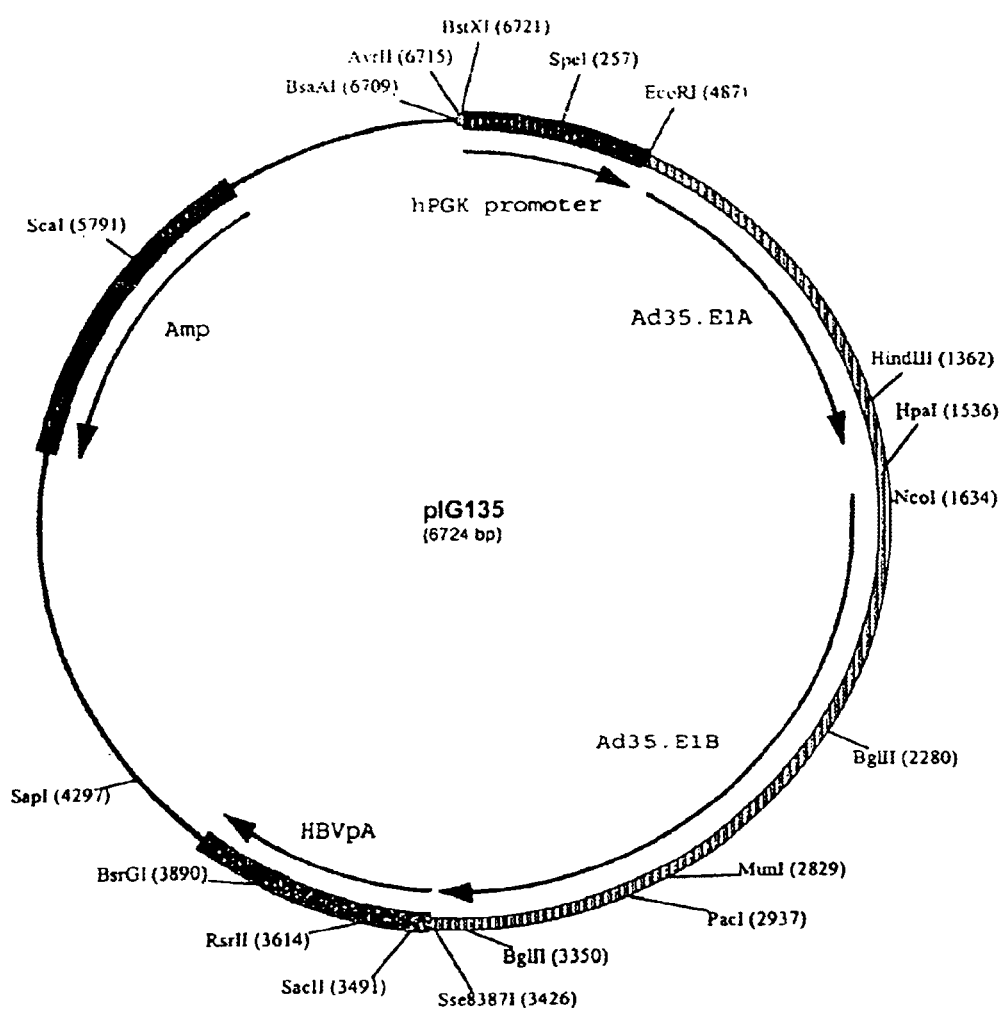

FIG. 13: Map of pIG135.

Figure 14:
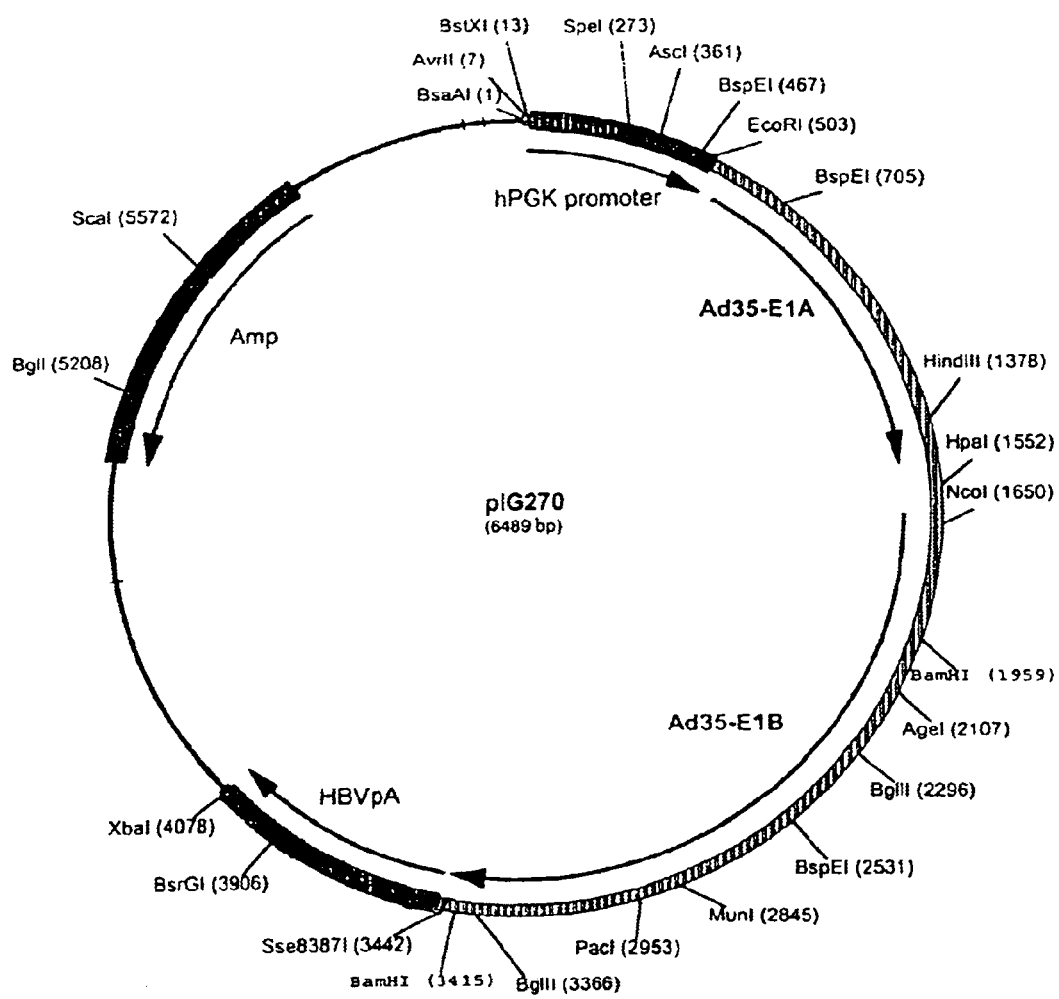

FIG. 14: Map of pIG270.

Figure 15:
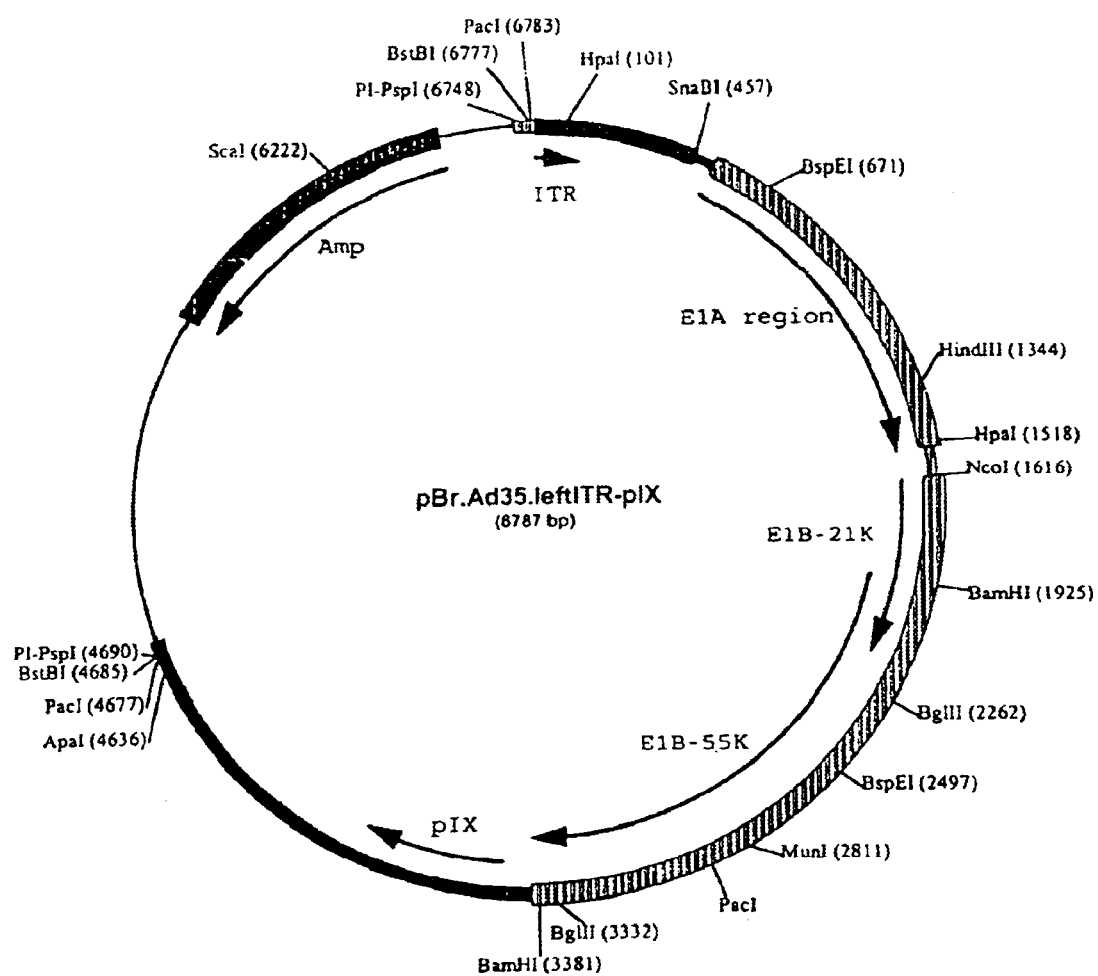

FIG. 15: Map of pBr.Ad35.leftITR-pIX.

Figure 16:
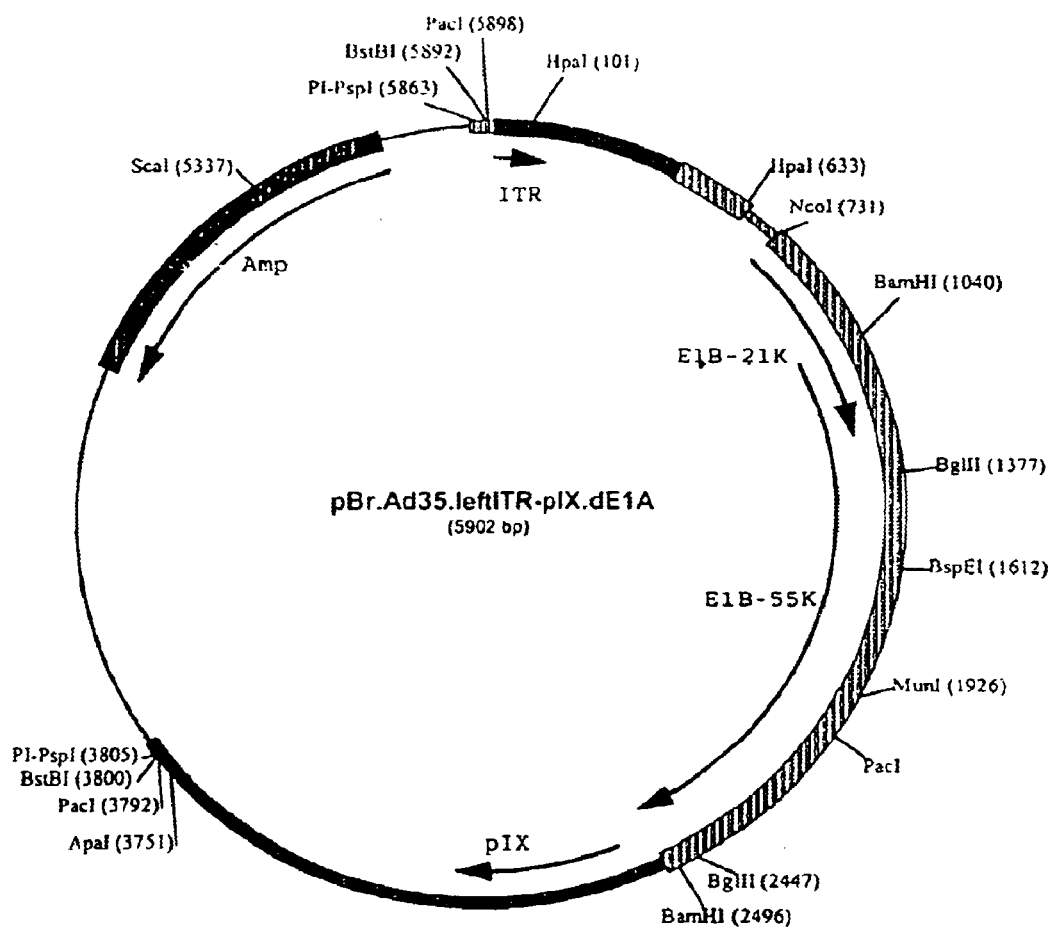

FIG. 16: Map of pBr.Ad35.leftITR-pIXdE1A.

Figure 17:
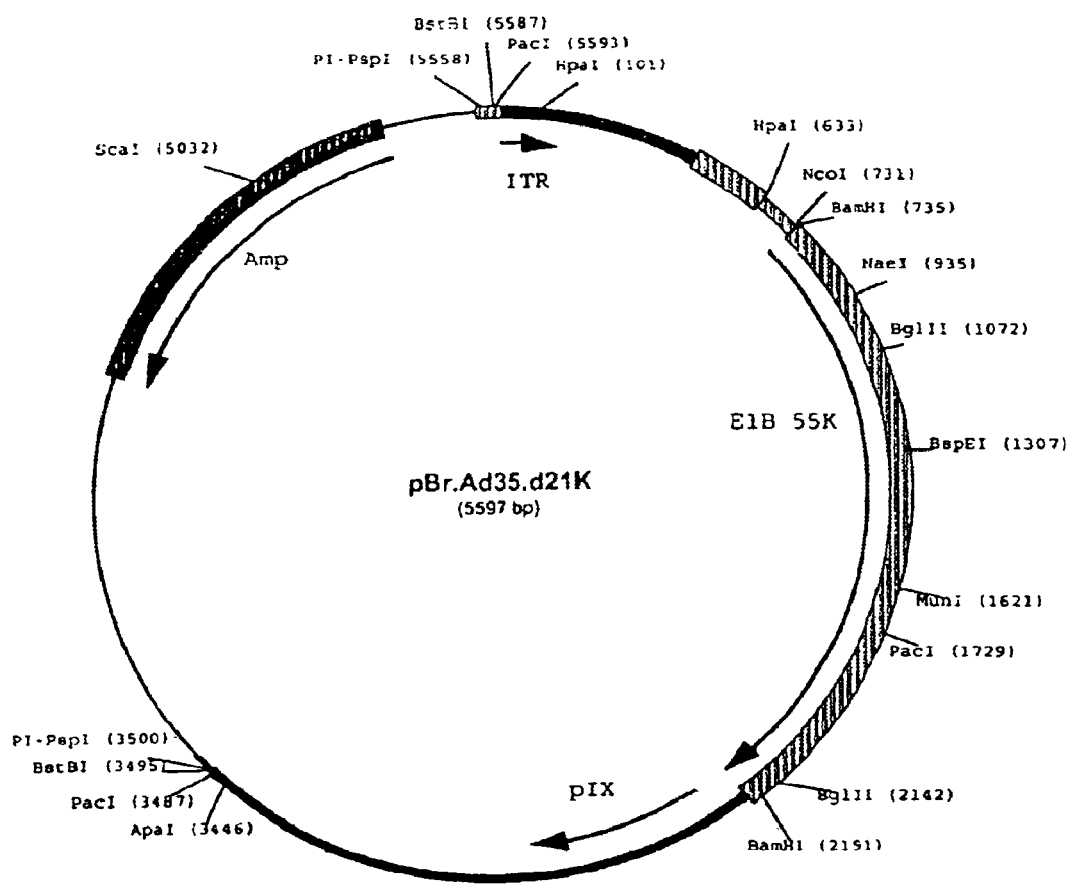

FIG. 17: Map of pBr.Ad35.d21K.

Figure 18:
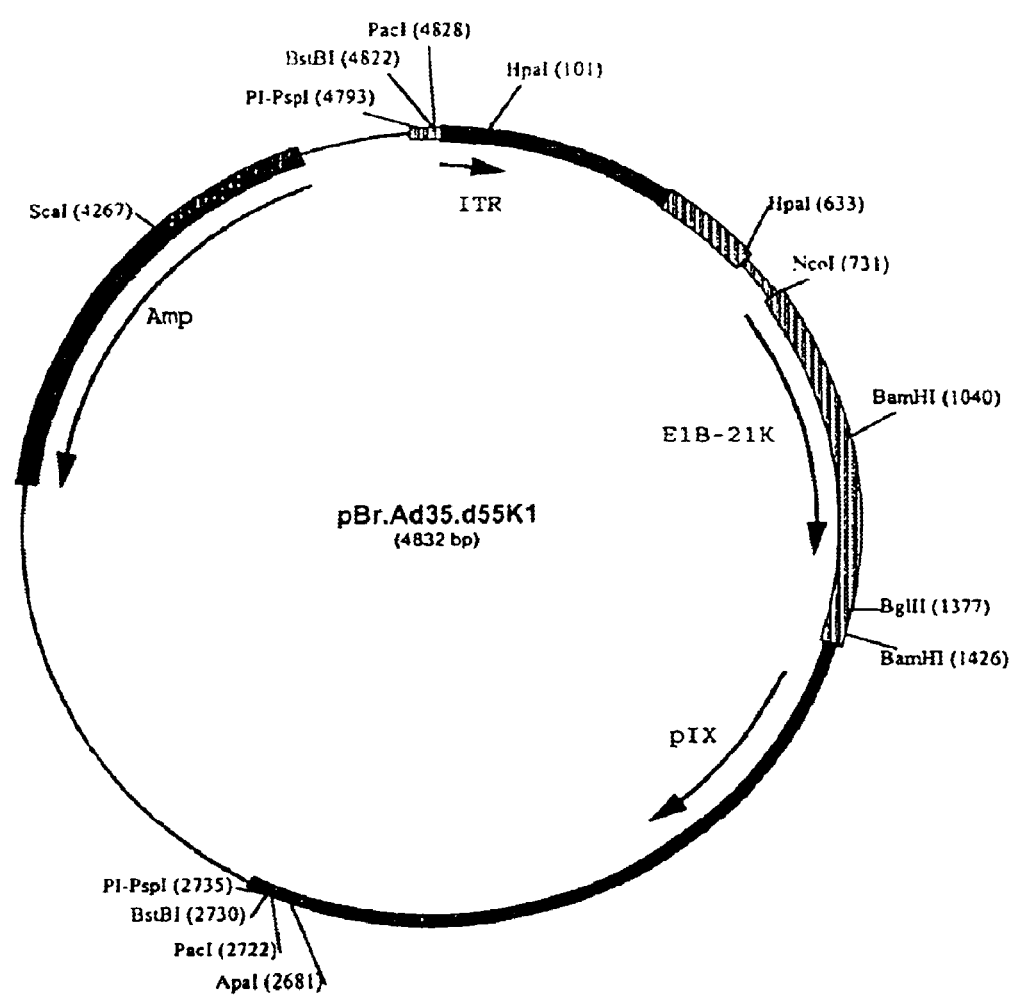

FIG. 18: Map of pBr.Ad35.d55K1.

Figure 19:
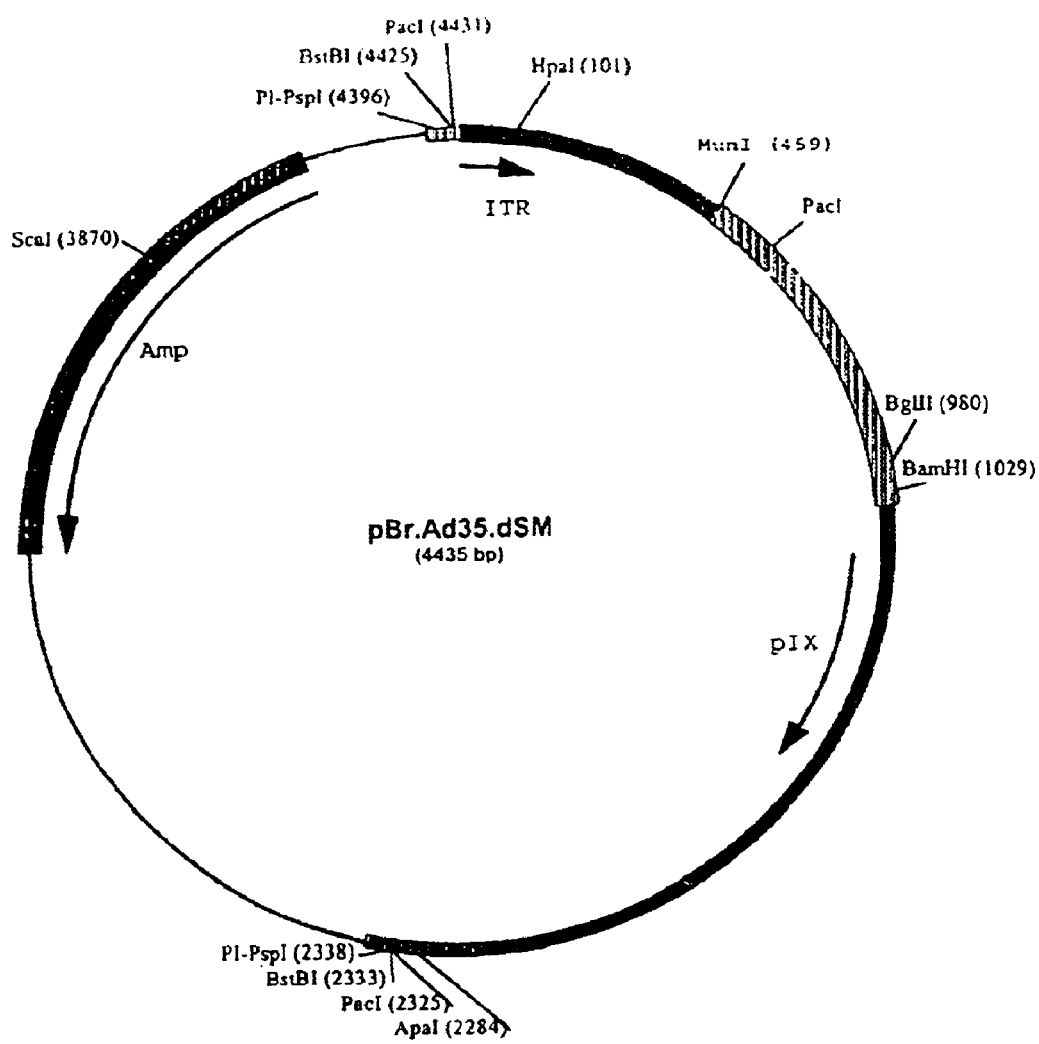

FIG. 19: Map of pBr.Ad35DdSM.

Figure 20:
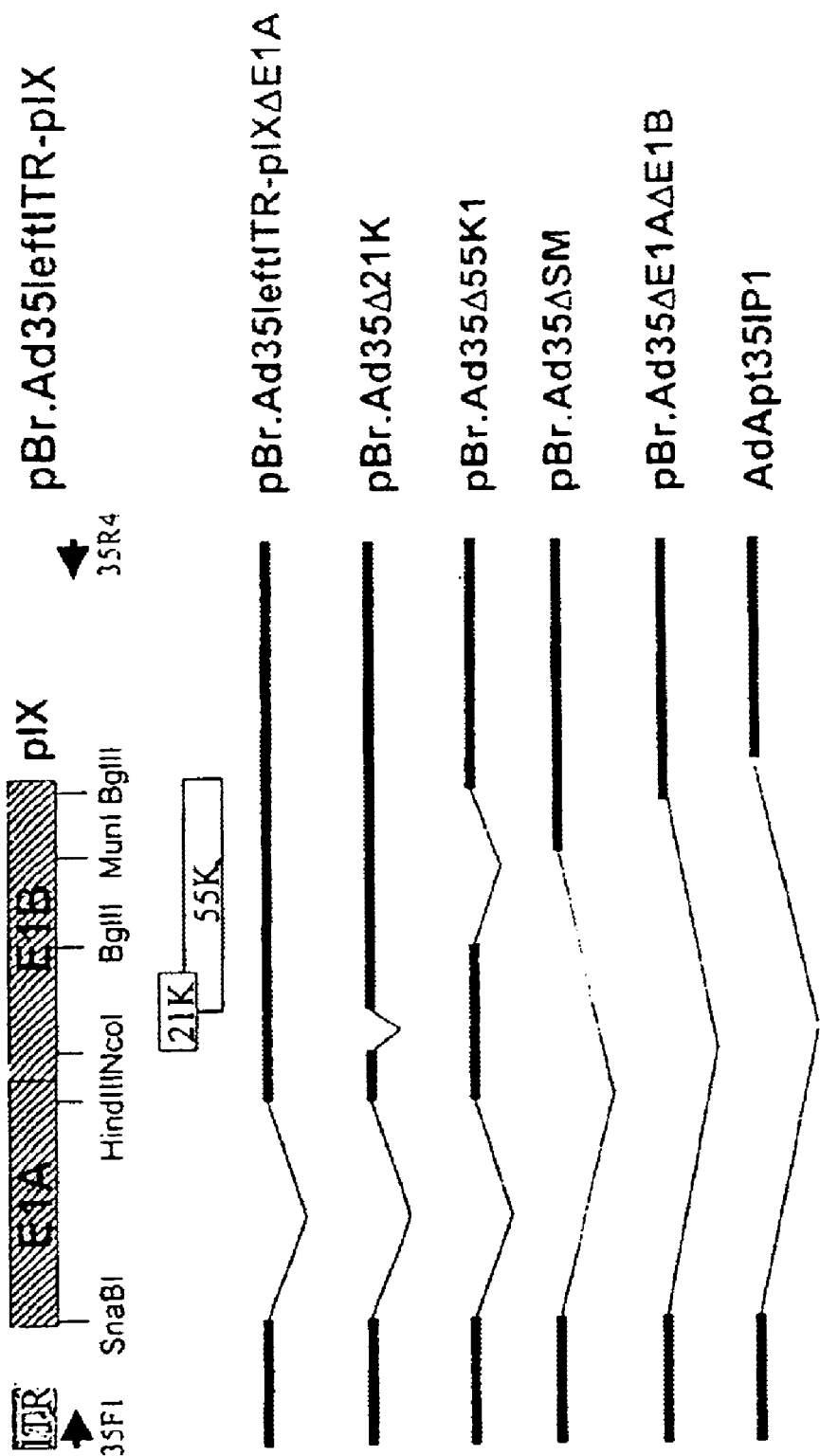

FIG. 20: Schematic representation of Ad35-E1A1E1B deletion constructs.

Figure 21:
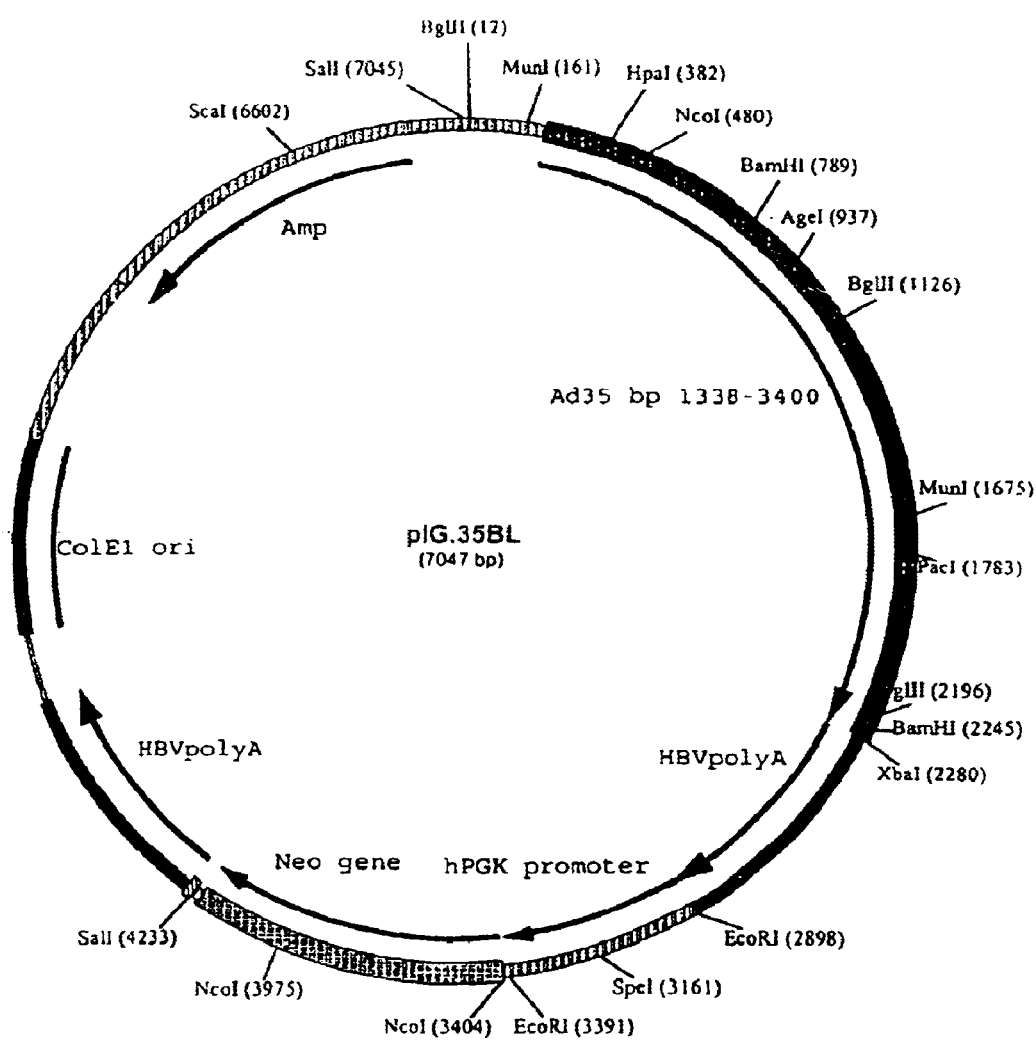

FIG. 21: Map of pIG.35BL.

Figure 22:
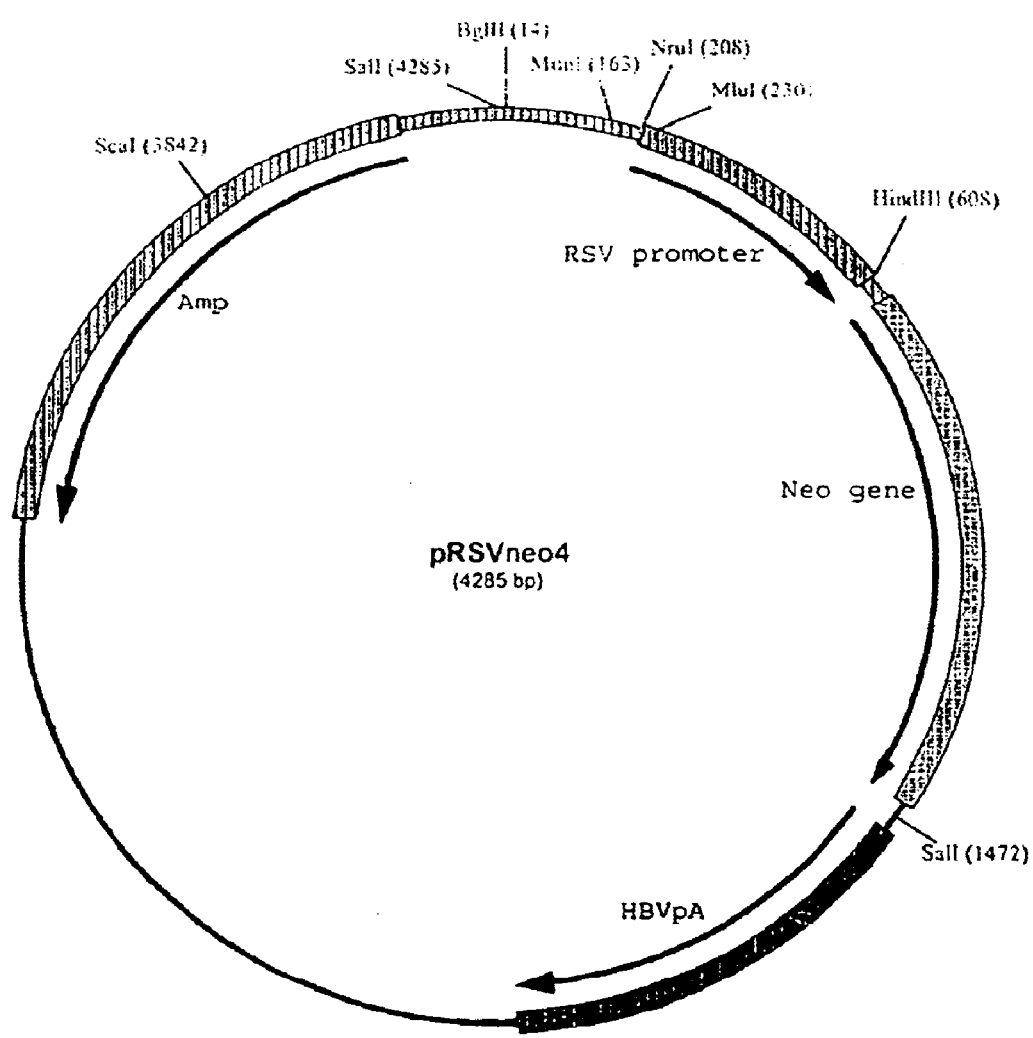

FIG. 22: Map of pRSVneo4.

Figure 23:
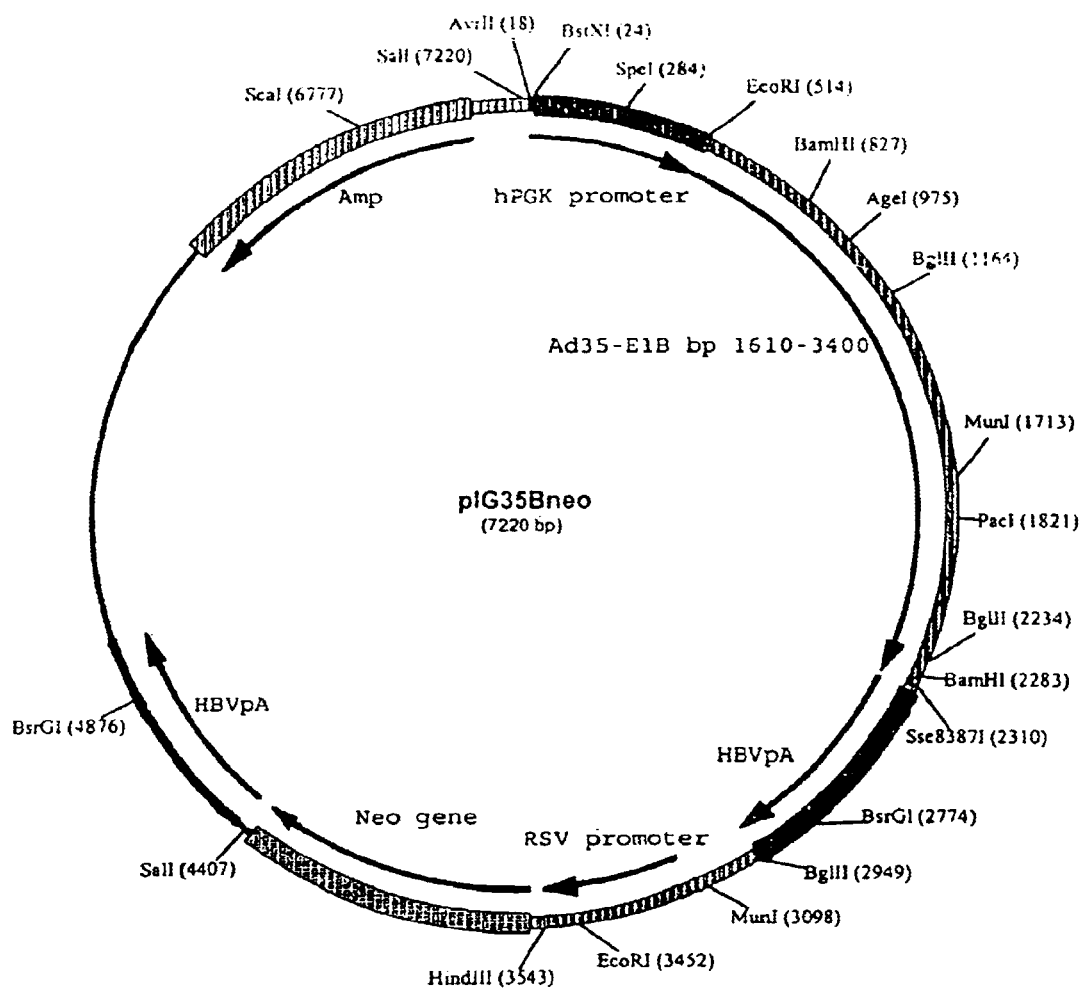

FIG. 23: Map of pIG35Bneo.

Figure 24:
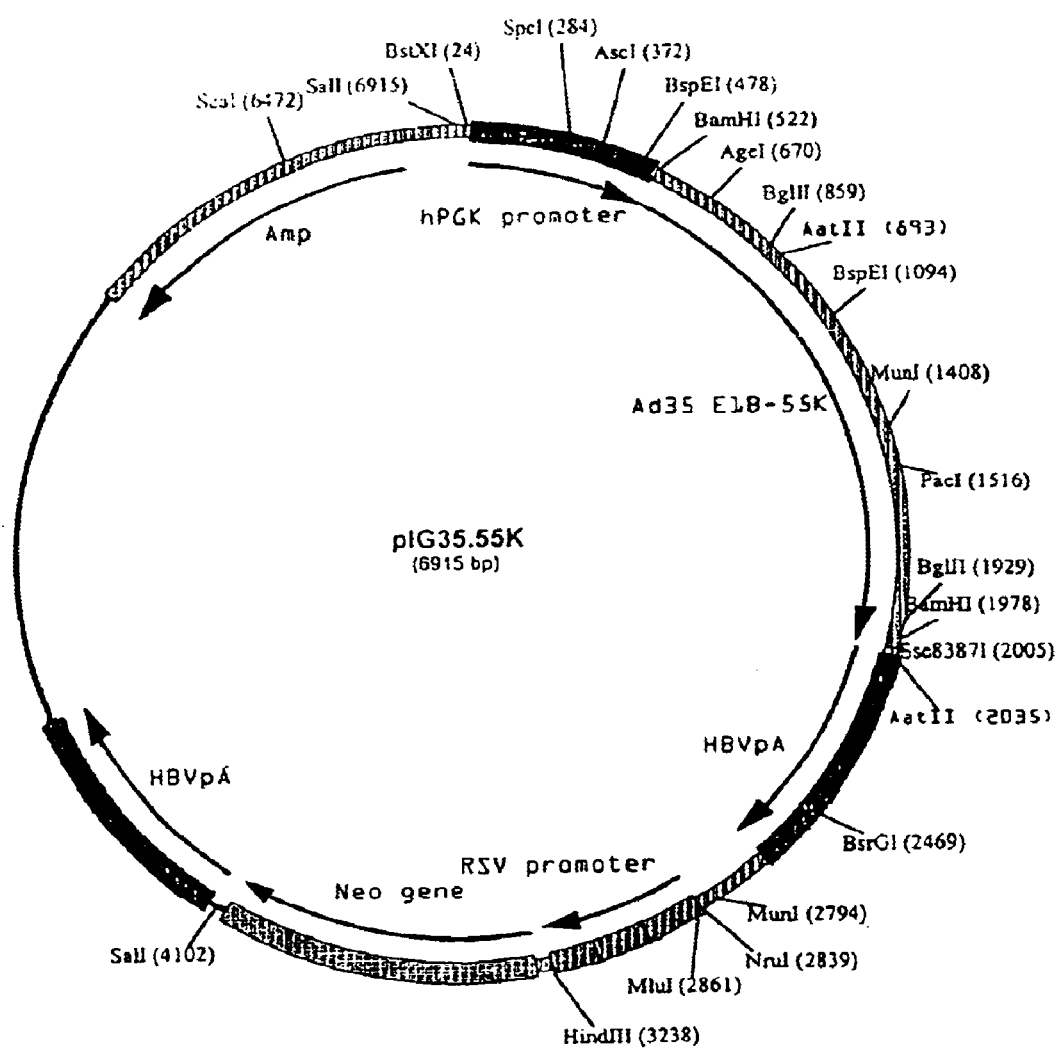

FIG. 24: Map of pIG35.55K.

Figure 25:
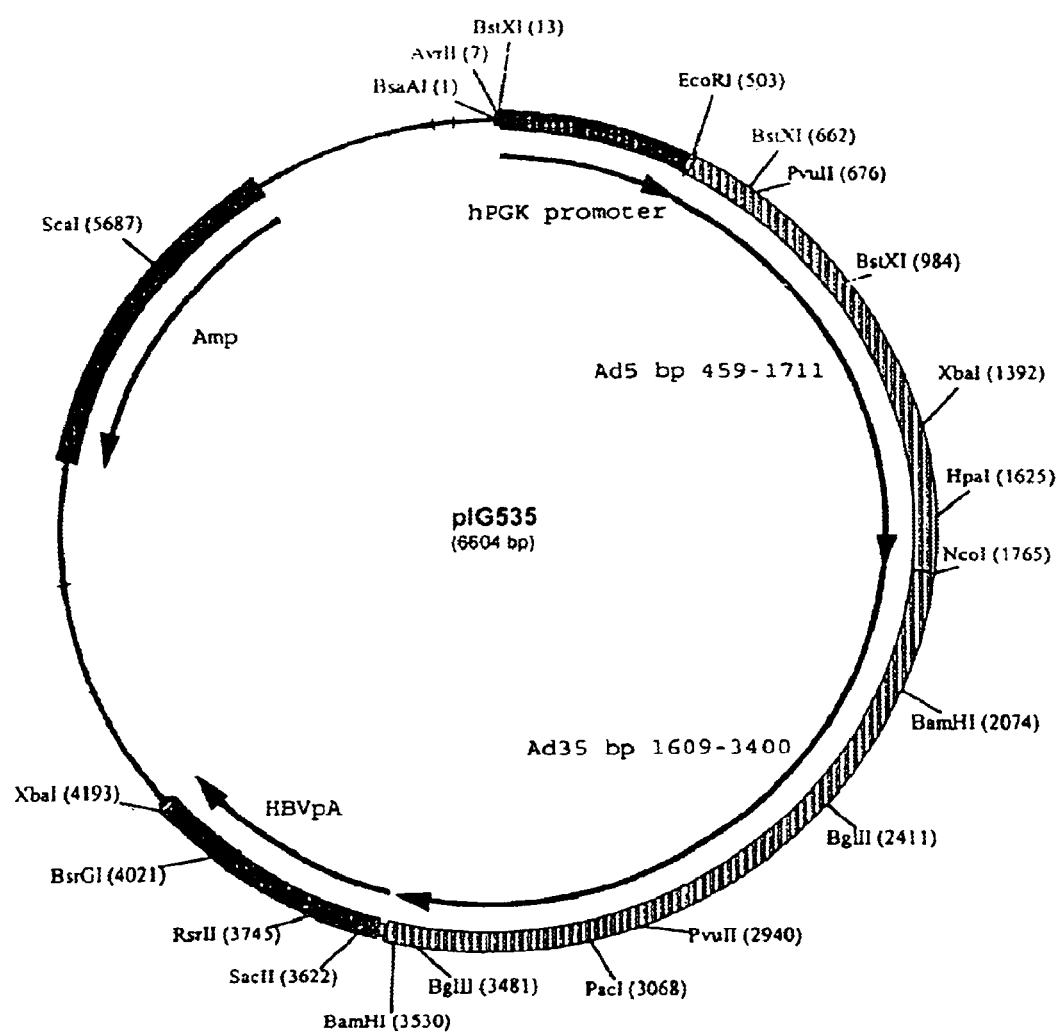

FIG. 25: Map of pIG535.

Figure 26:
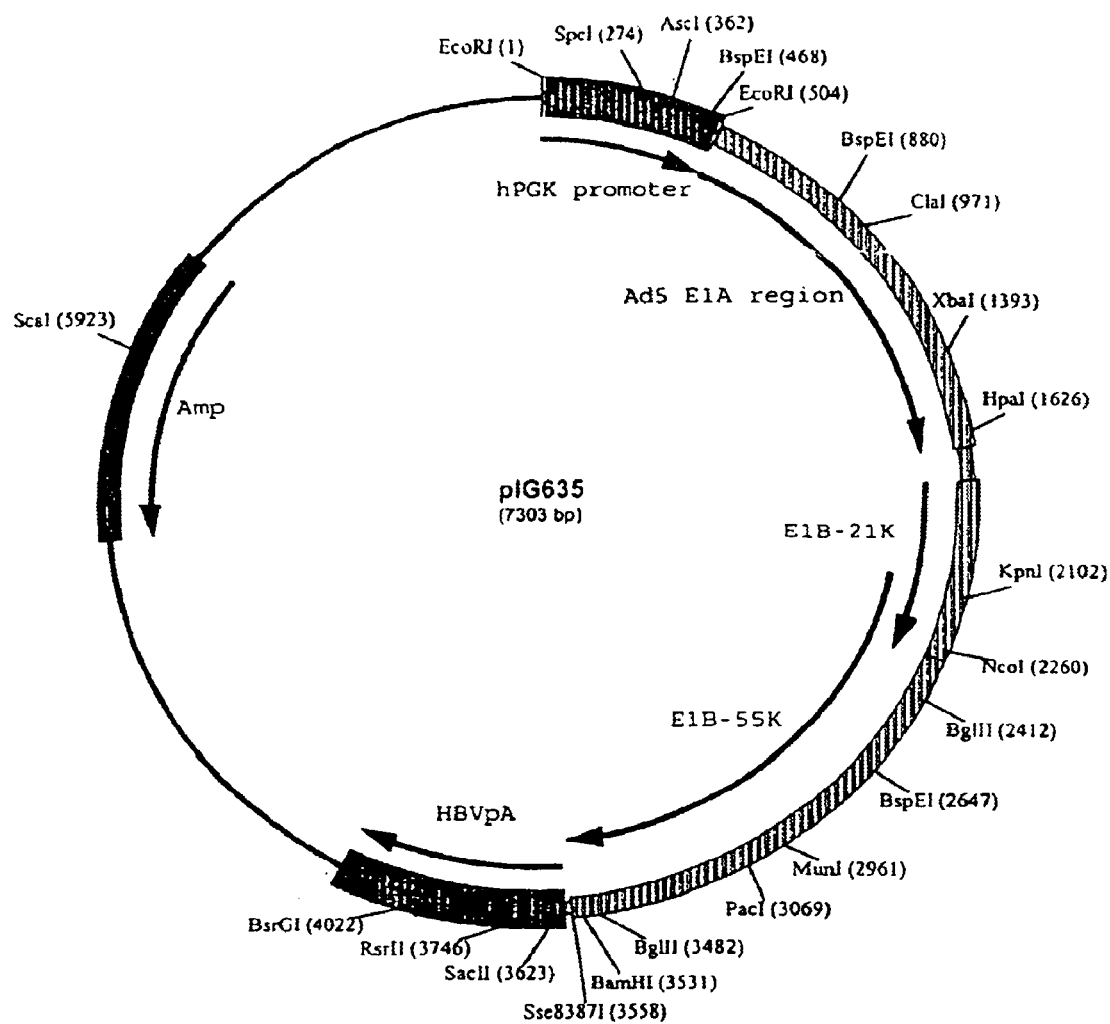

FIG. 26: Map of pIG635.

Figure 27:
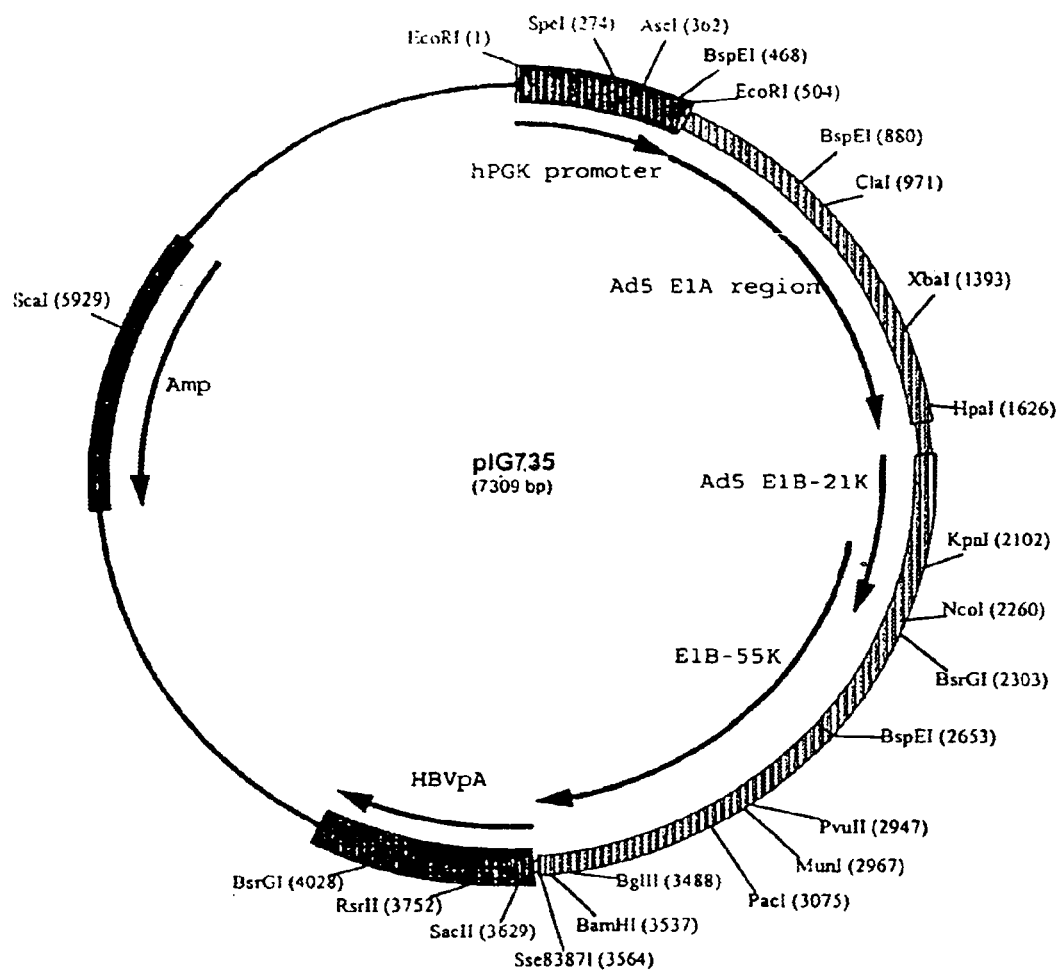

FIG. 27: Map of pIG735.

Figure 28:
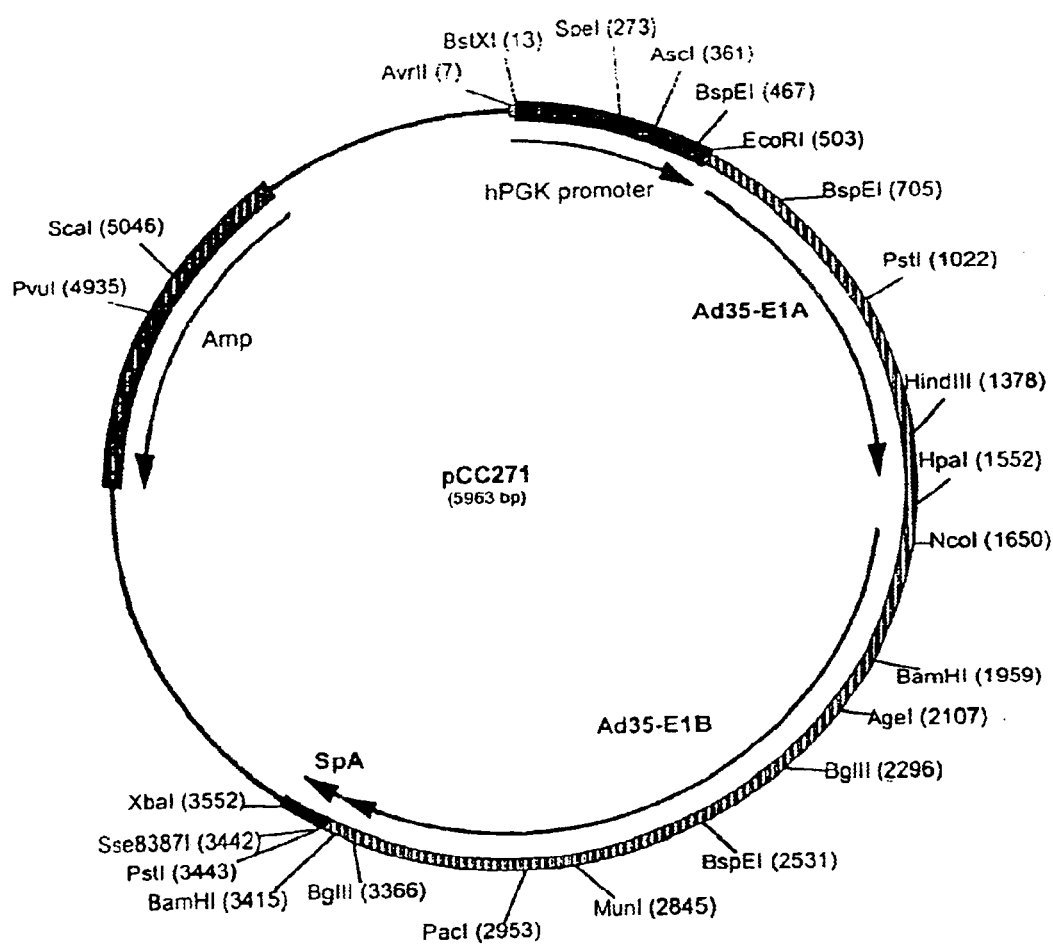

FIG. 28: Map of pCC271.

Figure 29:
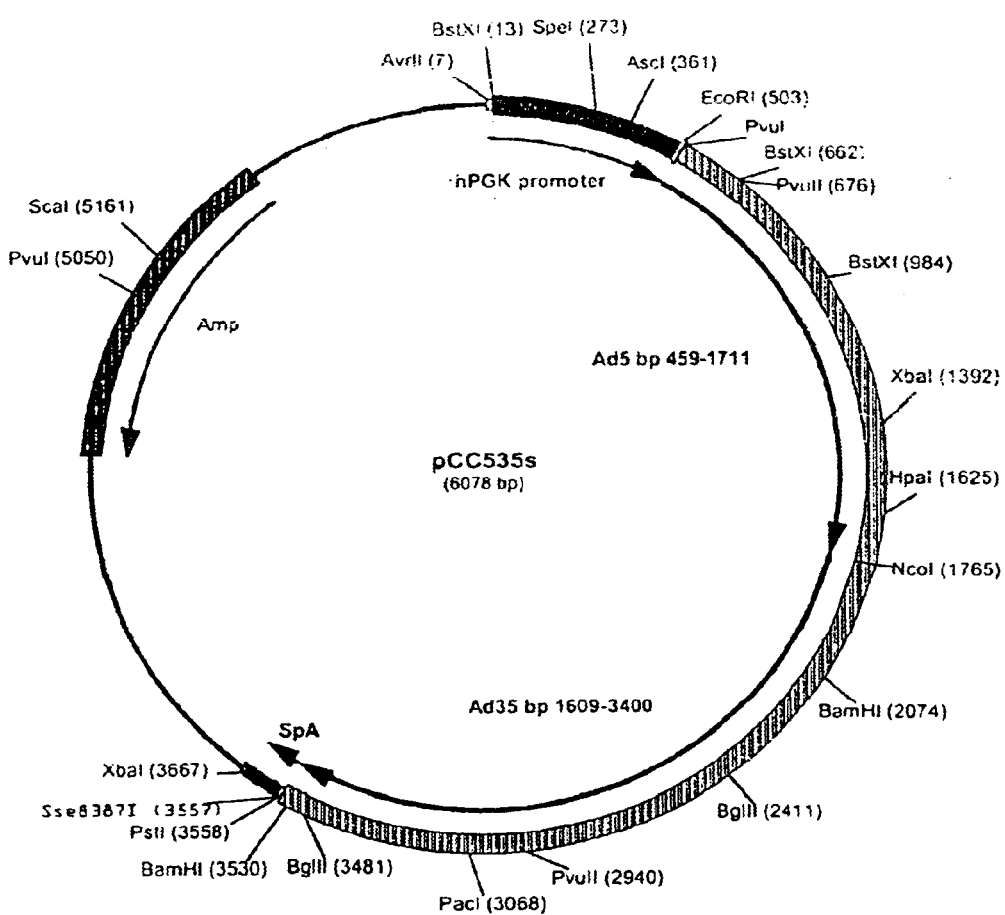

FIG. 29: Map of pCC535s.

Figure 30:
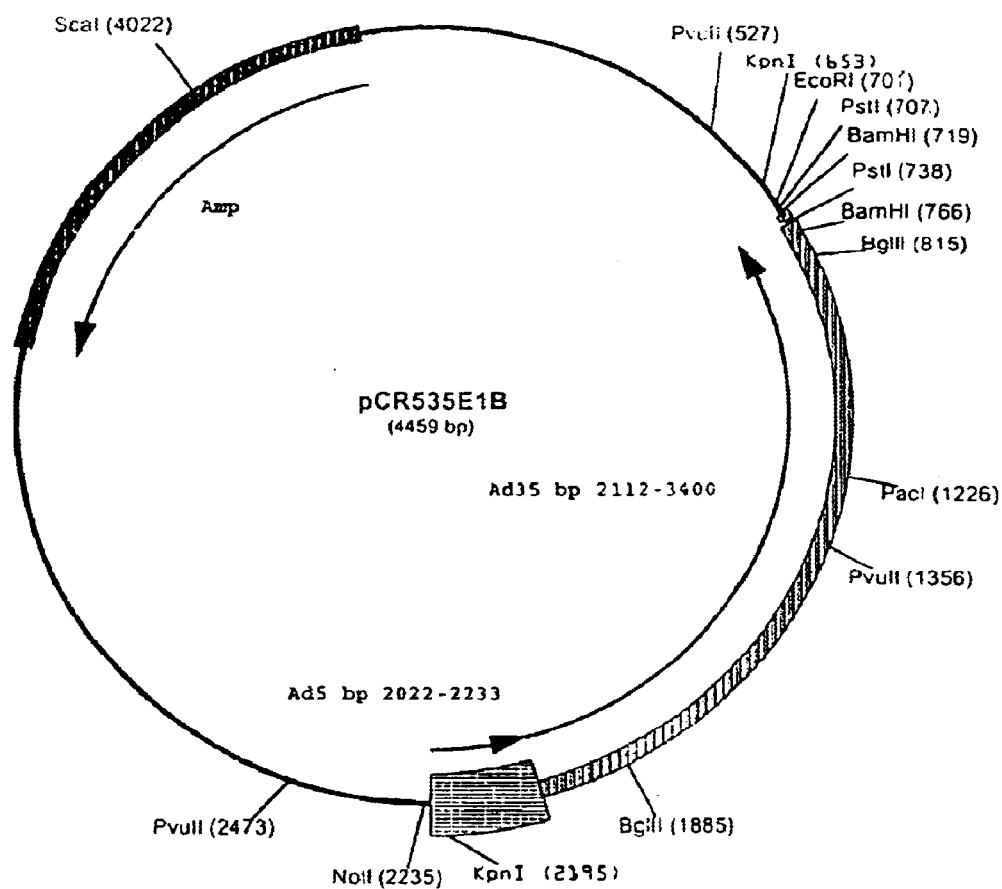

FIG. 30: Map of pCR535E1B.

Figure 31:
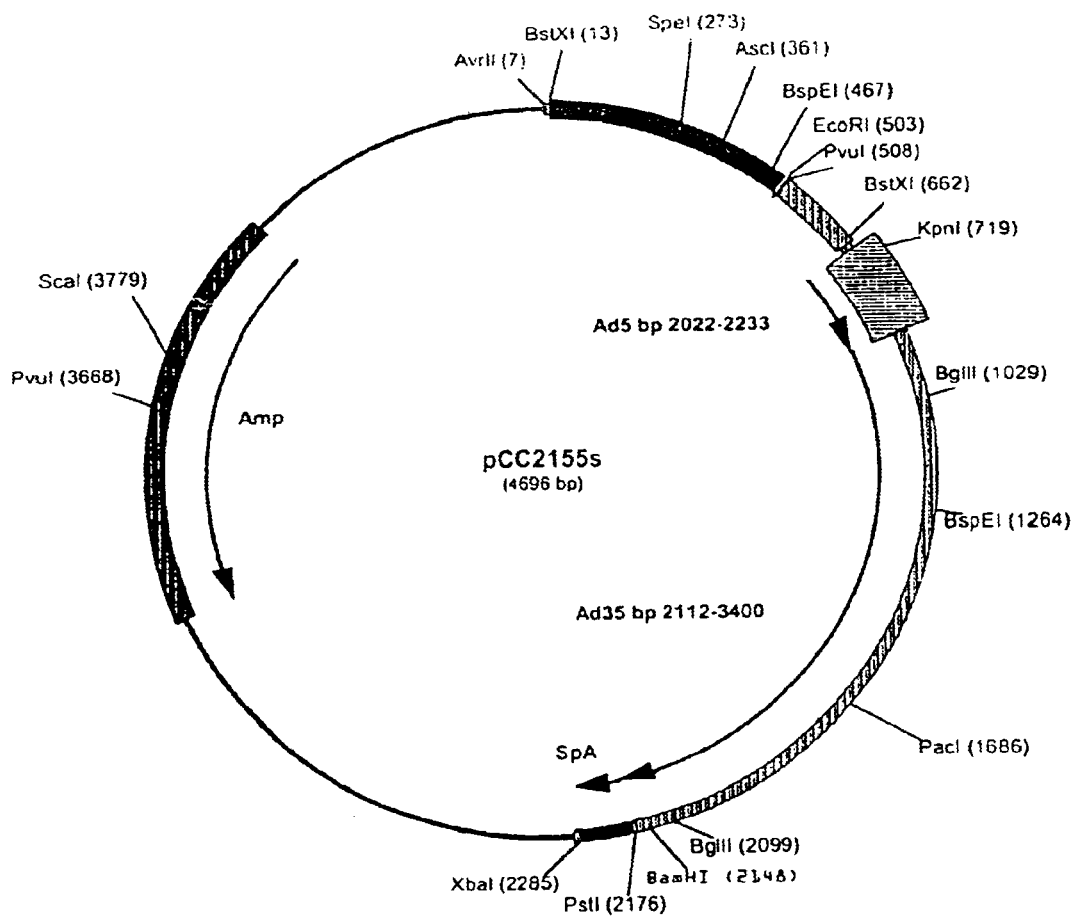

FIG. 31: Map of pCC2155s.

Figure 32:
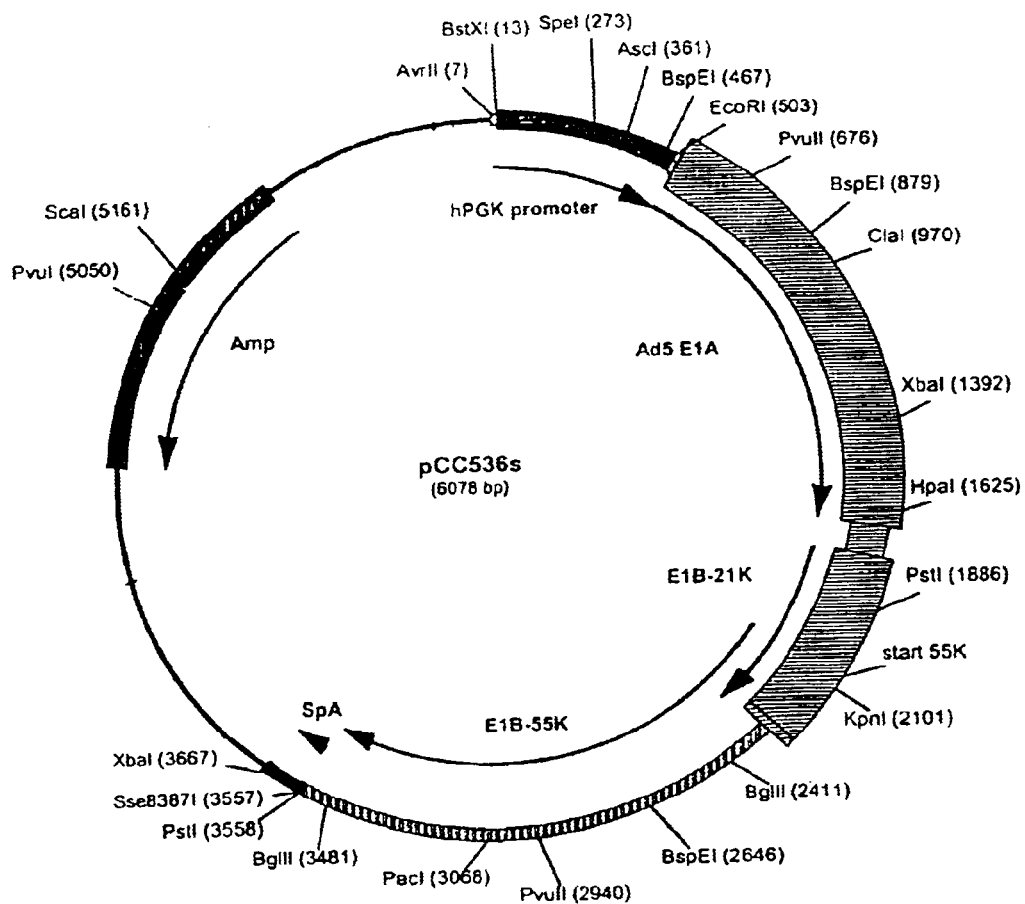

FIG. 32: Map of pCC536s.

Figure 33:
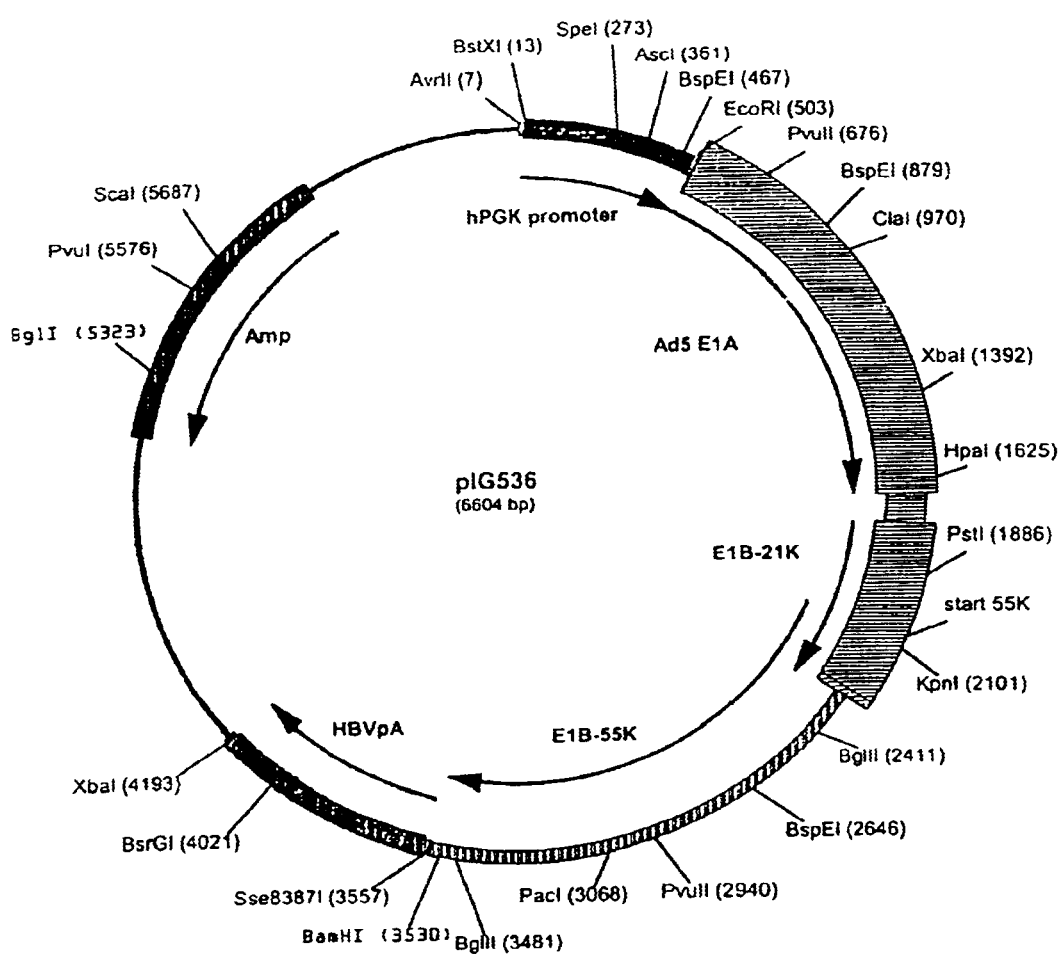

FIG. 33: Map of pIG536.

Figure 34:
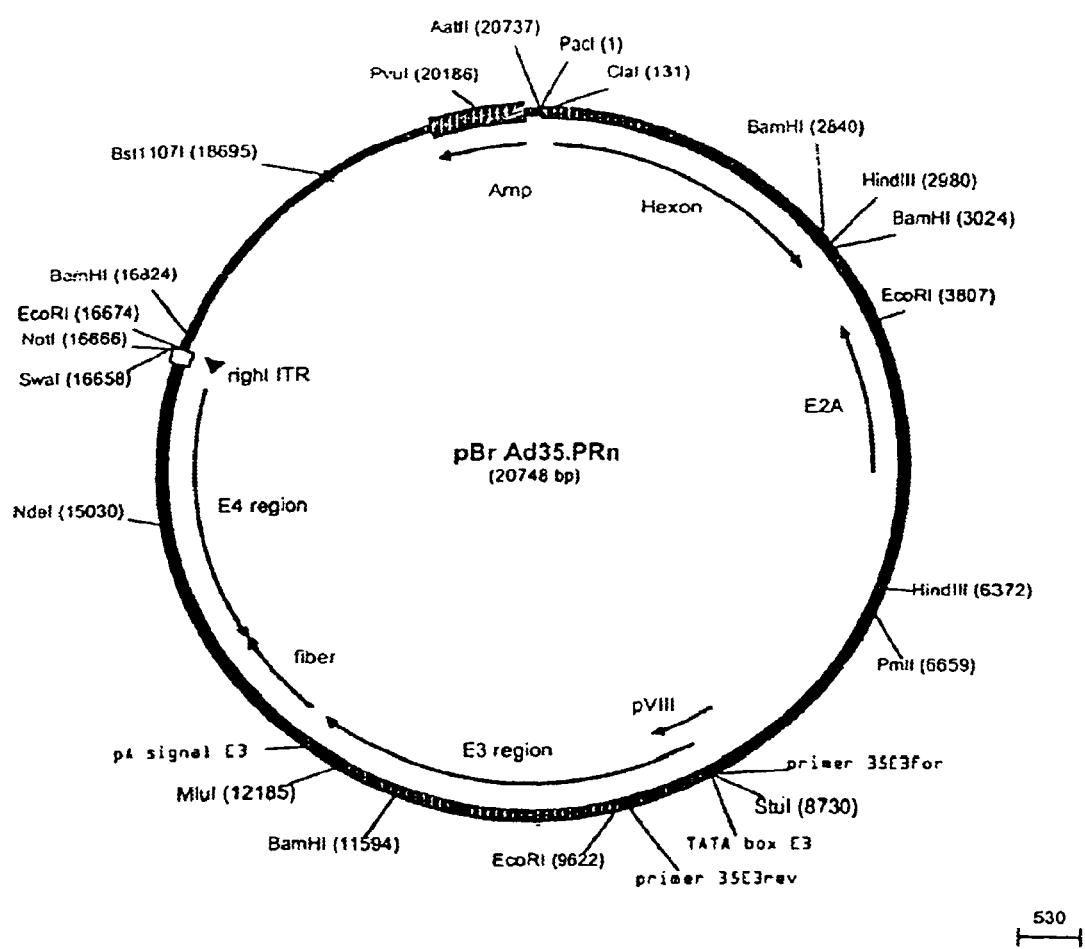

FIG. 34: Map of pBr.Ad35.PRn.

Figure 35:
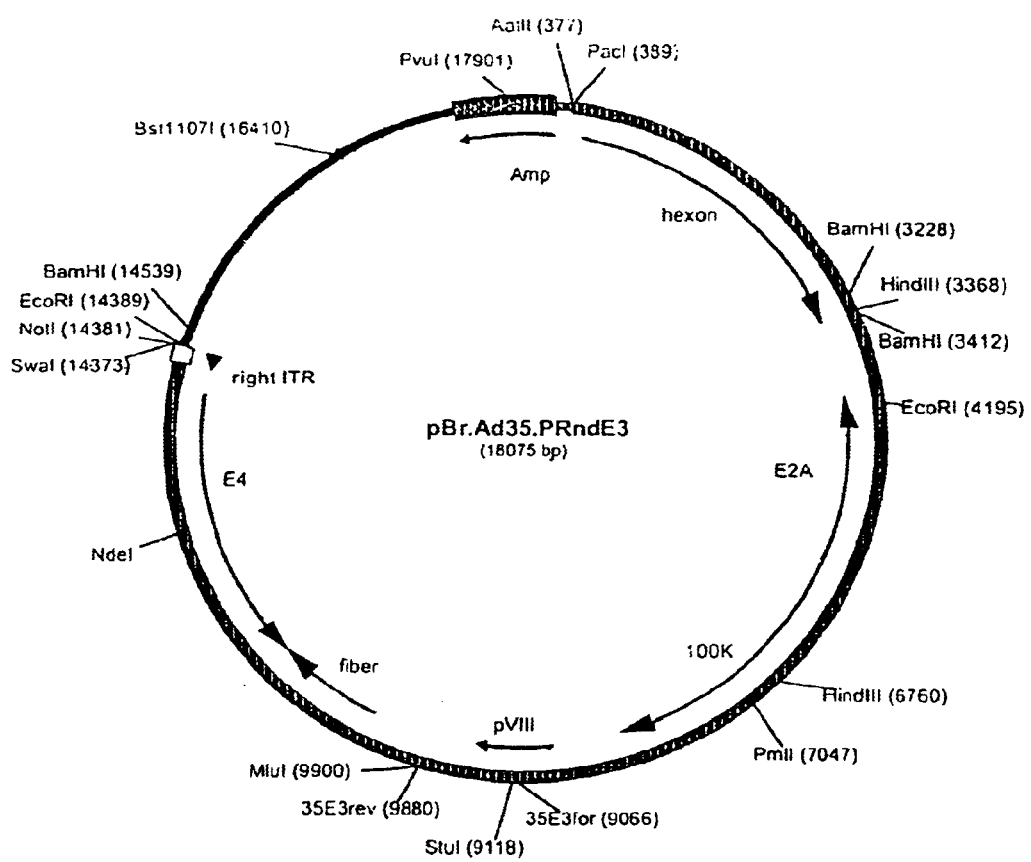

FIG. 35: Map of pBr.Ad35.PRnΔE3.

Figure 36:
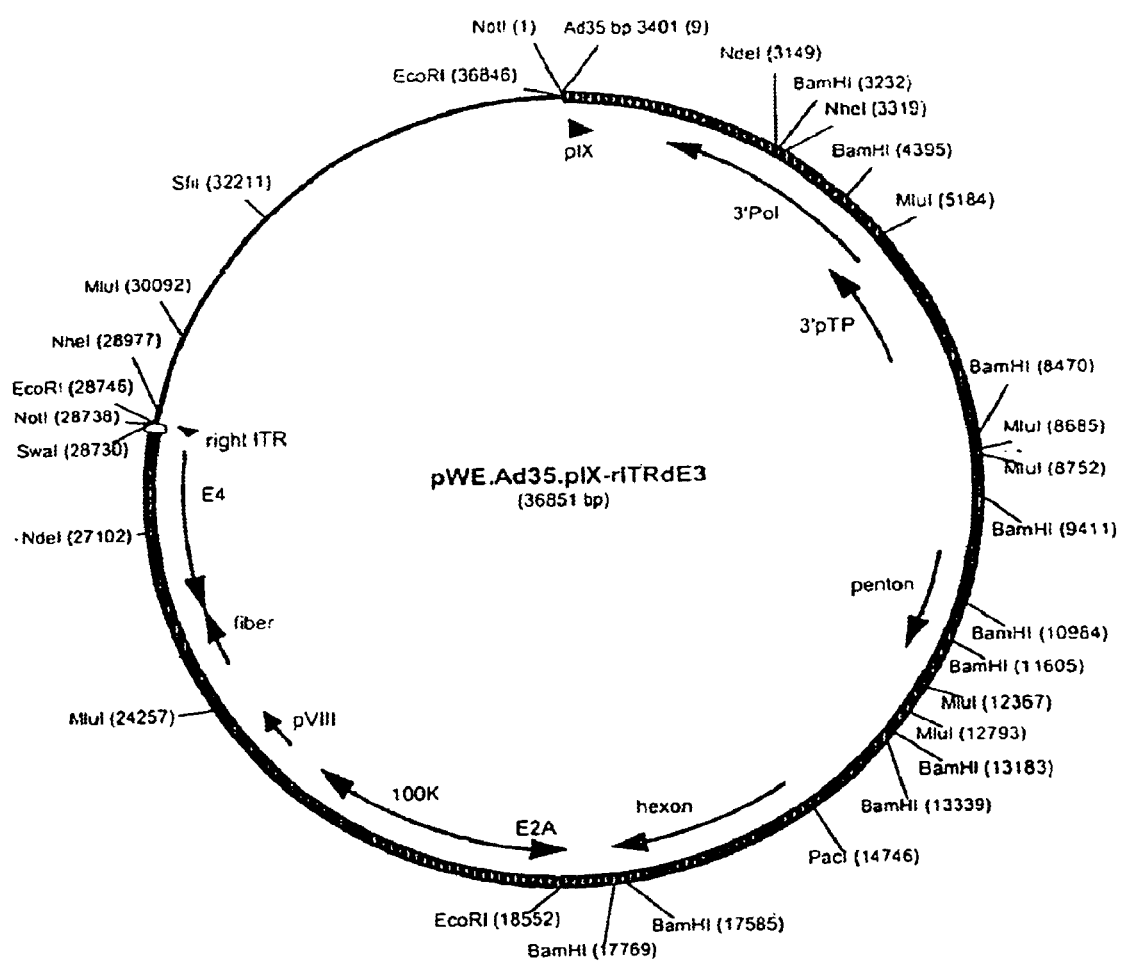

FIG. 36: Map of pWE.Ad35.pIX-rITRΔE3.

Figure 37:
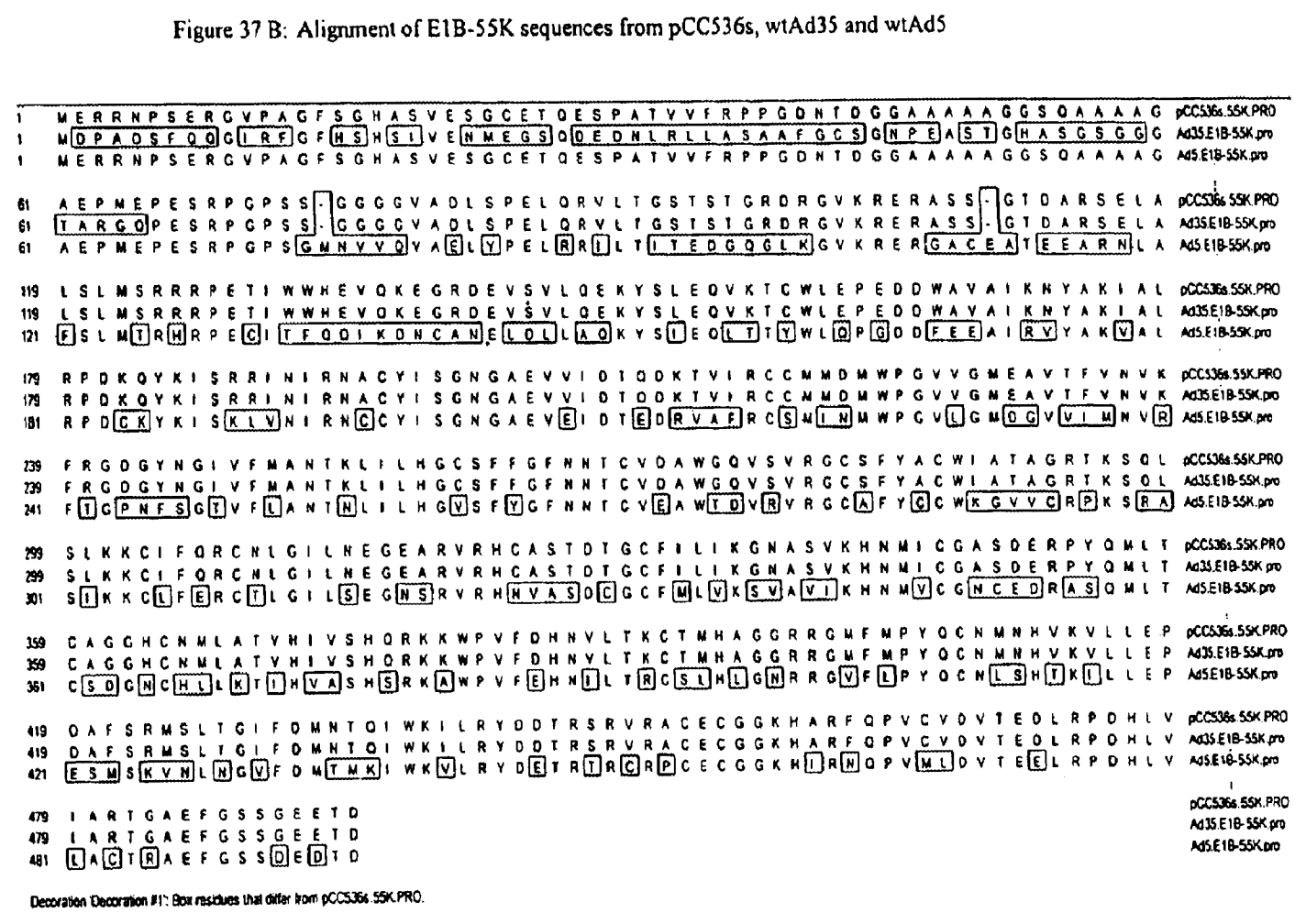
Figure 37:
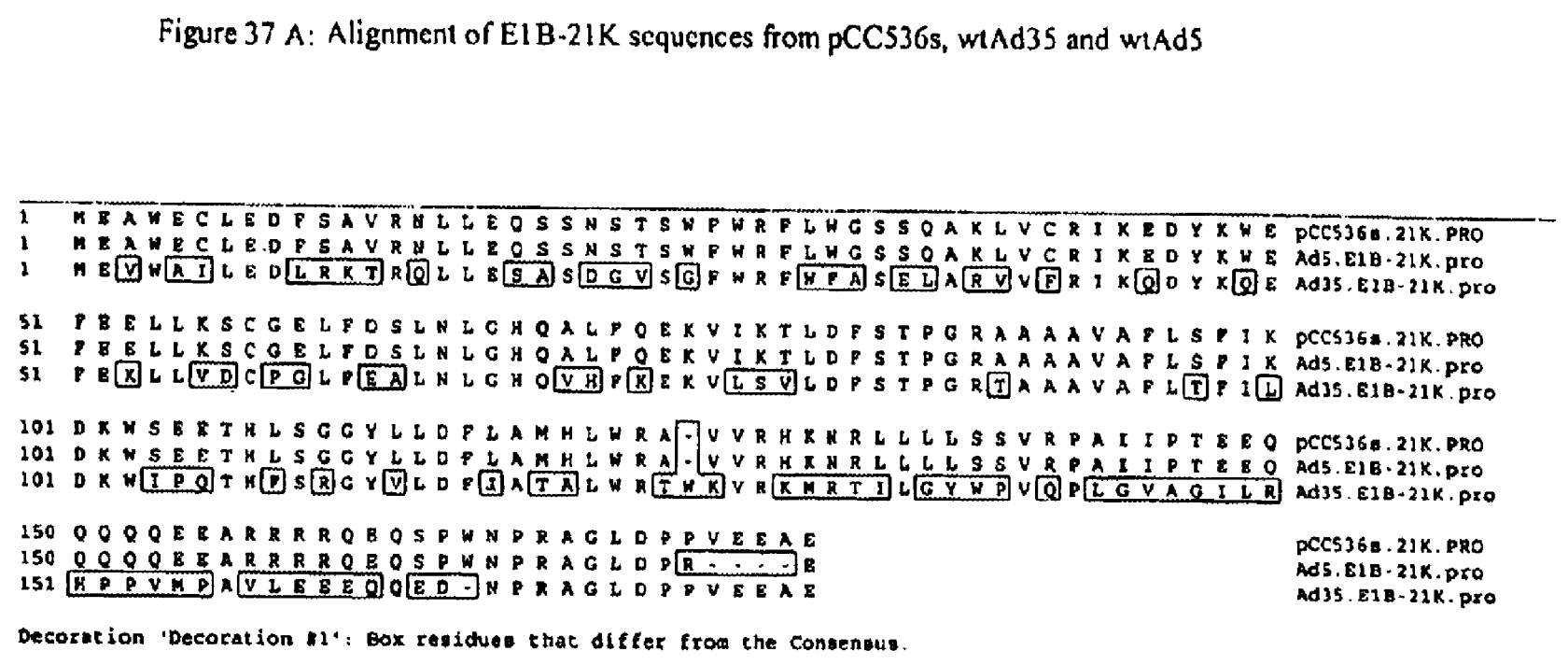

FIG. 37: Alignment of E1B-21K amino acid sequences in pCC536s (SEQ ID NO:45), wtAd5 (SEQ ID NO:46) and wtAd35 (SEQ ID NO:47) (A) and E1B-55K amino acid sequences in pCC536s (SEQ ID NO:48), wtAd5 (SEQ ID NO:49) and NO:50) (B).

DETAILED DESCRIPTION OF THE INVENTION

The invention is further explained by the use of the following illustrative examples.

EXAMPLES

Example 1
A High Throughput Assay for the Detection of Neutralizing Activity in Human Serum To enable screening of a large amount of human sera for the presence of neutralizing antibodies against all adenovirus serotypes, an automated 96-wells assay was developed.

Human Sera

A panel of 100 individuals was selected. Volunteers (50% male, 50% female) were healthy individuals between ages 20 and 60 year old with no restriction for race. All volunteers signed an informed consent form. People professionally involved in adenovirus research were excluded.

Approximately 60 ml blood was drawn in dry tubes. Within two hours after sampling, the blood was centrifuged at 2500 rpm for 10 minutes. Approximately 30 ml serum was transferred to polypropylene tubes and stored frozen at −20° C. until further use.

Serum was thawed and heet-inactivate at 56° C. for 10 minutes and then aliquoted to prevent repeated cycles of freeze/thawing. Part was used to make five steps of twofold dilutions in medium (DMEM Gibco BRL) in a quantity large enough to fill out approximately 70 96-well plates. Aliquots of undiluted and diluted sera were pipetted in deep well plates (96-well format) and using a programmed platemate dispensed in 100 µl aliquots into 96-well plates. The plates were loaded with eight different sera in duplo (1100 µl/well) according to the scheme below:

| S1/2 | S1/4 | S1/8 | S1/16 | S1/32 | S5/2 | S5/4 | S5/8 | S5/16 | S5/32 | — | — |
|---|---|---|---|---|---|---|---|---|---|---|---|
| S1/2 | S1/4 | S1/8 | S1/16 | S1/32 | S5/2 | S5/4 | S5/8 | S5/16 | S5/32 | — | — |
| S2/2 | S2/4 | S2/8 | S2/16 | S2/32 | S6/2 | S6/4 | S6/8 | S6/16 | S6/32 | — | — |
| S2/2 | S2/4 | S2/8 | S2/16 | S2/32 | S6/2 | S6/4 | S6/8 | S6/16 | S6/32 | — | — |
| S3/2 | S3/4 | S3/8 | S3/16 | S3/32 | S7/2 | S7/4 | S7/8 | S7/16 | S7/32 | — | — |
| S3/2 | S3/4 | S3/8 | S3/16 | S3/32 | S7/2 | S7/4 | S7/8 | S7/16 | S7/32 | — | — |
| S4/2 | S4/4 | S3/8 | S3/16 | S3/32 | S8/2 | S8/4 | S8/8 | S8/16 | S8/32 | — | — |
| S4/2 | S4/4 | S3/8 | S3/16 | S3/32 | S8/2 | S8/4 | S8/8 | S8/16 | S8/32 | — | — |

Where S1/2 to S8/2 in columns 1 and 6 represent 1× diluted sera and Sx/4, Sx/8, Sx/16 and Sx/32 the twofold serial dilutions. The last plates also contained four wells filled with 100 µl fetal calf serum as a negative control. Plates were kept at −20° C. until further use.

Preparation of Human Adenovirus Stocks

Prototypes of all known human adenoviruses were inoculated on T25 flask seeded with PER.C6 cells (Fallaux et al., 1998) and harvested upon full CPE. After freeze/thawing, 1–2 ml of the crude lysates were used to inoculate a T80 flask with PER.C6 and virus was harvested at full CPE. The timeframe between inoculation and occurrence of CPE, as well as the amount of virus needed to re-infect a new culture, differed between serotypes. Adenovirus stocks were prepared by freeze/thawing and used to inoculate 3–4 T175 cm² three-layer flasks with PER.C6 cells. Upon occurrence of CPE, cells were harvested by tapping the flask, pelleted and virus was isolated and purified by a two-step CsCl gradient as follows. Cell pellets were dissolved in 50 ml 10 mM NaPO$_4$ buffer (pH 7.2) and frozen at −20° C. After thawing at 37° C., 5.6 ml sodium deoxycholate (5% w/v) was added. The solution was mixed gently and incubated for 5–15 minutes at 37° C. to completely lyse the cells. After homogenizing the solution, 1875 µl 1 M MgCl$_2$ was added. After the addition of 375 µl DNAse (10 mg/ml), the solution was incubated for 30 es at 37° C. Cell debris was removed by centrifugation at 1880×g for 30 minutes at RT without brake. The supernatant was subsequently purified from proteins by extraction with FREON (3×). The cleared supernatant was loaded on a 1M Tris/HCl buffered cesium chloride block gradient (range: 1.2/1.4 g/ml) and centrifuged at 21000 rpm for 2.5 hours at 10° C. The virus band is isolated after which a second purification using a 1 M Tris/HCl buffered continues gradient of 1.33 g/ml of cesium chloride was performed. The virus was then centrifuged for 17 hours at 55000 rpm at 10° C. The virus band is isolated and sucrose (50% w/v) is added to a final concentration of 1%. Excess cesium chloride is removed by dialysis (three times 1 hr at RT) in dialysis slides (Slide-a-lizer, cut off 10000 kDa, Pierce, USA) against 1.5 liter PBS supplemented with $CaCl_2$ (0.9 mM), $MgCl_2$ (0.5 mM) and an increasing concentration of sucrose (1, 2, 5%). After dialysis, the virus is removed from the slide-a-lizer after which it is aliquoted in portions of 25 and 100 µl upon which the virus is stored at −85° C.

To determine the number of virus particles per milliliter, 50 µl of the virus batch is run on a high-pressure liquid chromatograph (HPLC) as described by Shabram et al (1997). Viruses were eluted using a NaCl gradient raging from 0 to 600 mM. As depicted in table I, the NaCl concentration by which the viruses were eluted differed significantly among serotypes.

Most human adenoviruses replicated well on PER.C6 cells with a few exceptions. Adenovirus type 8 and 40 were grown on 911-E4 cells (He et al., 1998). Purified stocks contained between $5 \times 10^{10}$ and $5 \times 10^{12}$ virus particles/ml (VP/ml; see table I).

Titration of Purified Human Adenovirus Stocks

Adenoviruses were titrated on PER.C6 cells to determine the amount of virus necessary to obtain full CPE in five days, the length of the neutralization assay. Hereto, 100 µl medium was dispensed into each well of 96-well plates. 25 µl of adenovirus stocks pre-diluted $10^4$, $10^5$, $10^6$ or $10^7$ times were added to column 2 of a 96-well plate and mixed by pipetting up and down 10 times. Then 25 µl was brought from column 2 to column 3 and again mixed. This was repeated until column 11, after which 25 µl from column 11 was discarded. This way, serial dilutions in steps of 5 were obtained starting off from a pre-diluted stock. Then $3 \times 10^4$ PER.C6 cells (ECACC deposit number 96022940) were added in a 100 µl volume and the plates were incubated at 37° C., 5% $CO_2$ for five or six days. CPE was monitored microscopically. The method of Reed and Muensch was used to calculate the cell culture-inhibiting dose 50% (CCID50).

In parallel, identical plates were set up that were analyzed using the MTT assay (Promega). In this assay, living cells are quantified by colorimetric staining. Hereto, 20 µl MTT (7.5 mgr/ml in PBS) was added to the wells and incubated at 37° C., 5% $CO_2$ for two hours. The supernatant was removed and 100 µl of a 20:1 isopropanol/triton-X100 solution was added to the wells. The plates were put on a 96-well shaker for 3–5 minutes to solubilize the precipitated staining. Absorbance was measured at 540 nm and at 690 nm (background). By this assay, wells with proceeding CPE or full CPE can be distinguished.

Neutralization Assay 96-well plates with diluted human serum samples were thawed at 37° C., 5% $CO_2$. Adenovirus stocks diluted to 200 CCID50 per 50 µl were prepred and 50 µl aliquots were added to columns 1–11 of the plates with serum. Plates were incubated for 1 hour at 37° C., 5% $CO_2$. Then, 50 µl PER.C6 cells at $6 \times 10^5$/ml were dispensed in all wells and incubated for 1 day at 37° C., 5% $CO_2$. Supernatant was removed using fresh pipette tips for each row and 200 µl fresh medium was added to all wells to avoid toxic effects of the serum. Plates were incubated for another 4 days at 37° C., 5% $CO_2$. In addition, parallel control plates were set up in duplo, with diluted positive control sera generated in rabbits and specific for each serotype to be tested in rows A and B and with negative control serum (FCS) in rows C and D. Also, in each of the rows E-H, a titration was performed as described above with steps of five times dilutions starting with 200 CCID50 of each virus to be tested. On day 5, one of the control plates was analyzed microscopically and with the MTT assay. The experimental titer was calculated from the control titration plate observed microscopically. If CPE was found to be complete, i.e., the first dilution in the control titration experiment analyzed by MTT shows clear cell death, all assay plates were processed. If not, the assay was allowed to proceed for one or more days until fill CPE was apparent, after which all plates were processed. In most cases, the assay was terminated at day 5. For Ad1, 5, 33, 39, 42 and 43 the assay was left for six days and for Ad2 for eight days.

A serum sample is regarded as "non-neutralizing" when, at the highest serum concentration, a maximum protection of 40% is seen compared to controls without serum.

The results of the analysis of 44 prototype adenoviruses against serum from 100 healthy volunteers are shown in FIG. 1. As expected, the percentage of serum samples that contained neutralizing antibodies to Ad2 and Ad5 was very high. This was also true for most of the lower numbered adenoviruses. Surprisingly, none of the serum samples contained neutralizing antibodies to Ad35. Also, the number of individuals with neutralizing antibody titers to the serotypes 26, 34 and 48 was very low. Therefore, recombinant E1-deleted adenoviruses based on Ad35 or one of the other above-mentioned serotypes have an important advantage compared to recombinant vectors based on Ad5 with respect to clearance of the viruses by neutralizing antibodies.

Also, Ad5-based vectors that have parts of the capsid proteins involved in immunogenic response of the host replaced by the corresponding parts of the capsid proteins of Ad35 or one of the other serotypes will be less, or even not, neutralized by the vast majority of human sera.

As can be seen in Table I, the VP/CCID50 ratio calculated from the virus particles per ml and the CCID50 obtained for each virus in the experiments was highly variable and ranged from 0.4 to 5 log. This is probably caused by different infection efficiencies of PER.C6 cells and by differences in replication efficiency of the viruses. Furthermore, differences in batch qualities may play a role. A high VP/CCID50 ratio means that more viruses were put in the wells to obtain CPE in 5 days. As a consequence, the outcome of the neutralization study might be biased since more inactive virus particles could shield the antibodies. To check whether this phenomenon had taken place, the VP/CCID50 ratio was plotted against the percentage of serum samples found positive in the assay (FIG. 2). The graph clearly shows that there is no negative correlation between the amount of viruses in the assay and neutralization in serum.

Example 2

The Prevalence of Neutralizing Activity (NA) to Ad35 is Low in Human Sera from Different Geographic Locations In Example 1, the analysis of neutralizing activity ("NA") in human sera from one location in Belgium was described. Strikingly, of a panel of 44 adenovirus serotypes tested, one serotype, Ad35, was not neutralized in any of the 100 sera assayed. In addition, a few serotypes, Ad26, Ad34 and Ad48 were found to be neural in 8%, or less, of the sera tested. This analysis was further extended to other serotypes of adenovirus not previously tested and, using a selection of serotypes from the first screen, was also extended to sera from different geographic locations.

Hereto, adenoviruses were propagated, purified and tested for neutralization in the CPE-inhibition assay as described in Example 1. Using the sera from the same batch as in Example 1, adenovirus serotypes 7B, 11, 14, 18 and 44/1876 were tested for neutralization. These viruses were found to be neutralized in, res vely, 59, 13, 30, 98 and 54% of the sera. Thus, of this series, Ad11 is neutralized with a relatively low frequency.

Since it is known that the frequency of isolation of adenovirus serotypes firm human tissue, as well as the prevalence of NA to adenovirus serotypes, may differ on different geographic locations, we further tested a selection of the adenovirus serotypes against sera from different places. Human sera were obtained from two additional places in Europe (Bristol, UK and Leiden, NL) and from two places in the United States (Stanford, CA and Great Neck, N.Y.). Adenoviruses that were found to be neutralized in 20%/a or less of the sera in the first screen, as well as Ad2, Ad5, Ad27, Ad30, Ad38, Ad43, were tested for neutralization in sera from the UK. The results of these experiments are presented in FIG. 3. Adenovirus serotypes 2 and 5 were again neutralized in a high percentage of human sera. Furthermore, some of the serotypes that were neutralized in a low percentage of sera in the first screen are neutralized in a higher percentage of sera from the UK, for example, Ad26 (7% vs. 30%), Ad28 (13% vs. 50%), Ad34 (5% vs. 27%) and Ad48 (8% vs. 32%). Neutralizing activity against Ad11 and Ad49 that were found in a relatively low percentage of sera in the first screen, are found in an even lower percentage of sera in this second screen (13% vs. 5% and 20% vs. 11%, respectively). Serotype Ad35 that was not neutralized in any of the sera in the first screen, was now found to be neutralized in a low percentage (8%) of sera from the UK. The prevalence of NA in human sera from the UK is the lowest to serotypes Ad11 and Ad35.

For further analysis, sera was obtained from two locations in the US (Stanford, Calif. and Great Neck, N.Y.) and from The Netherlands (Leiden). FIG. 4 presents an overview of data obtained with these sera and the previous data. Not all viruses were tested in all sera, except for Ad5, Ad11 and Ad35. The overall conclusion from this comprehensive screen of human sera is that the prevalence of neutralizing activity to Ad35 is the lowest of all serotypes throughout the western countries: on average 7% of the human sera contain neutralizing activity (5 different locations). Another B-group adenovirus, Ad11 is also neutral in a low percentage of human sera (average 11% in sera from 5 different locations). Adenovirus type 5 is neutralized in 56% of the human sera obtained from 5 different locations. Although not tested in all sera, D-group serotype 49 is also neutralized with relatively low frequency in samples from Europe and from one location of the US (average 14%).

In the herein described neutralization experiments, a serum is judged non-neutralizing when, in the well with the highest serum concentration, the maximum protection of CPE is 40% compared to the controls without serum. The protection is calculated as follows:

$$1\% \text{ protection} = \frac{OD \text{ corresponding well} - OD \text{ virus control}}{OD \text{ non-infected control} - OD \text{ virus control}} \times 100\%$$

As described in Example 1, the serum is plated in five different dilutions ranging from 4× to 64× diluted. Therefore, it is possible to distinguish between low titers (i.e., neutralization only in the highest serum concentrations) and high titers of NA (i.e., also neutralization in wells with the lowest serum concentration). Of the human sera used in our screen that were found to contain neutralizing activity to Ad5, 70% turned out to have high titers, whereas of the sera that contained NA to Ad35, only 15% had high titers. Of the sera that were positive for NA to Ad11, only 8% had high titers. For Ad49, this was 5%. Therefore, not only is the frequency of NA to Ad35, Ad11 and Ad49 much lower as compared to Ad5, but also the sera that do contain NA to these viruses, the vast majority have low titers. Adenoviral vectors based on Ad11, Ad35 or Ad49 have, therefore, a clear advantage over Ad5-based vectors when used as gene therapy vehicles or vaccination vectors in vivo or in any application where infection efficiency is hampered by neutralizing activity.

In the following examples, the construction of a vector system for the generation of safe, RCA-free Ad35-based vectors is described.

Example 3
Sequence of the Human Adenovirus Type 35

Ad35 viruses were propagated on PER.C6 cells and DNA was isolated as follows: To 100 µl of virus stock (Ad35: $3.26 \times 10^{12}$ VP/ml), 10 µl 10×DNAse buffer (130 mM Tris-HCl pH7.5; 1,2 M $CaCl_2$; 50 mM $MgCl_2$) was added. After addition of 10 µl 10 mgr/ml DNAse I (Roche Diagnostics), the mixture was incubated for 1 hr. at 37° C. Following addition of 2.5 µl 0.5M EDTA, 3.2 µl 20% SDS and 1.5 µl ProteinaseK (Roche Diagnostics; 20 mgr/ml), samples were incubated at 5° C. for 1 hr. Next, the viral DNA was isolated wing the GENECLEAN spin kit (Bio101 Inc.) according to the manufacturer's instructions. DNA was eluted from the spin column with 25 µl sterile MilliQ water. The total sequence was generated by Qiagen Sequence Services (Qiagen GmbH, Germany). Total viral DNA was sheared by sonification and the ends of the DNA were made blunt by T4 DNA polymerase. Sheared blunt fragments were size fractionated on agarose gels and gel slices corresponding to DNA fragments of 1.8 to 2.2 kb were obtained. DNA was purified from the gel slices by the QIAquick gel extraction protocol and subcloned into a shotgun library of pUC19 plasmid cloning vectors. An array of clones in 96-well plates covering the target DNA 8 (+/−2) times was used to generate the total sequence. Sequencing was performed on Perkin-Elmer 9700 thermocyclers using Big Dye Terminator chemistry and AmpliTaq FS DNA polymerase followed by purification of sequencing reactions using QIAGEN DyeEx 96 technology. Sequencing reaction products were then subjected to automated separation and detection of fragments on ABI 377 XL 96 lane sequencers. Initial sequence results were used to generate a contiguous sequence and gaps were filled in by primer walking reads on the target DNA or by direct sequencing of PCR products. The ends of the virus turned out to be absent in the shotgun library, most probably due to cloning difficulties resulting from the amino acids of pTP that remain bound to the ITR sequences after proteinase K digestion of the viral DNA. Additional sequence runs on viral DNA solved most of the sequence in those regions, however, it was difficult to obtain a clear sequence of the most terminal nucleotides. At the 5' end the sequence portion obtained was 5'-CCAATAATATACCT-3' (SEQ ID NO:1) while at the 3' end, the obtained sequence portion was 5'-AGGTATATTATTGATGATGGG-3' (SEQ ID NO:2). Most human adenoviruses have a terminal sequence 5'-CATCATCAATAATATACC-3' (SEQ ID NO:3). In addition, a clone representing the 3' end of the Ad35 DNA obtained after cloning the terminal 7 kb Ad35 EcoRI fragment into pBr322 also turned out to have the typical CAT-CATCAATAAT... sequence. Therefore, Ad35 may have the typical end sequence and the differences obtained in sequencing directly on the viral DNA are due to artifacts correlated with run-off sequence runs and the presence of residual amino acids of pTP.

The total sequence of Ad35 with corrected terminal sequences is given in SEQ ID NO:44. Based sequence homology with Ad5 (Genbank # M72360) and Ad7 (partial sequence Genbank # X03000) and on the location of open reading frames, the organization of the virus is identical to the general organization of most human adenoviruses, especially the subgroup B viruses. The total length of the genome is 34,794 basepairs.

Example 4
Construction of a Plasmid-based Vector System to Generate Recombinant Ad35-based Viruses.

A functional plasmid-based vector system to generate recombinant adenoviral vectors comprises the following components:
1. An adapter plasmid comprising a left ITR and packaging sequences derived from Ad35 and at least one restriction site for insertion of a heterologous expression cassette and lacking E1 sequences. Furthermore, the adapter plasmid contains Ad35 sequences 3' from the E1B coding region including the pIX promoter and coding sequences enough to mediate homologous recombination of the adapter plasmid with a second nucleic acid molecule.
2. A second nucleic acid molecule, comprising sequences homologous to the adapter plasmid, and Ad35 sequences necessary for the replication and packaging of the recombinant virus, that is, early, intermediate and late genes that are not present in the packaging cell.
3. A packaging cell providing at least functional E1 proteins capable of complementing the E1 function of Ad35.

Other methods for generating recombinant adenoviruses on complementing packaging cells are known in the Cart and may be applied to Ad35 viruses without departing from the invention. As an example, the cons on of a plasmid-based system, as outlined above, is described in detail below.
1) Construction of Ad35 Adapter Plasmids.

The adapter plasmid pAdApt (described in International Patent Application WO99/55132) was first modified to obtain adapter plasmids that contain extended polylinkers and that have convenient unique restriction sites flanking the left ITR and the adenovirus sequence at the 3' end to enable liberation of the adenovirus insert from plasmid vector sequences. Construction of these plasmids is described below in detail.

Adapter plasmid pAdApt was digested with SalI and treated with Shrimp Alkaline Phosphate to reduce religation. A links, composed of the following two phosphorylated and annealed oligos: ExSalPacF 5'-TCG ATG GCA AAC AGC TAT TAT GGG TAT TAT GGG TTC GAA TTA ATT AA-3' (SEQ ID NO:4) and ExSalPacR 5'-TCG ATT AAT TAA TTC GAA CCC ATA ATA CCC ATA ATA GCT GTT TGC CA-3' (SEQ ID NO:5) was directly ligated into the digested construct, thereby replacing the SalI restriction site by Pi-PspI, SwaI and PacI. This construct was designated pADAPT+ExSalPac linker. Furthermore, part of the left ITR of pAdApt was amplified by PCR using the following primers: PCLIPMSF: 5'-CCC CAA TTG GTC GAC CAT CAT CAA TAA TAT ACC TTA TTT TGG-3' (SEQ ID NO:6) and pCLIPBSRGI: 5'-GCG AAA ATT GTC ACT TCC TGT G-3' (SEQ ID NO:7)). The amplified fragment was digested with MunI and BsrGI and cloned into pAd5/Clip (described in International Patent Application WO99/55132), which was partially digested with EcoRI and after purification digested with BsrGI, thereby re-inserting the left ITR and packaging signal. After restriction enzyme analysis, the construct was digested with ScaI and SgrAI and an 800 bp fragment was isolated from gel and ligated into ScaI/SgrAI digested pADAPT+ExSalPac linker. The resulting construct, designated pIPspSalAdapt, was digested with SalI, dephosphorylated, and ligated to the phosphorylated ExSalPacF/ExSalPacR double-stranded linker previously mentioned. A clone in which the PacI site was closest to the ITR was identified by restriction analysis and sequences were confirmed by sequence analysis. This novel pAdApt construct, termed pIPspAdapt, thus harbours two ExSalPac linkers containing recognition sequences for PacI, PI-PspI and BstBI, which surround the adenoviral part of the adenoviral adapter cons, and which can be used to linearize the plasmid DNA prior to cotransfection with adenoviral helper fragments.

In order to further increase transgene cloning permutations, a number of polylinker variants were constructed based on pIPspAdapt For this purpose, pIPspAdapt was first digested with EcoRI and dephosphorylated A linker composed of the following two phosphorylated and annealed oligos: Ecolinker+: 5'-AAT TCG GCG CGC CGT CGA CGA TAT CGA TAG CGG CCG C-3' (SEQ ID NO:8) and Ecolinker: 5'-AAT TOC GGC CGC TAT CGA TAT CGT CGA CGG CGC GCC G-3' (SEQ ID NO:9) was ligated into this construct, thereby creating restriction sites for AscI, SalI, EcoRV, ClaI and NotI. Both orientations of this linker were obtained, and sequences were confirmed by restriction analysis and sequence analysis. The plasmid containing the polylinker in the order 5' HindIII, KpnI, AgeI, EcoRI, AscI, SalI, EcoRV, ClaI, NotI, NheI, HpaI, BamHI and XbaI was termed pIPspAdapt1, while the plasmid containing the polylinker in the order HindIII, KpnI, AgeI, NotI, ClaI, EcoRV, SalI, AscI, EcoRI, NheI, HpaI, BamHI and XbaI was termed pIPspAdapt2.

To facilitate the cloning of other sense or antisense constructs, a linker composed of the following two oligonucleotides was designed to reverse the polylinker of pIPspAdapt: HindXba+5'-AGC TCT AGA GGA TCC GTT AAC GCT AGC GAA TTC ACC GGT ACC AAG CTT A-3' (SEQ ID NO:10); HindXba-5'-CTA GTA AGC TTG GTA CCG GTG AAT TCG CTA GCG TTA ACG GAT CCT CTA G-3' (SEQ ID NO:11). This linker was ligated into HindIII/XbaI digested pIPspAdapt and the correct construct was isolated. Confirmation was done by restriction enzyme analysis and sequencing. This new construct, pIPspAdaptA, was digested with EcoRI and the previously mentioned Ecolinker was ligated into this construct. Both orientations of this linker were obtained, resulting in pIPspAdapt3, which cons the polylinker in the order XbaI, BamHI, HpaI, NheI, EcoRI, AscI, SalI, EcoRV, ClaI, NotI, AgeI, KpnI and HindIII. All sequences were confirmed by restriction enzyme analysis and sequencing.

Adapter plasmids based on Ad35 were then constructed as follows:

The left ITR and packaging sequence corresponding to Ad35 wt sequences nucleotides 1 to 464 (SEQ ID NO:44) were amplified by PCR on wt Ad35 DNA using the following primers:
Primer 35F1:
5'-CGG AAT TCT TAA TTA ATC GAC ATC ATC AAT AAT ATA CCT TAT AG-3' (SEQ ID NO:12)
Primer 35R2:
5'-GGT GGT CCT AGG CTG ACA CCT ACG TAA AAA CAG-3' (SEQ ID NO:13)
Amplification introduces a PacI site at the 5' end and an AvrII site at the 3' end of the sequence.

For the amplification, Platinum Pfx DNA polymerase enzyme (LTI) was used according to manufacturer's instructions, but with primers at 0.6 $\mu$M and with DMSO added to a final concentration of 3%. Amplification program was as follows: 2 min. at 94° C., (30 sec. 94° C., 30 sec. at 56° C., 1 min. at 68° C.) for 30 cycles, followed by 10 min. at 68° C.

The PCR product was purified using a PCR purification kit (LTI) according to the manufacturer's instructions and digested with PacI and AvrII. The digested fragment was then purified from gel using the GENECLEAN kit (Bio 101, Inc.). The Ad5-based adapter plasmid pIPspAdApt-3 was digested with AvrII and then partially with PacI and the 5762 bp fragment was isolated in an LMP agarose gel slice and ligated with the above-mentioned PCR fragment digested with the same enzymes and transformed into electrocompetent DH10B cells (LTI). The resulting clone is designated pIPspAdApt3-Ad35ITR.

In parallel a second piece of Ad35 DNA was amplified using the following primers:

35F3: 5'-TGG TGG AGA TCT GGT GAG TAT TGG GAA AAC-3' (SEQ ID NO:14)

35R4: 5'-CGG AAT TCT TAA TTA AGG GAA ATO CAA ATC TGT GAG G-3' (SEQ ID NO:15)

The sequence of this fragment corresponds to nucleotides 3401 to 4669 of wt Ad35 (SEQ ID NO:44) and contains 1.3 kb of sequences starting directly 3' from the E1B-55k coding sequence. Amplification and purification were done as previously described herein for the fragment containing the left ITR and packaging sequence. The PCR fragment was then digested with PacI and subcloned into pNEB193 vector (New England Biolabs) digested with SmaI and PacI. The integrity of the sequence of the resulting clone was checked by sequence analysis. pNEB/Ad35 pF3R4 was then digested with BglII and PacI and the Ad35 insert was isolated from gel using the QIAExII kit (Qiagen). pIPspAdApt3-Ad35ITR was digested with BglII and then partially with PacI. The 3624 bp fragment (containing vector sequences, the Ad35 ITR and packaging sequences as well as the CMV promoter, multiple cloning region and polyA signal) was also isolated using the QIAExII kit (Qiagen). Both fragments were ligated and transformed into competent DH10B cells (LTI). The resulting clone, pAdApt35IP3, has the expression cassette from pIPspAdApt3 but contains the Ad35 left ITR and packaging sequences and a second fragment corresponding to nucleotides 3401 to 4669 from Ad35. A second version of the Ad35 adapter plasmid having the multiple cloning site in the opposite orientation was made as follows:

pIPspAdapt1 was digested with NdeI and BglII and the 0.7 kbp band containing part of the CMV promoter, the MCS and SV40 polyA was isolated and inserted in the corresponding sites of pAdApt35IP3 generating pAdApt35IP1 (FIG. 5).

pAdApt35.LacZ and pAdApt35.Luc adapter plasmids were then generated by inserting the transgenes from pcDNA.LacZ (digested with KpnI and BamHI) and pAdApt.Luc (digested with HindIII and BamHI) into the corresponding sites in pAdApt35IP1. The generation of pcDNA.LacZ and pAdApt.Luc is described in International Patent Application WO99/55132.

2) Construction of Cosmid pWE.Ad35.pIX-rITR

FIG. 6 presents the various steps undertaken to construct the cosmid clone containing Ad35 sequences from bp 3401 to 34794 (end of the right ITR) that are described in detail below.

A first PCR fragment (pIX-NdeI) was generated using the following primer set:

35F5: 5'-CGG AAT TCG COG CCG COG TGA GTA TTG GGA AAA C-3' (SEQ ID NO:16)

35R6: 5'-CGC CAG ATC GTC TAC AGA ACA G-3' (SEQ ID NO:17)

DNA polymerase Pwo (Roche) was used according to manufacturer's instructions, however, with an end concentration of 0.6 μM of both primers and using 50 ngr wt Ad35 DNA as template. Amplification was done as follows: 2 min. at 94° C., 30 cycles of 30 sec. at 94° C., 30 sec. at 65° C. and 1 min. 45 sec. at 72° C., followed by 8 min. at 68° C. To enable cloning in the TA cloning vector PCR2.1, a last incubation with 1 unit superTaq polymerase (HT Biotechnology LID) for 10 min. at 72° C. was performed.

The 3370 bp amplified fragment contains Ad35 sequences from bp 3401 to 6772 with a NotI site added to the 5' end. Fragments were purified using the PCR purification kit (LTI).

A second PCR fragment (NdeI-rITR) was generated using the following primers:

35F7: 5'-GAA TGC TGG CTT CAG TTG TAA TC-3' (SEQ ID NO:18)

35R8: 5'-CGG AAT TCG CGG CCG CAT TTA AAT CAT CAT CAA TAA TAT ACC-3' (SEQ ID NO:19)

Amplification was done with pfx DNA polymerase (LTI) according to manufacturer's instructions but with 0.6 μM of both primers and 3% DMSO using 10 ngr. of wt Ad35 DNA as template. The program was as follows: 3 min. at 94° C. and 5 cycles of 30 sec. at 94° C., 45 sec. at 40° C., 2 min.45 sec. at 68° C. followed by 25 cycles of 30 sec. at 94° C., 30 sec. at 60° C., 2 min.45 sec. at 68° C. To enable cloning in the TA-cloning vector PCR2.1, a last incubation with 1 unit superTaq polymerase for 10 min. at 72° C. was performed. The 1.6 kb amplified fragment ranging from nucleotides 33178 to the end of the right ITR of Ad35, was purified using the PCR purification kit (LTI).

Both purified PCR fragments were ligated into the PCR2.1 vector of the TA-cloning kit (Invitrogen) and transformed into STBL-2 competent cells (LTI). Clones containing the expected insert were sequenced to confirm correct amplification Next, both fragments were excised from the vector by digestion with NotI and NdeI and purified from gel using the GENECLEAN kit (BIO 101, Inc.). Cosmid vector pWE15 (Clontech) was digested with NotI, dephosphorylated and also purified from gel. These three fragments were ligated and transformed into STBL2 competent cells (LTI). One of the correct clones that contained both PCR fragments was then digested with NdeI, and the linear fragment was purified from gel using the GENECLEAN it. Ad35 wt DNA was digested with NdeI and the 26.6 kb fragment was purified from LMP gel using agarase enzyme (Roche) according to the manufacturer's instructions. These fragments were ligated together and packaged using λ1 phage packaging extracts (Stratagene) according to the manufacturer's protocol. After infection into STBL-2 cells, colonies were grown on plates and analysed for presence of the complete insert. One clone with the large fragment inserted in the correct orientation and having the correct restriction patterns after independent digestions with three enzymes (NcoI, PvuII and ScaI) was selected. This clone is designated pWE.Ad35.pIX-rITR. It contains the Ad35 sequences from bp 3401 to the end and is flanked by NotI sites (FIG. 7).

3Generation of Ad35-based Recombinant Viruses on PER.C6.

Wild type Ad35 virus can be grown on PER.C6 packaging cells to very high titers. However, whether the Ad5-E1 region that is present in PER.C6 is able to complement E1-deleted Ad35 recombinant viruses is unknown. To test this, PER.C6 cells were cotransfected with the above-described adapter plasmid pAdApt35.LacZ and the large backbone fragment pWE.Ad35.pIX-rITR. First, pAdApt35.LacZ was digested with PacI and pWE.Ad35.pIX-rITR was digested with NotI. Without further purification, 4 μgr of each construct was mixed with DMEM (LTI) and transfected into PER.C6 cells, seeded at a density of 5×10⁶ cells in a T25 flask the day before, using Lipofectamin (LTI) according to the manufacturer's instructions. As a positive control, 6 µgr of PacI digested pWE.Ad35.pIX-rITR DNA was cotransfected with a 6.7 kb NheI fragment isolated from Ad35 wt DNA containing the left end of the viral genome including the E1 region. The next day, medium (DMEM with 10% FBS and 10 mM MgCl$_2$) was refreshed and cells were further incubated. At day 2 following the transfection, cells were trypsinized and transferred to T80 flasks. The positive control flask showed CPE at five days following transfection, showing that the pWE.Ad35.pIX-rITR construct is functional, at least in the presence of Ad35-E1 proteins. The transfection with the Ad35 LacZ adapter plasmid and pWE.Ad35.pIX-rITR did not give rise to CPE. These cells were harvested in the medium at day 10 and freeze/thawed once to release virus from the cells. 4 ml of the harvested material was added to a T80 flask with PER.C6 cells (at 80% confluency) and incubated for another five days. This harvest/re-infection was repeated two times but there was no evidence for virus associated CPE.

From this experiment, it seems that the Ad5-E1 proteins are not, or not well enough, capable of complementing Ad35 recombinant viruses. However, it may be that the sequence overlap of the adapter plasmid and the pWE.Ad35.pIX-rITR backbone plasmid is not large enough to efficiently recombine and give rise to a recombinant virus genome. The positive control transfection was done with a 6.7 kb left end fragment and, therefore, the sequence overlap was about 3.5 kb. The adapter plasmid and the pWE.Ad35.pIX-rITR fragment have a sequence overlap of 1.3 kb. To check whether the sequence overlap of 1.3 kb is too small for efficient homologous recombination, a co-transfection was done with PacI digested pWE.Ad35.pIX-rITR and a PCR fragment of Ad35 wt DNA generated with the above-mentioned 35F1 and 35R4 using the same procedures as previously described herein. The PCR fragment thus contra left end sequences up to bp 4669 and, therefore, has the same overlap sequences with pWE.Ad35.pIX-rITR as the adapter plasmid pAdApt35.LacZ, but has Ad35-E1 sequences. Following PCR column purification, the DNA was digested with SalI to remove possible intact template sequences. A transfection with the digested PCR product alone served as a negative control. Four days after the transfection, CPE occurred in the cells transfected with the PCR product and the Ad35 pIX-rITR fragment, and not in the negative control. This result shows that a 1.3 kb overlapping sequence is sufficient to generate viruses in the presence of Ad35-E1 proteins. From these experiments, we conclude that the presence of at least one of the Ad35-E1 proteins is necessary to generate recombinant Ad35 based vectors from plasmid DNA on Ad5 complementing cell lines.

Example 5

1) Construction of Ad35-E1 Expression Plasmids

Since Ad5-E1 proteins in PER.C6 are incapable of complementing Ad35 recombinant viruses efficiently, Ad35-E1 proteins have to be expressed in Ad5complementing cells (e.g., PER.C6). Alternatively, a new packaging cell line expressing Ad35-E1 proteins has to be made, starting from either diploid primary human cells or established cell lines not expressing adenovirus E1 proteins. To address the first possibility, the Ad35-E1 region was cloned in expression plasmids as described below.

First, the Ad35-E1 region from bp 468 to bp 3400 was amplified from wt Ad35 DNA using the following primer set:

35F11: 5'-GGG GTA CCG AAT TCT CGC TAG GGT ATT TAT ACC-3' (SEQ ID NO:20)

35F10: 5-GCT CTA GAC CTG CAG GTT AGT CAG TTT CTT CTC CAC TG-3' (SEQ ID NO:21)

This PCR introduces a KpnI and EcoRI site at the 5' end and an SbfI and XbaI site at the 3' end.

Amplification on 5 ngr. template DNA was done with Pwo DNA polymerase (Roche) using the manufacturer's instructions, however, with both primers at a final concentration of 0.6 µM. The program was as follows: 2 min. at 94° C., 5 cycles of 30 sec. at 94° C., 30 sec. at 56° C. and 2 min. at 72° C., followed by 25 cycles of 30 sec. at 94° C., 30 sec. at 60° C. and 2 ml at 72° C., followed by 10 min. at 72° C. PCR product was purified by a PCR purification kit (LTI) and digested with KpnI and XbaI. The digested PCR fragment was then ligated to the expression vector pRSVhbvNeo (see below) also digested with KpnI and XbaI. Ligations were transformed into competent STBL-2 cells (LTI) according to manufacturer's instructions and colonies were analysed for the correct insertion of Ad35-E1 sequences into the polylinker in between the RSV promoter and HBV polyA.

The resulting clone was designated pRSV.Ad35-E1 (FIG. 8). The Ad35 sequences in pRSV.Ad35-E1 were checked by sequence analysis.

pRSVhbvNeo was generated as follows: pRc-RSV (Invitrogen) was digested with PvuII, dephosphorylated with TSAP enzymne (LTI), and the 3 kb vector fragment was isolated in low melting point agarose (LMP). Plasmid pPGKneopA (FIG. 9; described in International Patent Application WO96/35798) was digested with SspI completely to linearize the plasmid and facilitate partial digestion with PvuII. Following the partial digestion with PvuII, the resulting fragments were separated on a LMP agarose gel and the 2245 bp PvuII fragment, containing the PGK promoter, neomycin-resistance gene and HBVpolyA, was isolated. Both isolated fragments were ligated to give the expression vector pRSV-pNeo that now has the original SV40prom-neo-SV40polyA expression cassette replaced by a PGKprom-neo-HBVpolyA cassette (FIG. 10). This plasmid was further modified to replace the BGHpA with the HBVpA as follows: pRSVpNeo was linearised with ScaI and further digested with XbaI. The 1145 bp fragment, containing part of the Amp gene and the RSV promoter sequences and polylinker sequence, was isolated from gel using the GENECLEAN lit (Bio Inc. 101). Next, pRSVp-Neo was linearised with ScaI and further digested partially with EcoRI and the 3704 bp fragment containing the PGK-neo cassette and the vector sequences were isolated from gel as above. A third fragment, containing the HBV polyA sequence flanked by XbaI and EcoRI at the 5' and 3' end, respectively, was then generated by PCR amplification on pRSVpNeo using the following primer set:

HBV-F: 5'-GGC TCT AGA GAT CCT TCG CGG GAC GTC-3' (SEQ ID NO:22) and

HBV-R: 5'-GGC GAA TTC ACT GCC TTC CAC CAA GC-3' (SEQ ID NO:23).

Amplification was done with Elongase enzyme (LTI) according to the manufacturer's instructions with the following conditions: 30 seconds at 94° C., then 5 cycles of 45 seconds at 94° C., 1 minute at 42° C. and 1 minute at 68 ec, followed by 30 cycles of 45 seconds at 94° C., 1 minute at 65° C. and 1 minute at 68° C., followed by 10 minutes at 68° C. The 625 bp PCR fragment was then purified using the Qiaquick PCR purification kit digested with EcoRI and XbaI and purified from gel using the GENECLEAN kit. The three isolated fragments were ligated and transformed into DH5α competent cells (LTI) to give the construct pRSVhbvNeo (FIG. 11). In this construct, the transcription regulatory regions of the RSV expression cassette and the neomycin selection marker are modified to reduce overlap with adenoviral vectors that often contain CMV and SV40 transcription regulatory sequences.

2) Generation of Ad35 Recombinant Viruses on PER.C6 Cells Cotransfected with an Ad35-E1 Expression Construct.

PER.C6 cells were seeded at a density of $5 \times 10^6$ cells in a T25 flask and, the next day, transfected with a DNA mixture containing:

1 µg pAdApt35.LacZ digested with PacI
5 µg pRSV.Ad35E1 undigested
2 µg pWE.Ad35.pIX-rITR digested with NotI Transfection was done using Lipofectamine according to the manufacturer's instructions. Five hours after addition of the transfection mixture to the cells, medium was removed and replaced by fresh medium. After two days, cells were transferred to T80 flasks and further cultured. One week post-transfection, 1 ml of the medium was added to A549 cells and, the following day, cells were stained for LacZ expression. Blue cells were clearly visible after two hours of staining indicating that recombinant LacZ expressing viruses were produced. The cells were further cultured, but no clear appearance of CPE was noted. However, after 12 days, clumps of cells appeared in the monolayer and 18 days following transfection, cells were detached. Cells and medium were then harvested, freeze-thawed once, and 1 ml of the crude lysate was used to infect PER.C6 cells in a 6-well plate. Two days after infection, cells were stained for LacZ activity. After two hours, 15% of the cells were stained blue. To test for the presence of wt and/or replicating competent viruses, A549 cells were infected with these viruses and further cultures. No signs of CPE were found indicating the absence of replication-competent viruses. These experiments show that recombinant AdApt35.LacZ viruses were made on PER.C6 cells cotransfected with an Ad35-E1 expression construct.

Ad35 recombinant viruses escape neutralization in human serum containing neutralizing activity to Ad5 viruses.

The AdApt35.LacZ viruses were then used to investigate infection in the presence of serum that contains neutralizing activity to Ad5 viruses. Purified Ad5-based LacZ virus served as a positive control for NA. Hereto, PER.C6 cells were seeded in a 24-well plate at a density of $2 \times 10^5$ cells/well. The next day, a human serum sample with high neutralizing activity to Ad5 was diluted in culture medium in five steps of five times dilutions 0.5 ml of diluted serum was then mixed with $4 \times 10^6$ virus particles AdApt5.LacZ virus in 0.5 ml medium and after 30 minutes of incubation at 37° C., 0.5 ml of the mixture was added to PER.C6 cells in duplicate. For the AdApt35.1acZ viruses, 0.5 ml of the diluted serum samples were mixed with 0.5 ml crude lysate containing AdApt35.LacZ virus and, after incubation, 0.5 ml of this mixture was added to PER.C6 cells in duplo. Virus samples incubated in medium without serum were used as positive controls for infection. After two hours of infection at 37° C., medium was added to reach a final volume of 1 ml and cells were further incubated. Two days after infection, cells were stained for LacZ activity. The results are shown in Table II. From these results, it is clear that whereas AdApt5.LacZ vises are efficiently neutralized. AdApt35.LacZ viruses remain infectious irrespective of the presence of human serum. This proves that recombinant Ad35-based viruses escape neutralization in human sera that contain NA to Ad5-based viruses.

Example 6

Generation of Cell Lines Capable of Complementing E1-deleted Ad35 Viruses Generation of pIG135 and pIG270

Construct pIG.E1A.E1B (FIG. 12) contains E1 region sequences of Ad5 corresponding to nucleotides 459 to 3510 of the wt Ad5 sequence (Genbank accession number M72360) operatively linked to the human phosphoglycerate kinase promoter ("PGK") and the Hepatitis B Virus polyA sequences. The generation of this construct is described in International Patent Application No. WO97/00326. The E1 sequences of Ads were replaced by corresponding sequences of Ad35 as follows. pRSV.Ad35-E1 (described in Example 5) was digested with EcoRI and Sse8387I and the 3 kb fragment corresponding to the Ad35-E1 sequences was isolated from gel. Construct pIG.E1A.E1B was digested with Sse8387I completely and partially with EcoRI. The 4.2 kb fragment corresponding to vector sequences without the Ad5-E1 region but retaining the PGK promoter were separated from other fragments on LMP agarose gel and the correct band was excised from gel. Both obtained fragments were ligated resulting in pIG.Ad35-E1.

This vector was further modified to remove the LacZ sequences present in the pUC119 vector backbone. Hereto, the vector was digested with BsaAI and BstXI and the large fragment was isolated from gel. A double stranded oligo was prepared by annealing the following two oligos:

BB1: 5'-GTG CCT AGO CCA CGG GG-3' (SEQ ID NO:24) and
BB2: 5'-GTG GCC TAG GCA C-3' (SEQ ID NO:25).

Ligation of the oligo and the vector fragment resulted in construct pIG135 (FIG. 13). Correct insertion of the oligo restores the BsaAI and BstXI sites and introduces a unique AvrII site. Next, we introduced a unique site at the 3' end of the Ad35-E1 expression cassette in pIG135. Hereto, the construct was digested with SapI and the 3' protruding ends were made blunt by treatment with T4 DNA polymerase. The thus treated linear plasmid was further digested with BsrGI and the large vector-containing fragment was isolated from gel. To restore the 3' end of the HBVpolyA sequence and to introduce a unique site, a PCR fragment was generated using the following primers:

270F: 5'-CAC CTC TGC CTA ATC ATC TC-3' (SEQ ID NO:26) and
270R: 5'-GCT CTA GAA ATT CCA CTG CCT TCC ACC-3' (SEQ ID NO:27).

The PCR was performed on pIG.Ad35.E1 DNA using Pwo polymerase (Roche) according to the manufacturer's instructions. The obtained PCR product was digested with BsrGI and dephosphorylated using Tsap enzyme (LTI), the latter to prevent insert dimerization on the BsrGI site. The PCR fragment and the vector fragment were ligated to yield construct pIG270 (FIG. 14).

Ad35-E1 Sequences are Capable of Transforming Rat Primary Cells

Newborn WAG/RIJ rats were sacrificed at 1 week of gestation and kidneys were isolated. After careful removal of the capsule, kidneys were disintegrated into a single cell suspension by multiple rounds of incubation in trypsin/EDTA(LTI) at 37° C. and collection of floating cells in cold PBS containing 1% FBS. When most of the kidney was typsinized, all cells were re-suspended in DMEM supplemented with 10% FBS and filtered through a sterile cheesecloth. Baby Rat Kidney (BRK) cells obtained from one kidney were plated in 5 dishes (Greiner, 6 cm). When a confluency of 70–80% was reached, the cells were transfected with 1 or 5 µgr DNA/dish using the $CaPO_4$ precipitation kit (LTI) according to the manufacturer's instructions. The following constructs were used in separate transfections: pIG.E1A.E1B (expressing the Ad5-E1 region), pRSV.Ad35-E1, pIG.Ad35-E1 and p1G270 (expressing the Ad35-E1 region). Cells were incubated at 37° C., 5% $CO_2$ until foci of transformed cells appeared. Table III shows the number of foci that resulted from several transfection experiments using circular or linear DNA. As expected, the Ad5-E1 region efficiently transformed BRK cells. Foci also appeared in the Ad35-E1 transfected cell layer although with lower efficiency. The Ad35 transformed foci appeared at a later time point: ~2 weeks post transfection compared with 7–10 days for Ad5-E1. These experiments clearly show that the E1 genes of the B group virus Ad35 are capable of transforming primary rodent cells. This proves the functionality of the Ad35-E1 expression constructs and confirms earlier findings of the transforming capacity of the B-group viruses Ad3 and Ad7 (Dijkema, 1979). To test whether the cells in the foci were really transformed a few foci were picked and expanded. From the 7 picked foci, at least 5 turned out to grow as established cell lines.

Generation of New Packaging Cells Derived from Primary Human Amniocytes

Amniotic fluid obtained after amniocentesis was centrifuged and cells were re-suspended in AmnioMax medium (LTI) and cultured in tissue culture flasks at 370C and 10% $CO_2$. When cells were growing nicely (approximately one cell division/24 hrs.), the medium was replaced with a 1:1 mixture of AmnioMax complete medium and DMEM low glucose medium (LTI) supplemented with Glutamax I (end concentration 4mM, LTI) and glucose (end concentration 4.5 gr/L, LTI) and 10% FBS (LTI). For transfection ~$5 \times 10^5$ cells were plated in 10 cm tissue culture dishes. The day after, cells were transfected with 20 μgr of circular pIG270/ dish using the $CaPO_4$ transfection kit (LTI) according to manufacturer's instructions and cells were incubated overnight with the DNA precipitate. The following day, cells were washed 4 times with PBS to remove the precipitate and further incubated for over three weeks until foci of transformed cells appeared. Once a week the medium was replaced by fresh medium. Other transfection agents like, but not limited to, LipofectAmine (LTI) or PEI (Polyethylenimine, high molecular weight, water-free, Aldrich) were used. Of these three agents, PEI reached the best transfection efficiency on primary human amniocytes: ~1% blue cells 48 hrs.

Following Transfection of pAdApt35. LacZ.

Foci are isolated as follows. The medium is removed and replaced by PBS after which foci are isolated by gently scraping the cells using a 50–200 μl Gilson pipette with a disposable filter tip. Cells contained in ~10 μml PBS were brought in a 96 well plate containing 15 μl trypsin/EDTA (LTI) and a single cell suspension was obtained by pipetting up and down and a short incubation at room temperature. After addition of 200 μl of the above described 1:1 mixture of AmnioMax complete medium and DMEM with supplements and 10% FBS, cells were further incubated. Clones that continued to grow were expanded and analysed for their ability to complement growth of E1-deleted adenoviral vectors of different sub-groups, specifically ones derived from K group viruses, and more specifically from Ad35 or Ad11.

Generation of New Packaging Cell Lines from HER Cells

HER cells are isolated and cultured in DMEM medium supplemented with 10% FBS (LTI). The day before transfection, ~$5 \times 10^5$ cells are plated in 6 cm dishes and cultured overnight at 37° C. and 10% $CO_2$. Transfection is done using the $CaPO_4$ precipitation kit (LTI) according to the manufacturer's instructions. Each dish is transfected with 8–10 μmgr pIG270 DNA, either as a circular plasmid or as a purified fragment. To obtain the purified fragment, pIG270 was digested with AvrII and XbaI and the 4 kb fragment corresponding to the Ad35-E1 expression cassette was isolated from gel by agarase treatment (oche). The following day, the precipitate is washed away carefully by four washes with sterile PBS. Then fresh medium is added and transfected cells are further cultured until foci of transformed cells appear. When large enough (>100 cells), foci are picked and brought into 96wells as described above. Clones of transformed HER cells that continue to grow,, are expanded and tested for their ability to complement growth of E1-deleted adenoviral vectors of different sub-groups, specifically ones derived from B-group viruses, and more specifically from Ad35 or Ad11.

New Packaging Cell Lines Derived from PER.C6

As described in Example 5, it is possible to generate and grow Ad35-E1-deleted viruses on PER.C6 cells with cotransfection of an Ad35-E1 expression construct, e.g., pRSV.Ad35.E1. However, large-scale production of recombinant adenoviruses using this method is cumbersome because, for each amplification step, a transfection of the Ad35-E1 construct is needed. In addition, this method increases the risk of non-homologous recombination between the plasmid and the virus genome with high chances of generation of recombinant viruses that incorporate E1 sequences resulting in replication-competent viruses. To avoid this, the expression of Ad35-E1 proteins in PER.C6 has to be mediated by integrated copies of the expression plasmid in the genome. Since PER.C6 cells are already transformed and express Ad5-E1 proteins, addition of extra Ad35-E1 expression may be toxic for the cells. However, it is not impossible to stably transfect transformed cells with E1 proteins since Ad5-E1-expressing A549 cells have been generated.

In an attempt to generate recombinant adenoviruses derived from subgroup B virus Ad7, Abrahamsen et al. (1997) were not able to generate E1-deleted viruses on 293 cells without contamination of wt Ad7. Viruses that were picked after plaque purification on 293-ORF6 cells (Brough et al., 1996) were shown to have incorporated Ad7-E1B sequences by nonhomologous recombination. Thus, efficient propagation of Ad7 recombinant viruses proved possible only in the presence of Ad7-E1B expression and Ad5-E4-ORF6 expression. The E1B proteins are known to interact with cellular as well as vial proteins (Bridge et al., 1993; White, 1995). Possibly, the complex formed between the E1B55K protein and E4-ORF6 which is necessary to increase mRNA export of viral proteins and to inhibit export of most cellular mRNAs is critical and, in some way, serotype-specific. The above experiments suggest that the E1A proteins of Ad5 are capable of complementing an Ad7-E1A deletion and that Ad7-E1B expression in adenovirus packaging cells on itself is not enough to generate a stable complementing cell line. To test whether one or both of the Ad35-E1B proteins is/are the limiting factor in efficient Ad35 vector propagation on PER.C6 cells, we have generated an Ad35 adapter plasmid that does contain the E1B promoter and E1B sequences but lacks the promoter and the coding region for E1A. Hereto, the left end of wt Ad35 DNA was amplified using the primers 35F1 and 35R4 (both described in Example 4) with Pwo DNA polymerase (Roche) according to the manufacturer's instructions. The 4.6 kb PCR product was purified using the PCR purification kit (LTI) and digested with SnaBI and ApaI enzymes. The resulting 4.2 kb fragment was then purified from gel using the QIAExII kit (Qiagen). Next, pAdApt35IP1 (Example 4) was digested with SnaBI and ApaI and the 2.6 kb vector-containing fragment was isolated from gel using the GENECLEAN kit (BIO 101, Inc). Both isolated fragments were ligated to give pBr/Ad35.leftITR-pIX (FIG. 15). Correct amplification during PCR was verified by a functionality test as follows: The DNA was digested with BstBI to liberate the Ad35 insert from vector sequences and 4 µg of this DNA was cotransfected with 4 µg of NotI digested pWE/Ad35.pIX-rITR Example 4) into PER.C6 cells. The transfected cells were passaged to T80 flasks at day 2 and again two days later CPE had formed showing that the new pBr/Ad35.leftITR-pIX construct contains functional E1 sequences. The pBr/Ad35.leftITR-pIX construct was then further modified as follows. The DNA was digested with SnaBI and HindIII and the 5' HindII overhang was filled in using Klenow enzyme. Religation of the digested DNA and transformation into competent cells (LTI) gave construct pBr/Ad35leftITR-pIXΔDE1A (FIG. 16). This latter construct contains the left end 4.6 kb of Ad35 except for E1A sequences between bp 450 and 1341 (numbering according to SEQ ID NO:44) and thus lacks the E1A promoter and most of the E1A coding sequences. pBr/Ad35.leftITR-pIXΔDE1A was then digested with BstBI and 2 µg of this construct was cotransfected with 6 µmgr of NotI digested pWE/Ad35.pIX-rITR (Example 4) into PER.C6 cells. One week following transfection, full CPE had formed in the transfected flasks.

This experiment shows that the Ad35-E1A proteins are functionally complemented by Ad5-E1A expression in PER.C6 cells and that at least one of the Ad35-E1B proteins cannot be complemented by Ad5-E1 expression in PER.C6. It further shows that it is possible to make a complementing cell line for Ad35-E1-deleted viruses by expressing Ad35-E1B proteins in PER.C6. Stable expression of Ad35-E1B sequences from integrated copies in the genome of PER.C6 cells may be driven by the E1B promoter and terminated by a heterologous poly-adenylation signal like, but not limited to, the HBVpA. The heterologous pA signal is necessary to avoid overlap between the E1B insert and the recombinant vector, since the natural E1B termination is located in the pIX transcription unit that has to be present on the adenoviral vector. Alternatively, the E1B sequences may be driven by a heterologous promoter like, but not limited to, the human PGK promoter or by an inducible promoter like, but not limited to, the 7xtetO promoter (Gossen and Bujard, 1992). Also, in these cases, the transcription termination is mediated by a heterologous pA sequence, e.g., the HBV pA. The Ad35-E1B sequences at least comprise one of the coding regions of the E1B-21K and the E1B-55K proteins located between nucleotides 1611 and 3400 of the wt Ad35 sequence. The insert may also include part of the Ad35-E1B sequences between nucleotides 1550 and 1611 of the wt Ad35 sequence (SEQ ID NO:44).

Example 7
Ad35-based Viruses Deleted for E1A and E1B-21K Genes Efficiently Propagate on Ad5 Complementing Cell Lines.

The generation of Ad35-based viruses that are deleted for E1A and retain the full E1B region is described in Example 6 of this application. Such viruses can be generated and propagated on the Ad5 complementing cell line PER.C6. The E1B region comprises partially overlapping coding sequences for the two major proteins 21K and 55K (Bos et al, 1981). Whereas, during productive wt adenoviral infection, both 21K and 55K are involved in counteracting the apoptose-inducing effects of E1A proteins, the E1B-55K protein has been suggested to have additional functions during the late phase of virus infection. These include the accumulation of viral mRNAs, the control of late viral gene expression and the shutoff of most host mRNAs at the level of mRNA transport (Babiss et al., 1984, 1985; Pilder et al., 1986). A complex formed between E1B-55K and the ORF6 protein encoded by the adenovirus early region 4 (and Shenk, 1989; Bridge and Ketner, 1990) exerts at least part of these functions.

To analyze which of the E1B proteins is required for propagation of Ad35-E1A-deleted recombinant viruses on PER.C6 packaging cells, the E1B region in construct pBr.Ad35.leftITR-pIXΔE1A (see Example 6 and FIG. 16) was further deleted. A first construct, pBr.Ad35Δ21K, retains the fill E1B-55K sequence and is deleted for E1A and E1B-21K. Hereto, pBr.Ad35.leftITR-pIXΔE1A was digested with NcoI and BspE1 and the 5 KB vector fragment was isolated from agarose gel using the GENECLEAN kit (BIO 101, Inc.) according to the manufacturer's instructions. Then a PCR fragment was generated with pBr.Ad35.leftITR-pIXΔE1A as template DNA using the following primers:

35D21: 5'-TTA GAT CCA TGG ATC CCG CAG ACT C-3' (SEQ ID NO:28) and

35B3: 5'-CCT CAG CCC CAT TTC CAG-3' (SEQ ID NO:29).

Amplification was done using Pwo DNA polymerase (Roche) according to manufacturer's recommendations with the addition of DMSO (final concentration 3%/o) in the reaction mixture. The PCR program was as follows: 94° C. for 2', then 30 cycles of 94° C. for 30", 58° C. for 30" and 72° C. for 45" and a final step at 68° C. for 8' to ensure blunt ends.

This PCR amplifies Ad35-E1B sequences from nucl. 1908 to 2528 (sequence Ad35, SEQ ID NO:44) and introduces an NcoI site at the start codon of the E1B-55K coding sequence (bold in primer 35D21). The 620 bp PCR fragment was purified using the PCR purification kit (Qiagen) and then digested with NcoI and BspEI, purified from agarose gel as above and ligated to the above-described NcoI/BspE1 digested vector fragment to give pBr.Ad35A21K (FIG. 17).

Since the coding regions of the 21K and 55K proteins overlap, it is only possible to delete part of the 55K coding sequences while retaining 21K. Hereto, pBr.Ad35.leftITR-pIXΔE1A was digested with BglII and the vector fragment was religated to give pBr.Ad35Δ55K1 (FIG. 18). This deletion removes E1B coding sequences from nucl. 2261 to 3330 (Ad35 sequence in SEQ ID NO:44). In this construct the N-terminal 115 amino acids are retained and become fused to 21 additional amino acids out of the proper reading frame before a stop codon is encountered. The 21K coding region is intact in construct pBr.Ad35Δ55K1.

A third construct that has a deletion of E1A, 21K and most of the 55K sequences was generated as follows. pBr.Ad35.leftITR-pIX (FIG. 15) was digested with SnaBI and MfeI (isoschizomer of MunI) and the 5' overhang resulting from the MfeI digestion was filled in using Klenow enzyme. The 4.4 kb vector fragment was isolated from gel using the GENECLEAN kit (Bio 101, Inc.) according to the manufacturer's instructions and relegated to give construct pBr.Ad35ΔSM (FIG. 19). In this construct, the Ad35 sequences between nucl. 453 and 2804 are deleted. Thus, 596 nucl. of the 3' end of E1b-55K are retained. A further deletion of 55K sequences was made in construct pBr.Ad35AE 1A.ΔE1B by digestion of pBr.Ad35.leftITR-pIX with SnaBI and BglII, Klenow treatment to fill in the BglII cohesive ends, and religation FIG. 20 shows a schematic representation of the above-mentioned constructs.

To test whether Ad35-based viruses can be generated with these constructs, each of the constructs was cotransfected with NotI digested pWE.Ad35pIX-rITR (see, Example 4)

onto PER.C6 cells. Hereto, the respective fragments were PCR amplified using primers 35F1 and 35R4 (see, Example 4). This PCR amplification was done since some of the constructs were difficult to isolate in large enough quantities. In this way, equal quality of the different adapter fragments was ensued. For the amplification, Pwo DNA polymerase (Roche) was used according to the manufacturer's instructions but with DMSO (3% final concentration) added to the PCR mixture. Of each template ~50 ng DNA was used. The conditions for the PCR were as follows: 94° C. for 2', then 5 cycles of 94° C. for 30", 48° C. for 45" and 72° C. for 4' followed by 25 cycles of 94° C. for 30", 60° C. for 30" and 72° C. for 4' and a final step at 68° C. for 8'.

PCR fragments were generated from pBr.Ad35leftITR-pIX, pBr.Ad35.leftITR-pIXΔE1A, pBr.Ad35Δ21K, pBr.Ad35Δ55K1, pBr.Ad35ΔSM and pBr.Ad35ΔE1AΔE1B. Au fragments were using the PCR purification kit (Qiagen) according to manufacturer's instructions and final concentrations were estimated on EtBr stained agarose gel using the Eagle Eye II Still Video system and EagleSight software (Stratagene) with the SmartLadder molecular weight marker (Eurogentec) as reference.

PER.C6 cells were seeded at a density of $2.5 \times 10^6$ cells in a T25 culturing flask in DMEM containing 10% fetal calf serum (FCS) and 10 mM $MgSO_4$ and cultured in a humidified stove at 37° C., 10% $CO_2$. The next day, 3 mg of each of the PCR fragments was cotransfected with 5 μgr NotI digested pWE.Ad35pIX-rITR using LipofectAmine (GIBCO, Life Technologies Inc.) according to the manufacturer's instructions. Two days after the transfection, all cells were passed to a T80 flask and further cultured. Cultures were then monitored for the appearance of CPE. In line with the outcome of previous experiments described in Examples 4 and 6, pBr.Ad35.leftITR-pIX and pBr.Ad35.leftITR-pIXΔE1A showed almost full CPE within one week following transfection. Of the fragments with different E1B deletions, only pBr.Ad35Δ21K showed CPE at the same time as the above two fragments. Constructs pBr.Ad35Δ55K1, pBr.Ad35ΔSM and pBr.Ad35ΔE1AΔE1B did not give CPE at all, not even after harvesting by freeze-thawing and re-infection of the crude lysate onto fresh PER.C6 cells.

From these experiments, it can be concluded that Ad35-E1B-55K, and not E1B-21K, is necessary for generation and propagation of Ad35-based viruses on Ad5 complementing cell lines. Therefore, Ad35-based viruses having a deletion of the E1A and E1B-21K genes and having the E1B-55K gene or a functional fragment thereof, can be grown on Ad5 complementing cell lines. Alternatively, Ad35-based viruses can be grown on PER.C6 cells that stably express the full E1B region or the E1B-55K gene, or a functional fragment thereof. The Ad35-E1B-55K gene, or functional parts thereof may be expressed from a heterologous promoter like, but not limited to, the human PGK promoter, the human cytomegalovirus immediate early promoter (CMV), Rous sarcoma virus promoter, etc., and terminated by a heterologous poly adenylation sequence (pA) like, but not limited to, the hepatitis B virus poly adenylation sequence (HBVpA) and the Simian Virus 40 poly adenylation sequence (SV40pA), etc. As nonlimiting examples, PERC6 cells that express the Ad35-E1B region driven by the E1B promoter and HBVpA, PER.C6 cells that express the Ad35-E1B region driven by the human PGK promoter and HBVpA and PER.C6 cells that express a functional fragment of Ad35-E1B-55K driven by the human PGK promoter and HBVpA are described below.

Generation of pIG35BL and pIG35BS

We describe the generation of two expression constructs, pIG.35BS and pIG.35BL, that both carry the Ad35-E1B genes and a neomycin selection marker. The two constructs differ in the length of the fragment containing the E1B promoter. In 35BL, the promoter fragment is longer and includes the 3' end of the E1A region (103 nucl. coding sequence and pA). The E1B region is terminated by the HBVpolyA and the $neo^r$ gene is driven by a hPGK promoter/HBVpA cassette.

pIG.35BL was made as follows. Construct pRSV.Ad35E1 (described in Example 5, FIG. 8) was digested with NruI and HindIII and the protruding ends were filled in by Klenow treatment. The 7 kb vector fragment was separated from the smaller fragment on gel and isolated using the GENECLEAN kit (BIO 101, Inc.). After religation of the DNA and transformation into competent STBL2 cells (Gibco, LTI), correct clones were isolated pIG.35BL (FIG. 21) contains 273 nucl. upstream of the start site of the E1B21K coding region.

pIG.35BS was made in the same way as pIG.35BL except that pRSV.Ad35E1 was digested with NruI and HpaI (both enzymes leave blunt ends), resulting in a shorter fragment upstream of the coding region of E1B21K: 97 nucleotides.

To generate Ad35-E1B expressing cells, PER.C6 cells were seeded in 10 cm dishes at $1 \times 10^6$ cells/dish. Two days later, cells were transfected with ScaI linearised constructs. Four dishes were transfected with 1 and four with 2 μg DNA (total of 16 dishes; Lipofectamine (Gibco, LTI), no carrier DNA used) according to the manufacturer's instructions. The next day, transfected cells received G418containing medium (0.75 mg/ml). Control transfections using LacZ expression constructs (2 μg) were stained after 48 hrs and showed a transfection efficiency of ~25%. Four days following addition of selection medium, untransfected cells started to die and again, three days later, clones were becoming visible. A week later, the first clones were picked. Transfection with 1 μg resulted in less and also, initially, smaller clones (total ~20 clones/dish against >50 clones/dish for the transfection with 2 μg DNA). The positive control transfection using 2 μg pcDNA3 (Invitrogen) resulted in ~50 clones.

In total, 120 clones were picked and 107 were succesfully established (55 from pIG35BS and 52 from pIG35BL).

Generation of pIG35Bneo pIG35Bneo is an Ad35-E1B expression plasmid from which the E1B genes are expressed from a heterologous promoter (hPGK) and that also contains a neomycin resistance expression cassette. To avoid instability of the plasmid due to recombination events on homologous sequences, the RSV promoter drives the $neo^r$ gene. To achieve this, construct pRSVhbv.Neo (described in Example 5, FIG. 11) was digested with ScaI and BamHI and protruding ends were filled in using Klenow enzyme. The 1070 bp fragment containing part of the Ampicilin gene and the RSV promoter was isolated from gel using the GENECLEAN kit (BIO 101, Inc.). Next, pRSVhbvNeo was digested with ScaI and EcoRI, blunted with Klenow and the 3.2 kb fragment containing the neo gene, HBVpA, vector and part of the Ampicilin gene was isolated as above. The two fragments were then ligated to give pRSVneo4 (FIG. 22). Construct pIG270 (FIG. 14, described in Example 6) was then digested with EcoRI and NcoI and sticky ends were blunted with Klenow enzyme. The vector-containing fragment was isolated from gel as described above and religated to give pIG270delE1A. This construct was digested with AvrII and XbaI and protruding ends were filled in using Klenow enzyme. The 2.9 kb fragment containing the hPGK promoter and Ad35-E1B sequences was isolated from gel as above. Next, pRSVneo4 was digested with BglII, blunted with Klenow enzyme, dephosphorylated and isolated from gel. The blunted AvrII/XbaI Ad35-E1B fragment was then ligated with the above prepared pRSVneo4 vector fragment and resulting clones were analysed. One clone that contained both expression cassettes in the same orientation was chosen and named pIG35Bneo (FIG. 23). Detailed analysis of this clone revealed that an extra BglII site was present, probably due to an incomplete Klenow reaction (BglII site at nucl 2949 in FIG. 23).

Generation of pIG35.55K

Construct pIG35.55K is similar to pIG35Bneo, however, it lacks the coding region of Ad35-E1B-21K. Hereto, both the E1A and E1B-21K sequences are first deleted from pIG270 as follows:

Construct pIG270 is digested with EcoRI, treated with Klenow enzyme and purified using a PCR purification kit (Qiagen) according to the manufacturer's instructions. The recovered DNA is then digested with AgeI and the ~5 kb vector fragment was isolated from gel as above. Next, Ad35-E1B-55K sequences sre amplified by PCR on pIG270 template DNA using the following primers:

35D21: 5'-TTA GAT CCA TGG ATC CCG CAG ACT C-3' (SEQ ID NO:28) and

35B3: 5'-CCT CAG CCC CAT TTC CAG-3' (SEQ ID NO:29)

The conditions used for the amplification are as previously described. The PCR Eminent is purified using the PCR purification kit (Qiagen) and digested with NcoI. Following Klenow treatment to fill in the protruding ends, the DNA is further digested with AgeI and again column purified. The thus treated PCR fragment is then cloned into the above prepared EcoRI/AgeI digested vector fragment to give pIG270.ΔE1AΔ21K. The last steps to obtain pIG35.55K (FIG. 24) are equivalent to the last steps described above for the generation of pIG35Bneo, starting with pIG270.ΔE1AΔ21K instead of pIG270.ΔE1A.

pIG35.55K is then linearized with ScaI and used to transfect PER.C6 cells as described above. Clones that are resistent to G418 selection are picked and analysed for their ability to complement the propagation of E1-deleted Ad35 viruses.

Example 8
New Packaging Cell Lines for the Generation and Propagation of E1-deleted Ad35-based Vectors Derived from Primary Human Cells.

The complete morphological transformation of primary cells by adenovirus E1 genes is the result of the combined activities of the proteins encoded by the E1A and E1B regions. The roles of the different E1 proteins in lytic infection and in transformation have been studied extensively (reviewed in Zantema and van der Eb, 1995; White, 1995, 1996). The adenovirus E1A proteins are essential for transformation of primary cells. The E1A proteins exert this effect through direct interaction with a number of cellular proteins that are involved in regulation of transcription. These include the pRB family of proteins, p300/CBP and TATA binding protein. In addition to this, E1A increases the level of p53 protein in the cells. In the absence of adenovirus E1B activity, the rise in p53 levels leads to the induction of apoptosis. Both proteins encoded by the E1B region counteract the induction of apoptosis, although by different mechanisms. E1B-21K seems to counteract apoptosis in a manner similar to Bcl-2 via interaction with the effector proteins downstream in the apoptosis pathway (Han et al., 1996), whereas E1B-55K functions through direct interaction with p53. Importantly, the molecular mechanism by which the E1B-55K proteins of Ad2 and 5 (subgroup C) and Ad12 (subgroup A) function in the ability to neutralise p53 may differ. Whereas Ad5 E1B-55K binds p53 strongly and the complex localises to the cytoplasm, Ad12-E1B-55K binds p53 weakly and both proteins are localised in the nucleus (Zantema et al., 1985; Grand et at, 1999). Both proteins, however, inhibit the transactivation of other genes by p53 (Yew and Berk, 1992).

In rodent cells, the activity of E1A, together with either E1B-21K or 55K, is sufficient for full transformation, although expression of both E1B proteins together is twice as efficient (Rao et al., 1992; ). In human cells, however, the activity of the E1B-55K protein seems to be more important, given the observation that E1B-55K is indispensible for the establishment of transformed cells (Gallimore, 1986).

Example 6 hereof describes the generation of pIG270. In this cons the Ad35-E1 genes are expressed from the hPGK promoter and transcription is terminated by the HBVpA. The hPGK promoter constitutes a HincII-EcoRI fragment of the promoter sequence described by Singer-Sam et al. (1984). The HBVpA is located in a BamHI-BglII fragment of the Hepatitis B virus genome (Simonsen and Levinson, 1983; see also Genbank HBV-AF090841). As mentioned before, the promoter and polyadenylation sequences of the E1 expression constructs described in this invention may be derived from other sources whithout departing from the invention. Also, other functional fragments of the hPGK and HBVpA sequences mentioned above may be used.

The functionality of pIG270 was shown by transformation of primary Baby Rat Kidney cells (BRK). Comparison with an equivalent Ad5-E1 expression construct taught that Ad35-E1 genes were less efficient in transforming these cells. The same has been found for the E1 genes of Ad12 (Bernards et at., 1982).

It is unclear which E1 protein(s) determine(s) the difference in transformation efficiency of E1 sequences observed for adenoviruses from different subgroups. In the case of Ad12, transfection studies with chimeric E1A/E1B genes suggested that the efficiency of transformation of BRK cells was determined by the E1A proteins (Bernards et al., 1982). The E1B-55K protein is shown infra to contain serotype-specific functions necessary for complementation of E1-deleted adenoviruses. If these functions are related to the regulation of mRNA distribution or another late viral function, it is unlikely that these are involved in the transformation efficiency.

Analysis of functional domains in the Ad2 or Ad5-E1B-55K proteins using insertion mutants have revealed that functions related to viral replication, late protein synthesis and host protein shut-off are not confined to specific domains but are distributed along the protein (Yew et al., 1990). Using the same set of mutants, the domains important for interaction with p53 and E4-Orf6 were found to be more restricted. In addition to one common binding region (amino acids 262 to 326), p53 binding was affected by mutations at aa 180 and E4-Orf6 binding was affected by mutations at aa 143 (Yew and Berk, 1992; Rubenwolf et al., 1997).

Altogether, these results indicate that it is difficult to separate the E1B-55K functions related to transformation (p53 binding) and late protein synthesis (Orf6 binding).

The invention discloses new E1 constructs that combine the high efficiency of transformation of one serotype with the serotype-specific complementation function of another serotype. These new constructs are used to transform primary human embryonic retinoblast cells and human amniocytes.

The Generation of pIG535, pIG635 and pIG735

Construct pIG535 contains the Ad5-E1A region and E1B promoter sequences linked to the Ad35-E1B sequences. Hereto, pIG270 (FIG. 14; see example 6) was digested with EcoRI and NcoI. The 5.3 kb vector fragment was then isolated from gel using the GENECLEAN kit (BIO Inc. 101) according to the instructions of the manufacturer. Next, construct pIG.E1A.E1B (FIG. 12; see example 6) was digested with EcoRI and XbaI and the resulting 890 bp fragment was isolated as above. A third fragment was generated by PCR amplification on pIG.E1A.E1B using the following primers:

5E1A-F: 5'-GAG ACG CCC GAC ATC ACC TG-3' (SEQ ID NO:30) and

5E1B-R: 5'-CAA GCC TCC ATG GGG TCA GAT GTA AC-3' (SEQ ID NO:31).

The following PCR program was used: 94° C. for 2' followed by 30 cycles of 94° C. for 30", 60° C. for 30" and 72° C. for 1', and a final step at 72° C. for 10' to ensure blunt ends.

The resulting 400 bp PCR fragment was digested with XbaI and NcoI. After gel isolation as above, the three fragments were ligated and transformed into STBL-2 bacteria One colony containing all three fragments in the correct order was selected and designated pIG535 (FIG. 25).

Construct pIG635 contain the Ad5-E1A and a chimeric Ad5-Ad35-E1B region such that the 21K sequence is essentially from Ad5 and linked to the Ad35-E1B-55K sequences as far as not overlapping with the 21K sequences. First, part of the Ad5-E1 sequences are amplified by PCR using pIG.E1A.E1B as template and the following primers:

5AK: 5'-GAG CGA AGA AAC CCA TCT GAG-3' (SEQ ID NO:32) and

2155R: 5'-GGT CCA GGC CGG CTC TCG G-3' (SEQ ID NO:33). Amplification is accomplished with Pwo DNA polymerase (Roche) according to manufactures instructions. The 210 bp fragments is then purified from the primer sequences using the PCR purification kit (Qiagen).

A second PCR fagment is amplified from pIG270 DNA as described above but with the following primers:

2155F: 5'-CCG AGA GCC GGC CTG GAC-3' (SEQ ID NO:34) and

35F10: 5'-GCT CTA GAC CTG CAG GTT AGT CAG TTT CTT CTC CAC TG-3' (SEQ ID NO:35).

The 1.3 kb amplified fragment is purified as above and mixed in a 1:1 molar ratio with the first PCR fragment The mixture is then first subjected to a PCR reaction without the addition of primers using Pwo DNA polymerase and the following program: 94° C. for 2' and then 5 cycles of 94° C. for 30", 60° C. for 30", 72° C. for 90". Subsequently, primers 5AK and 35F10 are added at 0.6 µM concentration after which a last PCR amplifies a 1.5 kb fragment Hereto, temperature was set as follows: 94° C. for 2', then 30 cycles of 94° C. for 30", 60° C. for 30" and 72° C. for 90", followed by a final step at 72° C. for 10' to ensure blunt ends. The resulting product is purified using the PCR purification kit (Qiagen) as above and digested with KpnI and SbfI (isoschizomer of Sse83871). The digested DNA is then isolated from gel using the GENECLEAN kit (BIO Inc., 101). Construct pIG.E1A.E1B is digested with KpnI and SbfI and the vector-containing fragment is isolated from gel as above. This fragment is ligated to the above prepared final PCR product and the ligation mixture is transformed into STBL-2 cells (Gibco, LTI) according to manufacturer's instructions. This gives construct p1G635 (FIG. 26).

In construct pIG735, the border between Ad5 derived sequences and Ad35 derived sequences is located more 3' than in construct pIG635. First, a BspEI site is introduced in the Ad5 sequence of construct pIG.E1A.E1B without changing the amino acid sequence. Hereto, Ad5 sequences from pIG.E1A.E1B are amplified using the following PCR primers:

5AK: see above (SEQ ID NO:32), and Bsp-R: 5'-GCT CTA GAC CTG CAG GGT AGC AAC AAT TCC GGA TAT TTA CAA G-3' (SEQ ID NO:36). Amplification is accomplished using Pwo DNA polymerase (Roche) according to the manufacturer's instruction. The following PCR program is used: 94° C. for 2' followed by 30 cycles of 94° C. for 30", 60° C. for 30" and 72° C. for 30", and a final step at 72° C. for 10' to ensure blunt ends. The resulting 0.6 kb gent is purified as above and digested with KpnI and SbfI and ligated to the above described KpnI/SbfI digested pIG.E1E1B vector fragment. Selection of colonies after transformation of STBL-2 bacteria (Life Techn. Inc.) gives construct pIG.E1Δ55K. pIG.E1Δ55K is then digested with SbfI and partially with BspEI. The 6.4 kb SbfI-partial BspEI digested vector fragment is then isolated from gel using the geneclean kit (BIO 101, Inc.). Next, pIG270 is digested with BspEI and SbfI and the resulting 915 bp fragment is isolated from gel as above This fragment is then ligated to the above prepared SbfI/partial BspEI digested pIG.E1Δ55K vector fragment and transformed into STBL-2 competent cells. This gives construct pIG735 (FIG. 27). Clones are analysed by restriction enzyme digestion and sequencing to ensure correct ligation of the fragments. Constructs pIG535, pIG635 and pIG735 can be used to generate complementing cell lines from primary human cells as described in Example 6.

Example 9

PER.C6-based Complementing Cell Lines for E1-deleted Ad35 Viruses.

PER.C6 cells were seeded in 10 cm culture dishes at a density of 3×10⁶ cells/dish in DMEM (Gibco BRL) complemented with FBS (Gibco BRL) up to 10% and 10 mM $MgCl_2$ (4.9 M stock solution, Sigma). Two days later, 9 dishes were transfected with 1 µg ScaI linearised pIG35.55K DNA (see example 7) and 9 dishes were transected with 1.5 µg ScaI linearised pIG35.55K DNA. Separate control dishes were transfected with 1 or 1.5 µg ScaI linearised pAdApt35.LacZ to monitor transfection efficiency and with 1 or 1.5 µg ScaI linearised pcDNA.nlsLacZ. pcDNA.nlsLacZ is a pcDNA3-based plasmid (Invitrogen) with the nlsLacZ gene (Bonnerot et al., 1987) driven by the CMV promoter. pcDNA.nlsLacZ also contains a neo$^r$ expression cassette. As a negative control one extra dish was transfected with linearised pAdApt35.LacZ, a construct that lacks the neo$^r$ selection gene. All transfections were performed with the LipofectAmine transfection kit (Invitrogen/Life Technologies) according to manufacturers instructions using 5 ml LipofectAmine reagent/µg DNA. Cells were incubated for 4 hrs with the transfection mixture after which the medium was replaced with PER.C6 culture medium. The next day medium was replaced with culture medium containing 0.5 mg/ml G418 (Gibco BRL) except in the two dishes that were transfected with 1 or 1.5 µg pAdApt35.LacZ. These latter dishes were used to monitor LacZ expression two days following transfection After X-gal staining of these cultures transfection efficiency was estimated at approximately 40% with slightly more blue cells in the dish transfected with 1.5 µg DNA. Selection medium was refreshed twice weekly in the remaining transfected dishes. Within two weeks following first addition of selection medium most cells in the negative control dish (transfected with 1.5 µg pAdApt35.LacZ) were dead. In the dishes transfected with pcDNA.nlsLacZ cell clones were becoming visible. Since the cells transfected with pIG35.55K seemed to be more resistant to G418, the concentration was raised to 0.75 mg/ml 3 weeks following transfection Three days and seven days later a total of 196 cell clones were picked from the dishes transfected with pIG35.55K and seeded in separate wells of 96-well plates.

Cells remaining after colony picking of two 10 cm dishes of the transfection with 1 g pIG35.55K DNA were trypsinised, pooled and expanded to give pool PER55K(1.0) The same was done for two dishes of the 1.5 μg transfection. The PER55K(1.0) cell pool was expanded and seeded in 4 T25 flasks at a density of $3.5 \times 10^6$ cells/flask for transfection to test virus generation. In addition, 3 T25 flasks with parental PER.C6 cells were seeded at the same density. pAdApt35.eGFP (an adapter plasmid containing the green fluorescent protein as marker gene; see example 4) was digested with PacI to liberate the adenoviral sequences from the plasmid backbone. pWE.Ad35.pIX-rITR (see, example 4) was digested with NotI to liberate the adenoviral sequences from the cosmid backbone. 2 flasks with PER.C6 cells and 2 flasks with PER55K(1.0) cells were transfected with 2 μg digested pAdApt35.eGFP and 6 μg digested pWE.Ad35.pIX-rITR each. One flask of each cell line was transfected with 8 μg pAdApt35.LacZ to monitor transfection efficiency. The remaining flask with PER55K(1.0) cells served as a negative control and was treated as the others but did not receive the transfection mixture. All transfections were performed with LipofectAmine (Invitrogen/Life Techn.) according to manufactures instructions using for each transfection a total of 8 μg DNA and 40 μl LipofectAmine reagent. The transfection mixture was removed after 4 hrs incubation and fresh culture medium was added. Transfections were done the day after seeding of the cells and again two days later cells in the 125 flasks were transferred to a T80 flask except for the LacZ control transfections. These were stained with X-gal solution after mild fixation. After five hours incubation with staining solution, the percentage of blue cells was estimated at approximately 90% in both flasks showing that transfection went well for both cell lines. Four days following the passage to the T80 flasks the transfected PER55K(1.0) cultures showed staring CPE (cytopathogenic effect, indicative of virus replication) with approximately 100 events/flask. The untransfected PER55K(1.0) cells were grown confluent with no evidence of CPE. In the transfected PER.C6 cultures only three CPE events were visible in the confluent monolayer of cells. Again three days later, the transfected PER55K(1.0) cultures showed fill CPE, with all cells rounded and detached in crumbs. In contrast, in the PER.C6 cultures the few events of CPE had not progressed and cells were still in monolayer. This confirms earlier observations that generation of E1-deleted Ad35-based viruses on PER.C6 is very inefficient Also the untransfected PER55K(1.0) cultures showed, as expected, a confluent monolayer with no CPE. The cells and medium in the PER55K(1.0) flasks with full CPE were harvested and subjected to two freeze/thaw cycles after which the cell debris was removed by centrifugation at 3000 rpm for 10 minutes in a table centrifuge. One of the resulting crude lysates was used to infect a fresh culture of PER55K(1.0) cells in a T175 flask (1.5 ml/flask). Cells and medium were harvested at full CPE four days later. This shows that infectious virus had formed in the initial transfections. GFP expression was confirmed by fluorescent microscopy of A549 cells infected with the crude lysate. The crude lysate was then used to analyse complementation of this E1-deleted Ad35.AdApt.eGFP virus in the individual clones as described below.

The above-described clones that were picked from the pIG35.55K transfected PER.C6 cells were expanded and were functionally tested for the ability to sustain replication of Ad35.AdApt.eGFP. Hereto, the clones were seeded at two densities in 6-well plates and one day later infected with 15 ml of the above described crude lysate. CPE was monitored the day after. Of the 146 clones tested in this way 19 gave fill CPE at day 2 or 3 and 68 gave full CPE at day 5 or 6. The remaining clones had only partial CPE or showed a few non-progressing events. The latter were indistinguishable from PER.C6 cells that were taken along as a negative control.

Based on these results a selection of 24 clones was made that were further screened for the ability to generate recombinant E1-deleted viruses following transfection of the pAdApt35.GFP adapter plasmid and the large pWE.Ad35.pIX-rITR cosmid clone. Hereto, clones were plated in T25 flasks and transfected with 2 μg of the adapter and 6 μg of the backbone plasmid using LipofectAmine as described above. Two days following the transfection, cells were transferred to T80 flasks to prevent overconfluency of the cultures Of the 24 clones 5 gave full CPE three days after passage to T80 and another 13 clones gave progressing to full CPE the day after. The remaining 6 clones showed no CPE or only starting. In comparison: routine generation of E1-deleted Ad5 vectors on PER.C6 cells generally results in full CPE four to six days after transfer to T80 flasks.

This shows that the new clones efficiently complement E1-deleted adenovirus vectors. One of the clones (clone #16) described above was used to generate and produce multiple batches of E1 and E1/E3 deleted Ad35 viruses containing different transgenes. Hereto, virus in crude lysates resulting from transfections as described above, but using different adapter plasmids, were plaque purified on the new cell line. Single plaques were tested for transgene activity and then amplified for medium scale production in 4–8 triple layer flasks (3×175 cm/flask). Cells were harvested at full CPE and the virus was released and purified as routinely done for adenoviruses and described in example 1. The extraction step with freon to remove cellular debris was, however, replaced by a centrifugation step. Thus after incubation with DnaseI, the cell debris was centrifuged in conical 50 ml tubes (Greiner) at 8000 rpm in a table top centrifuge (Beckman Coulter Allegra 21R with fixed angle rotor) for 30 minutes at 4° C. This step is repeated in a fresh 50 ml tube untill the supernatant was clear (usually one time). The amount of virus particles was determined by HPLC (Shabram et al., 1997). Table IV presents the yields after downstream processing of medium scale productions of E1- and E1/E3-deleted Ad35 viruses on triple layer flasks with PER55K clone #16 cells. The amount of purified virus particles is comparable with the yields of Ad5-based vectors on PER.C6 cells.

We conclude that we have generated multiple cell lines that efficiently complement fully E1-deleted Ad35-based vectors. Thus, Ad35 E1B-55K expression in an Ad5 complementing cell line facilitates replication of Ad35 vectors.

Example 10

New Complementing Cell Lines from Primary Cells.

Example 8 described the generation of construct pIG535, a hybrid Ad5E1A-Ad35 E1B expression plasmid. pCC536s and pIG536 are also hybrid Ad5-Ad35 E1 constructs but with the E1A region, E1B promoter and most of the E1B-19K gene derived from Ad5 and most of the E1B-55K gene derived from Ad35. Constructs pCC536s and pIG536 differ only in the heterologous poly adenylation sequence that terminates the E1B transcript: pIG536 has the HBV pA sequence and pCC536s has a synthetic pA sequence (SpA). The SpA sequence consists of the upstream sequence element (USE) of the human C2 complement gene (Moreira et al., 1995) and the synthetic pA sequence (SPA) described by Levitt et al., 1989.

The synthetic polyA sequence is build up using the following oligos: C2SPA-1: 5'-CCC TGC AGG GAC TTG ACT CAT GCT TGT TTC ACT TTC ACA TGG AAT TTC CCA GTT ATG AAA TTA ATA AAG-3' (SEQ ID NO:37) and C2SPA-2: 5'-GTC TAG ACA CAC AAA AAA CCA ACA CAC TAT TGC AAT GAA AAT AAA TTT CCT TTA TTA ATT TCA TAA CTG-3' (SEQ ID NO:38). Oligonucleotides were mixed at 10 μM concentration in 1× annealing buffer (10 mM Tris HCl pH 7.5, 100 mM NaCl, 1 mM EDTA) and, using a PCR machine, the solution was heated to 94° C. for 5 minutes and then cooled down to 65° C. at 0.5° C./second and after incubation at 65° C. for 5 minutes further cooled down to 20° C. at 0.05° C./second. Subsequently, 10 μl 2 mM dNTPs, 0.5 μl 1M MgCl2 and 3 μl Klenow fragment (New England Biolabs) was added to 87 μl of the annealed sample and the mixture was incubated at room temperature for 30 minutes. 1 μl of the annealed and Klenow treated sample was then amplified using the following primers:

C2for: 5'-CGG GAT CCC CTG CAG GGA CTT GAC-3' (SEQ ID NO:39) and

SPArev: 5'-TTG CGA CTT AAG TCT AGA CAC ACA AAA AAC C-3' (SEQ ID NO:40) using Pwo DNA polymerase (Roche) according to manufacturers instructions but with addition of DMSO (Sigma) to a final concentration of 3%. The PCR program was set at 94° C. for 2 minutes, followed by 30 cycles of (94° C. for 30", 55° C. for 30" and 72° C. for 20"). Where in this document PCR programs are described "means time in minutes and" means time in seconds. The amplified DNA was then purified using the QIAquick PCR purification kit (Qiagen) and digested with XbaI and SbfI. The digested product was then again purified with the PCR purification kit to remove the small digested ends. Construct pIG270 was also digested with XbaI and SbfI (isoschizomer of Sse83871) and the resulting 5.9 kb vector containing fragment was isolated from gel using the GeneClean II kit (Bio101, Inc). The treated vector and PCR insert were then ligated to give pCC271 (FIG. 28). pCC271 thus contains the PGK promoter, the Ad35 E1 region (nucl. 468 to and including 3400 from Ad35 sequence in example 3 and SEQ ID NO:44) and the synthetic pA (SpA). The synthetic pA sequence was then also cloned into the construct pIG535 as follows.

pIG535 was digested with EcoRI, PstI and ScaI (All enzymes from New England Biolabs digested in NEB buffer 3) and the 3 kb insert corresponding to chimeric Ad5-Ad35 E1 region was purified using the GeneClean II kit (Bio 101, Inc.). Construct pCC271 was digested with EcoRI and PstI and the 3 kb vector fragment containing the SpA and PGK promoter was isolated as above. Both isolated fragments were ligated and transformed into STBL-2 competent cells (Invitrogen/LifeTechnologies) to give pCC535s (FIG. 29). pCC535s contains the same Ad5-Ad35 E1 sequences as pIG535 however, a different pA sequence.

For the construction of pCC536s, a subclone was made with the new hybrid E1B sequences. Hereto, Ad5 E1A/ E1B21K sequences were amplified using the primers 5AK: 5'-GAG CGA AGA AAC CCA TCT GAG-3' (SEQ ID NO:32) and 2155R: 5'-GGT CCA GGC CGG CTC TCG G-3' (SEQ ID NO:33) with pIG.E1A.E1B (see, example 6 and FIG. 12) as template DNA using Pwo DNA polymerase (Roche) according to manufacturers instructions and in addition a final concentration of 3% DMSO. The program was set at: 94° C. for 2' followed by 30 cycles of (94° C. for 30", 58° C. for 30" and 72° C. for 30") and ended with 68° C. for 8'. This resulted in a 210 bp fragment corresponding to nucl. 2022–2233 of the Ad5 sequence. A second PCR was performed on pCC271 with primers 2155F: 5'-CCG AGA GCC GGC CTG GAC C-3' (SEQ ID NO:41) and

35F10: 5'-GCT CTA GAC CTG CAG GTT AGT CAG TTT CTT CTC CAC TG-3' (SEQ ID NO:21).

The same PCR program was used but now with an elongation time of 90". The resulting 1.3 kb fragment corresponds to nucl. 2112 to 3400 of the Ad35 sequence with an SbfI site at the 3'end. Note that primers 2155F (SEQ-ID NO:41) and 2155R (SEQ ID NO:33) are fully complementary allowing assembly of the two fragments as follows:

Both PCR fragments were purified from gel using the Qiagen gel extraction kit. Aliquots of the purified samples were then mixed in equimolar ratio and used as template for an assembly PCR amplification with primers 5AK (SEQ ID NO:32) and 35F10 (SEQ ID NO:21) with Pwo DNA polymerase as above using the program settings: 94° C. for 2', and 5 cycles of (94° C. for 30", 60° C. for 30" and 72° C. for 2') followed by 25 cycles of (94° C. for 30", 58° C. for 30" and 72° C. for 90"). The resulting 1.5 kb fragment was purified from gel using the QIAquick gel extraction kit (Qiagen), ligated to the pCR-Script/Amp cloning vector (Stratagene) and transformed into DH5a competent cells (Invitrogen/Life Technologies) resulting in pCR535E1B (FIG. 30). This construct was checked by restriction analysis and sequencing to confirm correct amplification of target sequences.

pCR535E1B was then digested with NotI and protruding ends were made blunt with Klenow fragment. The DNA was then purified using the QIAquick PCR purification kit (Qiagen) and eluted DNA was digested with PstI. The 1.5 kb fragment containing the chimeric E1 sequences from the pCRS35E1B vector was purified from gel using the GeneClean II kit (Bio101, Inc.). This fragment was ligated to vector pCC535s digested with PvuII and PstI, and transformed into STBL-2 competent cells (Invitrogen/Life Technologies) to give pCC2155s (FIG. 31). To complete the pCCS36s construct Ad5-E1 sequences were then cloned into the pCC2155s subclone. Hereto, pIG.E1A.E1B was digested with EcoRI and KpnI and the 1.6 kb fragment corresponding to Ad5 E1A and Ad5 E1B 21K (nucl. 459 to 2048 of the Ad5 sequence) was isolated from gel using the GeneClean kit. pCC2155s was digested with EcoRI and KpnI and the vector containing fragment was also gel purified. Ligation of both isolated fragments and transformation into DH10B electrocompetent cells (Invitrogen/Life Technologies) resulted in pCC536s (FIG. 32). The hybrid E1B sequences are shown in FIG. 37 in more detail. FIG. 37A shows an alignment of protein sequences of E1B-21K in the pCC536s construct with wild type (wt) Ad35 and Ad5 sequences. As can be seen most of the E1B-21K protein in pCC536s is derived from Ad5 except for the C-terminal 6 amino acids that are identical to Ad35 E1B-21K. FIG. 37B shows the same alignment for the E1B-55K proteins. In this case the N-terminal amino acids of pCC536s are identical to Ad5 upto aa 65. The remainder is identical to Ad35 E1B-55K. Obviously, different hybrid E1B-55K constructs can be designed using the general method oulined above whithout departing from the invention.

Construct pIG536 was made by replacing a fragment with the SpA in pCC536s with the corresponding fragment from pIG270 (example 6, FIG. 14) containing the HBVpA. Hereto, pIG270 was digested with BamHI and BglI and the 1.8 kb insert was isolated from gel using the GeneClean II kit (Bio 101, Inc.). pCC536s was digested with the same enzymes and the 4.8 kb vector containing fragment was purified from gel as above. Ligation of both isolated fragments and transformation into STBL-2 competent cells (Invitrogen/Life Technologies) gave construct pIG536 (FIG. 33).

The generated E1 constructs were tested in primary baby rat kidney (BRK) cells as described in example 6. The results (Table V) confirm earlier observations that Ad5-E1 genes more efficiently transform primary BRK cells than Ad35 E1 genes. The chimeric Ad5-Ad35 E1 expression constructs, pCC535s and pCC536s, produced more transformed colonies than the fill Ad35 E1 constructs, pIG270 and pCC271. Furthermore, the use of a synthetic poly adenylation sequence in pCC535s resulted in slightly more foci compared to the HBVpA variant pIG535.

Human embryonic retinoblast (HER) cells were isolated from the eyes of aborted fetuses of 18 and 21 weeks of age. The eyes were brought in a 6 cm dish with PBS and cleared from outside tissue. An incision was made to reach the inner side and the gray cell layer at the inner back of the eyes containing the retinoblasts, was scrape off. This layer was transferred to a 14 ml tube in 2 ml of PBS and tissue was allowed to sediment after which the PBS was removed. 2 ml trypsin (0.25%, no EDTA, GibcoBRL) was added and incubated for 5 minutes at 37° C. with occasional swirling. Tissue pieces were allowed to sediment and 1 ml trypsin with cells was transferred to a new tube. To this tube 4 ml culture medium (DMEM with 10% FCS) was added and the tube was stored on ice. The remaining tissue pieces in trypsin were brought in a 6 cm dish and cut into smaller pieces. These were, after addition of 2 ml fresh trypsin, again incubated in a 14 ml tube at 37° C. with occasionally swirling. Then this mixture was added to the first isolated cells in culture medium and the total was centrifugated at 1000 rpm in a table top centrifmuge. Supernatant was removed and cells were resuspended in 10 ml of culture medium. The isolated HER cells were plated in two 6 cm dishes and incubated at 37° C./10% CO2. Upon 90% confluency cultures were split 1:3 and further incubated. This procedure was repeated until enough dishes were obtained to be used for transfection and further culturing. Transfections were performed at different passage numbers using the $CaPO_4$ cotransfection kit (Invitrogen/Life Technologies) according to manufacturers instructions. For each dish (50–70% confluency) 20 $\mu$g DNA was used. Initial transfections were performed with pIG.E1A E1B, an Ad5-E1 expression cons, and with pIG535, the hybrid Ad5-E1A/Ad35-E1B expression construct. 2–3 weeks following transfection transformed foci became visible in the pIG.E1A.E1B transfected dishes. On average 15–20 foci/dish were found in the dishes that were transfected with pIG.E1A.E1B. Over 30 clones were picked and transferred to 96well plates. Upon confluency cells were passaged to larger culture plates or flasks and finally viable frozen in ampoules in $liqN_2$ from a T175 flask. All picked clones were established in this way. Transformed foci appeared much later in the dishes that were transfected with pIG535, the first around five weeks following transfection. On average 3–4 clones were found per dish. A total of 46 clones were picked from 7 weeks to 3 months aft transfections of which 14 were viable and could be passaged multiple times. Of these, 2 clones (clone #45 and #75) were grown up to a T175 flask and viable frozen in ampoules in $liqN_2$.

Primary HER cells were also transfected with constrcts pCC535s and pCC536s. Transfection of pCC535s let to an average of 2 clones/dish and a total of 50 clones were picked. Of these picked clones 2 could be established. From the transfection with pCCS36s, at least one clone could be established.

The above-described experiments show that primary HER cells can be transformed with hybrid Ad5-Ad35 E1 sequences. The efficiency of transformation was lower than obtained with the complete Ad5 E1 region. We then tested whether the new cell lines could complement recombinant Ad35-based E1-deleted vectors. Hereto, the clone #45 that was obtained from the pIG535 transfection was seeded in 725 flasks at a density of $7\times10^6$ cells/flask and infected with Ad35AdApt.eGFP virus (see example 9) at a multiplicity of infection (moi) of 5 and 25 virus particles/cell. Full CPE was seen at days 4 and 5 for the moi 25 and 5 respectively. As a comparison parallel cultures of clone #45 cells that were infected with Ad5.AdApt.eGFP viruses gave full CPE at days 7 and 8 for moi 25 and 5 respectively. The initial infection efficiency was comparable for Ad5 and Ad35 viruses, ~80% (moi=5) and ~95% (moi=25) of the cells were infected with GFP virus one day following infection as measured by fluorescence microscopy. Cells from clone #75 were seeded in a 6well plate at a density of $2\times10^6$ cells/well and infected with Ad35.AdApt.eGFP or Ad5.AdApt.eGFP at moi 5 (VP/cell). Again initial infection efficiency was comparable for both viruses. Full CPE was observed at day 4 in case of Ad35.AdApt.eGFP infection whereas Ad5AdApt.eGFP infected clone #75 cells gave fill CPE on day 7. The difference in replication efficiency on Ad35 complementing cells between Ad35 and Ad5 recombinant vectors is even more clear when virus is generated by plasmid transfection. This is exemplified by the following transfection experiment. Clone #45 cells were seeded in T25 flasks at a density of $3.5\times10^6$ cells and transfected three days later using LipofectAmine reagent (Invitrogen/Life Technologies) according to manufacturers instructions and described above. 2 $\mu$g pAdApt35.eGFP adapter plasmid digested with PacI was cotransfected with 6 $\mu$g pWE.Ad35.pIX-rITR or pWE.Ad35.pIX-rITRΔE3 backbone cosmid digested with NotI. 2 $\mu$g pAdApt.eGFP (Ad5 adapter plasmid, described in WO 00/70071) digested with PacI was cotransfected with 6 $\mu$g pWE.Ad5.AflII-rITRsp (Ad5 backbone plasmid, described in WO 00/70071) also digested with PacI. One T25 was not transfected and served as a negative control. One day later transfection efficiencies were monitored by fluorescent microscopy and estimated at 10–15% in all eGFP transfections. Three days following transfection cells were transferred to T80 flasks and further incubated at 37° C./10% $CO_2$. Again three days later CPE events were becoming visible in the cultures transfected with the pAdApt35.eGFP and the pWE.Ad35pIX-rITR+ or −E3. The transfections with the E3-deleted backbone contained more green fluorescent cells and more CPE events. The transfection with Ad5 plasmids showed only around 20% green fluorescent cells, of which most were dying, and no CPE events. Two days later this difference had become bigger since cultures transfected with the pAdApt35.eGFP and the pWE.Ad35pIX-rITRΔE3 clearly showed 80% CPE and cultures transfected with the pAdApt35.eGFP and the pWE.Ad35pIX-rITR constructs showed progressing CPE events. The Ad5 transfected culture did not show any progression. Table VI summarizes these results.

We conclude that the new complementing cell lines described above efficiently sustain replication of E1 deleted Ad35-based viruses and that the generation and replication of E1 deleted Ad5-based viruses is less efficient Apparently, also Ad35-E1B55K proteins do not form a functional complex with Ad5-E4-Orf6 proteins. Thus the serotype specificity for complementation is now also shown for recombinant Ads vectors on Ad35 packaging cells.

Example 11

Generation of pWE.Ad.pIX-rITRΔE3.

The early region-3 of human adenoviruses contains multiple coding regions for proteins that interfere with the host immune response to adenoviral infection. When adenoviral vectors are used as vaccine carrier such interference is unwanted. Therefore, we constructed an Ad35 backbone cosmid lacking the E3 region.

Hereto, construct pBr.Ad35.PRn (FIG. 34; described in example 13 in publication EP 1 054 064 A1) was digested with StuI and MluI and the 17.3 kb vector fragment was purified from low melting point (LMP) gel using agarase enzyme (Roche) according to manufactures instructions. Next, a PCR fragment was generated on pBr.Ad35.PRn using primers:

35E3for: 5'-AAT GAC TAA TGC AGG TGC GC-3' (SEQ ID NO:42) and

35E3rev: 5'-CGA CGC GTT GTA GTC GTT GAG CTT CTA G-3' (SEQ ID NO:43). For the amplification Pwo DNA polymerase (Roche) was used according to manufactures instructions and program set at: 94° C. for 2', 30 cycles of (94° C. for 30", 58° C. for 30'" and 72° C. for 1') and a final incubation at 68° C. for 8'. The 833 bp PCR product was purified using the QIAquick PCR purification kit (Qiagen) and digested with MluI and StuI. The digested DNA was purified from gel using the QIAquick gel extraction kit (Qiagen). Both isolated fragments were ligated and transformed into DH5a competent cells (Invitrogen/Life Technologies) to give pBr.Ad35.PRnΔE3 (FIG. 35). The plasmid was checked by restriction analysis and sequencing of the PCR amplified insert. The E3 deletion was then cloned into the pWE.Ad35.pIX-rITR cosmid backbone. Hereto, pWE.Ad35.pIX-rITR (see example 4 and FIG. 7) was digested with PacI and the DNA was purified by precipitation with isopropanol and washing with 70% EtOH. Following resuspension in milliQ water, the DNA was digested with SwaI and the 22.8 kb vector containing fragment was purified from LMP gel using agarase enzyme as above. Construct pBr.Ad35.PRnΔE3 was digested with PacI and SwaI in the same manner and the 16.6 kb fragment was also isolated using agarase enzyme. Both isolated fragments were ligated using 0.5–0.6 μg of each fragment Ligated fragments were then packaged using λ-phage packaging extracts (Stratagene) according to manufacturers instructions and mixed with STBL-2 cells. Bacteria were plated on LB+Amp plates and resulting colonies were analyzed for the presence of the correct construct. This gave construct pWE.Ad35.pIX-rITRΔE3 (FIG. 36). The E3 deletion extends from nucl. 27648 to 30320 of the Ad35 sequence (example 3) and thus spans a 2.6 kb region.

Cotransfection of NotI digested pWE.Ad35.pIX-rITRΔE3 and pIPsp-1 digested pAdApt35.eGFP onto PER55-clone #16 cells (see example 9) as described above gave rise to GFP expressing Ad35-based viruses. Upon isolation of viral DNA from these viruses, PCR amplification of the E3 region showed that the viruses were deleted for 2.6 kb of E3 sequences as expected.

TABLE I

| Serotype # | Elution [NaCl] mM | VP/ml | CCID50 | $\log_{10}$ VP/CCID50 ratio |
|---|---|---|---|---|
| 1 | 597 | $8.66 \times 10^{10}$ | $5.00 \times 10^7$ | 3.2 |
| 2 | 574 | $1.04 \times 10^{12}$ | $3.66 \times 10^{11}$ | 0.4 |
| 3 | 131 | $1.19 \times 10^{11}$ | $1.28 \times 10^7$ | 4.0 |
| 4 | 260 | $4.84 \times 10^{11}$ | $2.50 \times 10^8$ | 3.3 |
| 5 | 533 | $5.40 \times 10^{11}$ | $1.12 \times 10^{10}$ | 1.7 |
| 6 | 477 | $1.05 \times 10^{12}$ | $2.14 \times 10^{10}$ | 1.7 |
| 7 | 328 | $1.68 \times 10^{12}$ | $2.73 \times 10^9$ | 2.4 |
| 9 | 379 | $4.99 \times 10^{11}$ | $3.75 \times 10^7$ | 4.1 |
| 10 | 387 | $8.32 \times 10^{12}$ | $1.12 \times 10^9$ | 3.9 |
| 12 | 305 | $3.64 \times 10^{11}$ | $1.46 \times 10^7$ | 4.4 |
| 13 | 231 | $4.37 \times 10^{12}$ | $7.31 \times 10^8$ | 3.8 |
| 15 | 443 | $5.33 \times 10^{12}$ | $1.25 \times 10^9$ | 3.6 |
| 16 | 312 | $1.75 \times 10^{12}$ | $5.59 \times 10^8$ | 3.5 |
| 17 | 478 | $1.39 \times 10^{12}$ | $1.45 \times 10^9$ | 3.0 |
| 19 | 430 | $8.44 \times 10^{11}$ | $8.55 \times 10^7$ | 4.0 |
| 20 | 156 | $1.41 \times 10^{11}$ | $1.68 \times 10^7$ | 3.9 |
| 21 | 437 | $3.21 \times 10^{11}$ | $1.12 \times 10^8$ | 3.5 |
| 22 | 365 | $1.43 \times 10^{12}$ | $5.59 \times 10^7$ | 3.4 |
| 23 | 132 | $2.33 \times 10^{11}$ | $1.57 \times 10^7$ | 4.2 |
| 24 | 405 | $5.12 \times 10^{12}$ | $4.27 \times 10^8$ | 4.1 |
| 25 | 405 | $7.24 \times 10^{11}$ | $5.59 \times 10^7$ | 4.1 |
| 26 | 356 | $1.13 \times 10^{12}$ | $1.12 \times 10^8$ | 4.0 |
| 27 | 342 | $2.00 \times 10^{12}$ | $1.28 \times 10^8$ | 4.2 |
| 28 | 347 | $2.77 \times 10^{12}$ | $5.00 \times 10^7$ | 4.7 |
| 29 | 386 | $2.78 \times 10^{11}$ | $2.00 \times 10^7$ | 4.1 |
| 30 | 409 | $1.33 \times 10^{12}$ | $5.59 \times 10^8$ | 3.4 |
| 31 | 303 | $8.48 \times 10^{10}$ | $2.19 \times 10^7$ | 3.6 |
| 33 | 302 | $1.02 \times 10^{12}$ | $1.12 \times 10^7$ | 5.0 |
| 34 | 425 | $1.08 \times 10^{12}$ | $1.63 \times 10^{11}$ | 0.8 |
| 35 | 446 | $3.26 \times 10^{12}$ | $1.25 \times 10^{11}$ | 1.4 |
| 36 | 325 | $9.26 \times 10^{12}$ | $3.62 \times 10^9$ | 3.4 |
| 37 | 257 | $5.86 \times 10^{12}$ | $2.8 \times 10^9$ | 3.3 |
| 38 | 337 | $3.61 \times 10^{12}$ | $5.59 \times 10^7$ | 4.8 |
| 39 | 241 | $3.34 \times 10^{11}$ | $1.17 \times 10^7$ | 4.5 |
| 42 | 370 | $1.95 \times 10^{12}$ | $1.12 \times 10^8$ | 4.2 |
| 43 | 284 | $2.42 \times 10^{12}$ | $1.81 \times 10^8$ | 4.1 |
| 44 | 295 | $8.45 \times 10^{11}$ | $2.00 \times 10^7$ | 4.6 |
| 45 | 283 | $5.20 \times 10^{11}$ | $2.99 \times 10^7$ | 4.2 |
| 46 | 282 | $9.73 \times 10^{12}$ | $2.50 \times 10^8$ | 4.6 |
| 47 | 271 | $5.69 \times 10^{11}$ | $3.42 \times 10^7$ | 4.2 |
| 48 | 264 | $1.68 \times 10^{12}$ | $9.56 \times 10^8$ | 3.3 |
| 49 | 332 | $2.20 \times 10^{12}$ | $8.55 \times 10^7$ | 4.4 |
| 50 | 459 | $7.38 \times 10^{12}$ | $2.80 \times 10^9$ | 3.4 |
| 51 | 450 | $8.41 \times 10^{11}$ | $1.88 \times 10^8$ | 3.7 |

Legend to Table I:
All human adenoviruses used in the neutralization experiments were produced on PER.C6 cells (Fallaux et al., 1998) and purified on CsCl as described in example 1. The NaCl concentration at which the different serotypes eluted from the HPLC column is shown. Virus particles/ml (VP/ml) were calculated from an Ad5 standard. The titer in the experiment (CCID50) was determined on PER.C6 cells as described in Example 1 by titrations performed in parallel with the neutralization experiment. The CCID50 is shown for the 44 viruses used in this study and reflects the dilution of the virus needed to obtain CPE in 50% of the wells after 5 days. The ratio of VP/CCID50 is depicted in $\log_{10}$ and is a measurement of the infectivity of the different batches on PER.C6 cells.

TABLE II

AdApt35.LacZ viruses escape neutralization by human serum.

| Virus | no serum | Human serum dilution | | | | |
|---|---|---|---|---|---|---|
| | | 10× | 50× | 250× | 1250× | 6250× |
| AdApt5.LacZ moi: 5 VP/cell | 100% | 0% | 0% | 1% | 40% | 80% |
| AdApt35.LacZ 250 μl crude lysate | 100% | 100% | 100% | 100% | 100% | 100% |

TABLE III

The numbers of foci obtained with the different E1 expression constructs in BRK transformation experiments. Average # of foci/dish:

| | Construct | 1 μgr | 5 μgr |
|---|---|---|---|
| Experiment 1 | pIG.E1A.E1B | nd | 60 |
| | pIG.E1A.E1B | nd | 35 |
| | pRSVAd35.E1 | 0 | 3 |
| | pIG.Ad35.E1 | 3 | 7 |
| Experiment 2 | pIG.E1A.E1B | 37 | nd |
| | pIG.Ad35.E1 | nd | 2 |
| Experiment 3 | pIG.E1A.E1B | nd | 140 |
| | pIG.Ad35.E1 | nd | 20 |
| | pIG270 | nd | 30 |

TABLE IV

Yields of E1- and E1/E3- deleted Ad35 viruses on clone #16 cells produced on triple layer flasks.

| Virus | Scale(T175III flasks) | Total # of Virus Particles after DSP | VP/cell |
|---|---|---|---|
| Ad35.AdApt.eGFP | 4 | $7.5 \times 10^{11}$ | 2500 |
| Ad35.ΔE3.AdApt.empty | 8 | $2 \times 10^{12}$ | 3300 |
| Ad35.ΔE3.AdApt.LacZ | 8 | $3.8 \times 10^{11}$ | 600 |
| Ad35.ΔE3.AdApt.MV-F | 4 | $8.8 \times 10^{11}$ | 2900 |
| Ad35.ΔE3.AdApt.MV-H | 8 | $2.6 \times 10^{12}$ | 4250 |

TABLE V

Transformation efficiencies on BRK cells with different Ad-E1 expression constructs.

| | Construct | Transfected DNA (μg) | # foci per dish |
|---|---|---|---|
| Experiment 1 | pIG.E1A.E1B | 5 | 44 |
| | pIG270 | 5 | 0 |
| | pCC271 | 5 | 0 |
| | pIG535 | 5 | 1 |
| | pCC535s | 5 | 2.5 |
| Experiment 2 | pIG.E1A.E1B | 4 | 15 |
| | pCC271 | 4 | 0 |
| | pCC535s | 4 | 3 |
| | pCC536s | 4 | 3 |

TABLE VI

Generation of recombinant Ad35 viruses on the new established complementing cell line clone #45.

| | GFP Expression × | | | |
|---|---|---|---|---|
| Transfected constructs | Day 1 | Day 3 | Day 6 | Day 8 |
| pAdApt35.eGFP + pWE.Ad35.pIX-rITR | 15% | 20% | 30% | 50% |
| pAdApt35.eGFP + pWE.Ad35.pIX-rITRΔE3 | 10% | 25% | 40–50% | 100% |
| pAdApt5.eGFP + pWE.Ad5.AflII-rITR | 15% | 25% | 20% | 20% |
| untransfected | 0% | 0% | 0% | 0% |

| | CPE events × | | | |
|---|---|---|---|---|
| Transfected constructs | Day 1 | Day 3 | Day 6 | Day 8 |
| pAdApt35.eGFP + pWE.Ad35.pIX-rITR | 0 | 0 | 1 | several |
| pAdApt35.eGFP + pWE.Ad35.pIX-rITRΔE3 | 0 | 0 | several | 80% |
| pAdApt5.eGFP + pWE.Ad5.AflII-rITR | 0 | 0 | 0 | 0 |
| untransfected | 0 | 0 | 0 | 0 |

REFERENCES

Abrahamsen, K., Kong, H-L., Mastrangeli, A., Brough, D., Lizonova, A., Crystal, R. G. and Falck-Pedersen, E. (1997). Construction of an adenovirus type 7a E1A⁻ vector. J. Virol. 71, 11, p8946–8951.

Babiss, L. E. and Ginsberg, H. S. (1984). Adenovirus type 5 early region 1b gene product is required for efficient shutoff of host protein synthesis. 1. Virol. 50, p202–2122.

Babiss, L. E., Ginsberg, H. S. and Darnell, J. J. (1985). Adenovirus E1B proteins are required for accumulation of late viral mRNA and for effects on cellular mRNA translation and transport. Mol. Cell. Biol. 5, p2552–2558.

Bernards, R., Houweling, A. Schrier, P. I, Bos, J. L. and van der Eb, A. J. (1982). Characterization of cells transformed by Ad5/Ad12 hybrid early region 1 plasmids. Virology 120, p422–432.

Bonnerot, C., Rocancourt, D., Briand, P., Grimber, G. and Nicolas, J. F. (1987). A beta-galactosidase hybrid protein targeted to nuclei as a marker for developmental studies. Proc. Natl. Acad. Sci. USA 84(19), p6795–6799.

Bos, J. L., Polder, L. J., Bernards, R., Schrier, P., van den Elsen P. J., van der Eb, A. J. and van Ormondt, H. (1981). The 2.2 kb mRNA of the E1B region of human adenovirus type 12 and 5 directs the synthesis of two major tumor antigens from different AUG triplets. Cell 12, p721–732.

Bridge, E. and Ketner, G. (1990). Interaction of adenoviral E4 and E1b products in late gene expression. Virology 174, p345–353.

Bridge, E., Medghalchi, S., Ubol, S., Leesong, M. and Ketner, G. (1993). Adenovirus early region 4 and viral DNA synthesis. Virology 193, p794–801.

Brough, D. E., Lizonova, A., Hsu, C., Kulesa, V. A. and Kovesdi, I. (1996. A gene transfer vector-cell line system for complete functional complementation of adenovirus early regions 1 and 4. J. Virol. 70, p6497–501.

Fallaux, F. J., Kranenburg, O., Cramer, S. J., Houweling, A., van Ormondt, H., Hoeben, R. C. and van der Eb, A. J. (1996). Characterization of 911: a new helper cell line for the titration and propagation of early region 1-deleted adenoviral vectors. Hum. Gene Ther. 7 (2), p215–222.

Fallaux, F. J., Bout, A., van der Velde, I., van den Wollenberg, D. J., Hehir, K. M., Keegan, J., Auger, C., Cramer, S. J., van Ormondt, H., van der Eb, A. J., Valecio, D. and Hoeben, R. C. (1998). New helper cells and matched early region 1-deleted adenovirus vectors prevent generation of replication competent adenoviruses. Hum. Gene Ther. 9, 1909–1917.

Gallimore, P. H., Grand, R. J. A. and Byrd, P. J. (1986). Transformation of human embryo retinoblasts with simian virus 40, adenovirus and ras oncogenes. AntiCancer Res. 6, p499–508.

Gossen M., and H. Bujard (1992). Tight control of gene expression in mammalian cells by tetracycline-responsive promoters. Proc. Natl. Acad. Sci. USA 89, 5547–5551.

Graham, F. O., Smiley, J., Russell, W. and Nairn, R. (19770. Characteristics of a human cell line transformed by DNA from human adenovirus type 5. J. Gen. Virol. 36, p59–72.

Grand, R. J. A., Parkhill, J., Szestak, T., Rookes, S. M., Roberts, S. and Gallimore, P. H. (1999). Definition of a major p53 binding site on Ad2-E1B-58K protein and a possible nuclear localization signal on the Ad12-E1B-54K protein. Oncogene 18, p955–965.

Han, J., Sabbatini, P., Perez, D., Rao, L., Modha, D. and White, E. (1996). The E1B19K protein blocks apoptosis by interacting with and inhibiting the p53-inducible and death-promoting Bax protein. Genes Dev. 10 (4), p461–477.

Jochemsen, A. G., Peltenburg L. T., te Pas, M. F., de Wit, C. M., Bos, J. L. and van der Eb, A. J. (1987). Activation of adenovirus 5 E1A transcription by region E1B in transformed primary rat cells. EMBO J. 6 (11), p3399–3405.

Moreira, A., Wollerton, M., Monks, J. and Proudfoot, N.J. (1995). Upstream sequence elements enhance poly(A) site efficiency of the C2 complement gene and are phylogenetically conserved. EMBO J., 14 (15), p3809–3819.

Leppard, K. N. and Shenk, T. (1989). The adenovirus E1B-55 kd protein influences mRNA tranport via an intranuclear effect on RNA metabolism. EMBO J. 8, p2329–2336.

Levitt, N., Briggs, D., Gil, A. and Proudfoot, N.J. (1989). Definition of an efficient synthetic poly(A) site. Genes Dev. 3, p1019–1025.

Pilder, S., Moore, M., Logan, J. and Shenk, T. (1986). The adenovirus E1B-55K transforming polypeptide modulates transport or cytoplasmic stabilization of viral and host cell mRNAs. Mol. Cell. Biol. 6, p470–476.

Rao, L., Debbas, M., Sabbatini, P., Hockenbery, D., Korsmeyer, S. and White, E. (1992). The adenovirus E1A proteins induce apoptosis, which is inhibited by the E1B-19-kDa and Bcl-2 proteins. Proc. Natl. Acad. Sci. USA 89, p7742–7746.

Rubenwolf, S., Schütt, H., Nevels, M., Wolf, H. and Dobner, T. (1997). Structural analysis of the adenovirus type 5 E1B-55-kilodalton-E4orf6 protein complex. J. Virol. 71, p1115–1123.

Singer-Sam, J., Keith, D. H., Tani, K, Simmer, R. L., Shively, L., Lindsay, S., Yoshida, A. and Riggs, A. D. (1984). Sequence of the promoter region of the gene for human X-linked 3-phosphoglycerate kinase. Gene 32 (3), p409–117.

White, E. and Cipriani, R (1990). Role of adenovirus E1B proteins in transformation: Altered organization of intermediate filaments in transformed cells that express the 19-kilodalton protein. Mol. Cell. Biol. 10, p120–130.

White, E. (1995). Regulation of p53-dependent apoptosis by E1A and E1B. In: The molecular repertoire of adenoviruses HI. Eds. Doerfler, W. and Böhm, P. Springer-Verlag Berlin Heidelberg 1995, p33–58.

White, E. (1996). Life, death, and the pursuit of apoptosis. Genes Dev. 10 (1), p1-15.

Yew, P. R, Kao, C. C. and Berk, A. J. (1990). Dissection of functional domains in the adenovirus 2 early region 1B-55K polypeptide by suppressor-linker insertional mutagenesis. Virology 179, p795–805.

Yew, P. R. and Berk, A. J. (1992). Inhibition of p53 transactivation required for transformation by adenovirus early region 1B protein. Nature 357, p82–85.

Simonsen, C. C. and Levinson, A. D. (1983). Analysis of processing and polyadenylation signals of the hepatitis B virus surface antigen gene by using simian virus 40-hepatitis B virus chimeric plasmids. Mol. and Cell. Biol. 3 (12), p2250–2258.

Zantema, A., Fransen, J. A., Davis, O. A., Ramaekers, F. C., Vooijs, G. P., DeLeys, B. and van der Eb, A. J. (1985). Localization of the E1B proteins of adenovirus 5 in transformed cells, as revealed by interaction with monoclonal antibodies. Virology 142, p44–58.

Zantema, A. and van der Eb, A. J. (1995). Modulation of gene expression by adenovirus transformation. In: The molecular repertoire of adenoviruses III. Eds. Doerfler, W. and Böhm, P.Springer-Verlag Berlin Heidelberg 1995, p1–23.

What is claimed is:

1. A process for complementing a recombinant adenovirus, the process comprising:

providing a packaging cell that complements recombinant adenovirus based on adenovirus type 35, wherein said packaging cell is a transformed primary, diploid human cell, said transformed primary, diploid human cell having been transformed by adenovirus E1 coding sequences either operatively linked on one DNA molecule or located on two separate DNA molecules, said adenovirus E1 coding sequences being operatively linked to regulatory sequences enabling transcription and translation of encoded proteins with said recombinant adenovirus; and culturing said packaging cell to allow for complementation.

2. The process according to claim 1, further comprising harvesting complemented recombinant adenovirus.

3. The process according to claim 1, wherein said recombinant adenovirus is a subgroup B adenovirus.

4. The process according to claim 3, wherein said recombinant adenovirus is adenovirus type 35.

5. The process of claim 1, wherein the packaging cell further comprises a DNA encoding at least E4-orf6 of an adenovirus of subgroup B.

6. The process of claim 1 wherein the transformed primary, diploid human cell has been selected from the group consisting of a primary human retinoblast, a primary human embryonic kidney cell and a primary human amniocyte.

7. The process of claim 1, wherein the transformed primary, diploid human cell has been transfected with an adenovirus E1A coding sequence to induce unlimited proliferation.

8. The process of claim 7 wherein said packaging cell line further comprises an E1B coding sequence.

9. The process of claim 1, wherein the transformed primary, diploid human cell has been transformed by expression of adenovirus E1 proteins of a subgroup other than subgroup C.

10. The process of claim 9 wherein the subgroup other than subgroup C is subgroup B.

11. The process of claim 10, wherein said adenovirus E1 proteins are of adenovirus type 35.

12. The process of claim 1, wherein the transformed primary, diploid human cell has been transformed with a chimeric adenovirus E1 construct comprising part of a first adenovirus E1 coding sequence of a first adenovirus serotype that enables efficient transformation of primary human cells; and part of a second adenovirus E1 coding sequence of a second adenovirus serotype, wherein said second adenovirus E1 coding sequence provides the serotype-specific adenovirus E1B function(s) that enable(s) efficient propagation of recombinant adenovirus E1-deleted viruses of said second adenovirus serotype.

13. The process of claim 12 wherein said first adenovirus serotype is a subgroup C adenovirus and said second adenovirus serotype is adenovirus type 35.

14. The process of claim 12 wherein an E1A coding sequence and at least part of the E1B-21K coding sequence are of a subgroup C adenovirus, and the E1B-55K coding sequence as far as not overlapping with the 21K coding sequence is of a subgroup B adenovirus.

15. The process of claim 14 wherein said subgroup B adenovirus is adenovirus type 35.

16. The process of claim 12, wherein all E1 coding sequences are of a subgroup C adenovirus, except for at least a part of the E1B-55K coding sequence that is necessary for serotype-specific complementation of an alternative adenovirus serotype, said E1B coding sequence being of said alternative adenovirus serotype.

17. The process of claim 11, wherein the transformed primary, diploid human cell has been transformed by adenovirus E1 coding sequences located on two separate DNA molecules wherein the first DNA molecule carries at least part of the E1 coding sequences of the serotype enabling efficient transformation and the second DNA molecule carries at least part of the sequences necessary for serotype-specific complementation.

18. The process of claim 1 wherein said transformed primary, diploid cell is a cell as represented by cells deposited under deposit number 96022940 at the European Collection of Cell Cultures (ECACC) which transformed primary, diploid cell further comprises an Ad35-E1 region integrated into its genome, and wherein said Ad35-E1 region is present in a functional expression cassette.

19. The process of claim 18 wherein said Ad35-E1 region does not contain sequences overlapping with sequences present in an associated recombinant viral vector.

20. The process of claim 18, wherein said functional expression cassette comprises a heterologous promoter and a poly-adenylation signal functionally linked to said Ad35-E1 region, wherein said heterologous promoter is a human phosphoglycerate gene promoter (hPGK) and wherein said poly-adenylation signal is a hepatitis B virus poly-adenylation signal (HBV-pA).

21. The process of claim 20 wherein said Ad35-E1 region comprises the coding regions of the E1A proteins and the E1B promoter sequence linked to E1B coding sequences up to and including the stop codon of the E1B 55K protein.

22. The process of claim 20 wherein said Ad35-E1 region comprises nucleotide 468 up to and including nucleotide 3400 of the Ad35-wild-type sequence (SEQ ID NO: 44.

* * * * *